United States Patent
Ding et al.

(10) Patent No.: US 12,207,550 B2
(45) Date of Patent: Jan. 21, 2025

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Hualong Ding, Beijing (CN); Chuanjun Xia, Beijing (CN); Renmao Liu, Beijing (CN); Zhihao Cui, Beijing (CN); Chi Yuen Raymond Kwong, Beijing (CN)

(73) Assignee: BEIJING SUMMER SPROUT TECHNOLOGY CO., LTD. (CN)

( * ) Notice: Subject to any disclaimer, the term of this patent is extended or adjusted under 35 U.S.C. 154(b) by 1054 days.

(21) Appl. No.: 17/141,386

(22) Filed: Jan. 5, 2021

(65) Prior Publication Data

US 2021/0296594 A1 Sep. 23, 2021

Related U.S. Application Data

(60) Provisional application No. 62/958,498, filed on Jan. 8, 2020.

(30) Foreign Application Priority Data

Dec. 16, 2020 (CN) .......................... 202011492131.8

(51) Int. Cl.
| | | |
|---|---|---|
| H01L 51/54 | (2006.01) | |
| C07D 487/04 | (2006.01) | |
| C07D 487/14 | (2006.01) | |
| H10K 85/60 | (2023.01) | |
| H10K 50/17 | (2023.01) | |

(52) U.S. Cl.
CPC ....... *H10K 85/6572* (2023.02); *C07D 487/04* (2013.01); *C07D 487/14* (2013.01); *H10K 85/611* (2023.02); *H10K 50/17* (2023.02)

(58) Field of Classification Search
None
See application file for complete search history.

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |
| 5,844,363 A | 12/1998 | Gu et al. |
| 6,097,147 A | 8/2000 | Baldo et al. |
| 6,303,238 B1 | 10/2001 | Thompson et al. |
| 7,279,704 B2 | 10/2007 | Walters et al. |
| 7,968,146 B2 | 6/2011 | Wagner et al. |
| 2003/0230980 A1 | 12/2003 | Forrest et al. |
| 2004/0174116 A1 | 9/2004 | Lu et al. |
| 2010/0210762 A1 | 8/2010 | Hanaki et al. |
| 2015/0349273 A1 | 12/2015 | Hung et al. |
| 2016/0359122 A1 | 12/2016 | Boudreault et al. |
| 2017/0092865 A1 | 3/2017 | Yuning et al. |
| 2019/0181349 A1 * | 6/2019 | Xia ................... H10K 85/6576 |
| 2020/0062778 A1 | 2/2020 | Cui et al. |

FOREIGN PATENT DOCUMENTS

| | | |
|---|---|---|
| CN | 102643410 A | 8/2012 |
| CN | 110746427 A | 2/2020 |
| JP | 2009067720 A | 4/2009 |
| WO | 2017/148864 A1 | 9/2017 |

OTHER PUBLICATIONS

Office Action issued by the Chinese Patent Office for Application No. 202011492131.8, dated Nov. 29, 2021 (English translation included).
Office Action issued by the Chinese Patent Office for Application No. 202011492131.8, dated May 18, 2022 (English translation included).
Hiroki Uoyama et al., "Highly efficient organic light-emitting diodes from delayed fluorescence", Nature, vol. 492, Dec. 13, 2012, 7 pgs.
C.W. Tang et al., "Organic electroluminescent diodes", Appl. Phys. Ltt. 51, 913 (1987); doi: 10.1063/1.98799, 4 pgs.

* cited by examiner

*Primary Examiner* — Andrew K Bohaty
(74) *Attorney, Agent, or Firm* — BARNES & THORNBURG LLP; Jeffrey R. Stone

(57) ABSTRACT

Organic electroluminescent materials and devices are disclosed. The organic electroluminescent materials are novel dehydrobenzodiimidazole or dehydrobenzodipyrrole or its analogous structure compounds, which can be used as charge transporting materials or charge injection materials or the like in an electroluminescent device. These novel compounds have deep LUMO energy level, and have better potential and excellent application prospecty in the field of charge-transporting materials, charge injection materials or the like. An organic electroluminescent device and a compound formulation are also disclosed.

26 Claims, 3 Drawing Sheets

ORGANIC ELECTROLUMINESCENT MATERIALS AND DEVICES

CROSS-REFERENCE TO RELATED APPLICATION(S)

Figure 1:
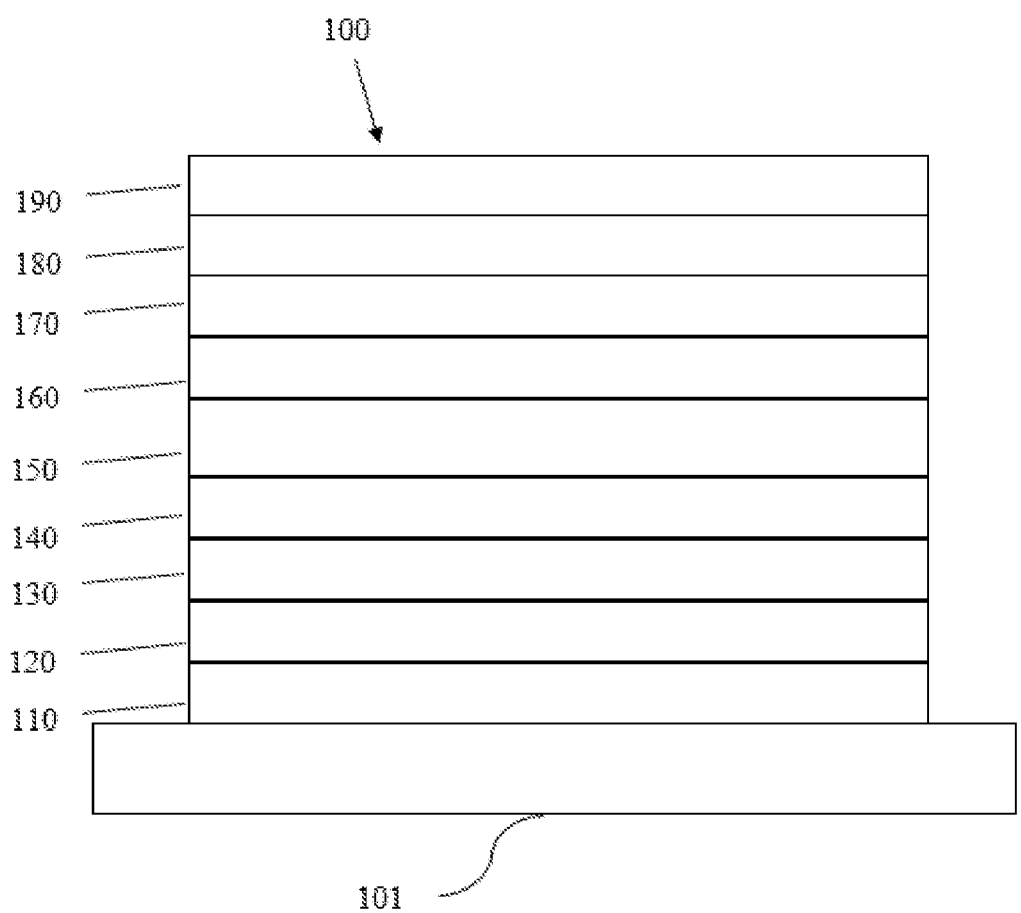

This application claims priority to U.S. Provisional Application No. 62/958,498 filed on Jan. 8, 2020 and Chinese Patent Application No. 202011492131.8 filed on Dec. 16, 2020, the disclosure of which are incorporated herein by reference in their entireties.

1. TECHNICAL FIELD

The present disclosure relates to a compound for use in organic electronic devices, such as organic light-emitting devices. More particularly, it relates to novel compounds having structures of dehydrobenzodiimidazole or dehydrobenzodipyrrole, or the like, and an organic electroluminescent device and a compound formulation comprising the compound.

2. BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This disclosure laid the foundation for the development of modem organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

In an OLED device, a hole injection layer (HIL) facilitates hole injection from the ITO anode to the organic layers. To achieve a low device driving voltage, it is important to have a minimum charge injection barrier from the anode. Various HIL materials have been developed such as triarylamine compounds having a shallow HOMO energy levels, very electron deficient heterocycles, and triarylamine compounds doped with P-type conductive dopants. To improve OLED performance such as longer device lifetime, higher efficiency and/or lower voltage, it is crucial to develop HIL, HTL materials with better performance.

The organic light emitting display device uses a hole injection layer and an electron injection layer to promote charge injection. The hole injection layer is a functional layer formed from a single material or more than one material. Methods involving a single material generally utilize materials with deep LUMO levels, while methods involving more than one material are performed by doping a hole transporting material with a P-type, deep-LUMO material. The commonality between these two methods is the use of deep-LUMO materials.

However, materials with deep LUMO levels are not easily synthesized due to their substituents with strong electron-withdrawing ability, and it is difficult to possess both deep LUMO level, high stability, and high film-forming ability. For example, F4-TCNQ (a P-type hole injection material), although having a deep LUMO level, has an extremely low vapor deposition temperature, affecting deposition control and production performance reproducibility and device thermal stability; and, for another example, HATCN has problems in film formation in devices due to strong crystallinity, and the LUMO level thereof is not deep enough to be used as a P-type dopant. Since the hole injection layer has a great influence on the voltage, efficiency and lifetime of an OLED device, it is very important and urgent in the industry for the development of materials with a deep LUMO level, high stability and high film-forming ability.

3. SUMMARY

The present disclosure intends to provide a series of novel compounds having a structure of dehydrobenzodiimidazole or dehydrobenzodipyrrole, or the like, to address at least some of the above problems. The compounds may be used as charge-transporting materials, charge injection materials or the like in organic electroluminescent devices. These novel compounds have deep LUMO energy level, and have better potential and excellent application prospecty in the field of charge-transporting materials, charge injection materials or the like.

According to an embodiment of the present disclosure, a compound having Formula 1 is disclosed:

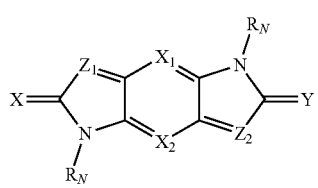

Formula 1 wherein $X_1$ and $X_2$ are each independently selected from the group consisting of CR and N;

X and Y are each independently selected from the group consisting of O, S, Se, NR', and CR"R"';

$Z_1$ and $Z_2$ are each independently selected from the group consisting of CR and N; and when $Z_1$ and $Z_2$ are both CR, at least one of X and Y is selected from the group consisting of S, Se, NR', and CR"R"';

$R_N$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

R, R', R" and R"' are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein at least one of R, R', R" and R"' is a group having at least one electron-withdrawing group;

Any adjacent R, R', R" and R"' substituents may be optionally joined to form a ring.

According to yet another embodiment, an organic light-emitting device is also disclosed, which comprises an anode, a cathode, and organic layer between the anode and the cathode, wherein the organic layer comprises a compound having Formula 1:

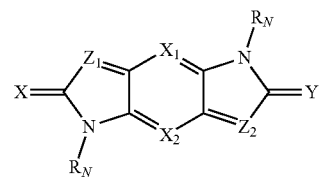

Formula 1 wherein;

$X_1$ and $X_2$ are each independently selected from the group consisting of CR and N;

X and Y are each independently selected from the group consisting of O, S, Se, NR', and CR"R"';

$Z_1$ and $Z_2$ are each independently selected from the group consisting of CR and N; and when $Z_1$ and $Z_2$ are both CR, at least one of X and Y is selected from the group consisting of S, Se, NR', and CR"R"';

$R_N$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

R, R', R" and R'" are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof; wherein at least one of R, R', R" and R'" is a group having at least one electron-withdrawing group;

Any adjacent R, R', R" and R'" substituents may be optionally joined to form a ring.

According to another embodiment of the present disclosure, a compound formulation is also disclosed, which comprises the compound having the structure of Formula 1.

The novel compounds having a structure of dehydrobenzodiimidazole or dehydrobenzodipyrrole or the like as disclosed in the present disclosure may be used as charge-transporting materials and charge injection materials in electroluminescent devices. Such novel compounds have deep LUMO energy level, and have better potential and excellent application prospect in the field of charge-transporting materials, charge injection materials or the like.

4. BRIEF DESCRIPTION OF THE DRAWINGS

FIG. 1 schematically shows an organic light emitting device that may incorporate the compound and compound formulation disclosed herein.

Figure 2:
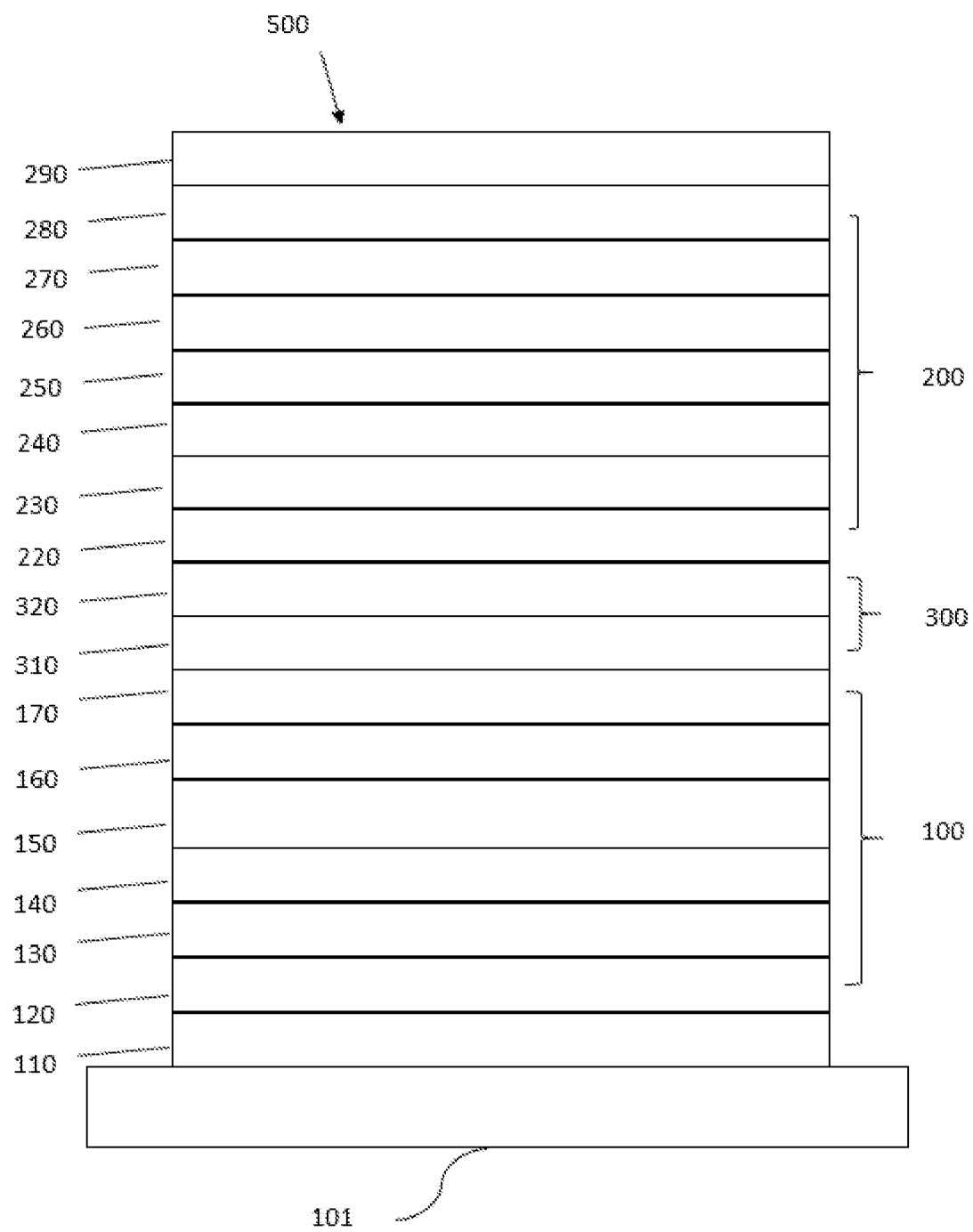

FIG. 2 schematically shows a tandem organic light emitting device that may incorporate the compound and compound formulation disclosed herein.

Figure 3:
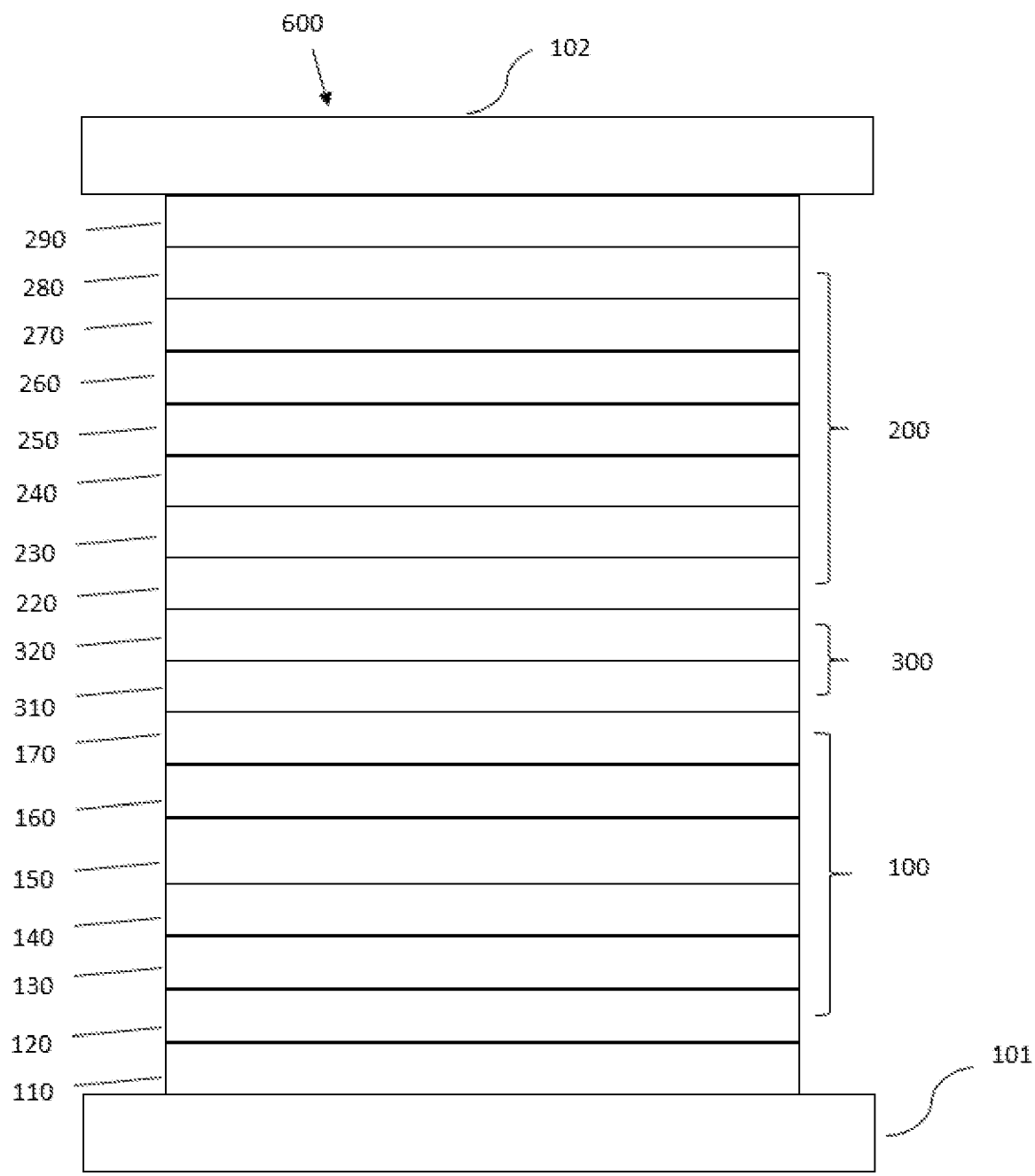

FIG. 3 schematically shows another tandem organic light emitting device that may incorporate the compound and compound formulation disclosed herein.

Figure 4:
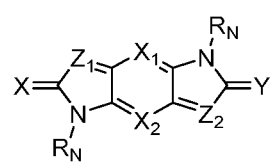

FIG. 4 shows the structural Formula 1 of compound disclosed herein.

5. DETAILED DESCRIPTION

OLEDs may be fabricated on various types of substrates such as glass, plastic, and metal foil. FIG. 1 schematically shows the organic light emitting device 100 without limitation. The figures are not necessarily drawn to scale. Some of the layer in the figure may also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely, such as an electron blocking layer. It may also include other layers not specifically described. Within each layer, a single material or a mixture of multiple materials may be used to achieve optimum performance. Any functional layer may include several sublayers. For example, the emissive layer may have a two layers of different emitting materials to achieve desired emission spectrum. Also for example, the hole transporting layer may comprise the first hole transporting layer and the second hole transporting layer.

In one embodiment, an OLED may be described as having an "organic layer" disposed between a cathode and an anode. This organic layer may comprise a single layer or multiple layers.

In one embodiment, two or more OLED units may be series connection to form a tandem OLED. FIG. 2 schematically shows the tandem organic light emitting device 500 without limitation. The device 500 may include a substrate 101, an anode 110, a first unit 100, a charge generation layer 300, a second unit 200, and a cathode 290. Wherein the first unit 100 includes a hole injection layer 120, a hole transporting layer 130, an electron blocking layer 140, an emissive layer 150, a hole blocking layer 160, an electron transporting layer 170, and the second unit 200 includes a hole injection layer 220, a hole transporting layer 230, an electron blocking layer 240, an emissive layer 250, a hole blocking layer 260, an electron transporting layer 270, and an electron injection layer 280. The charge generation layers 300 include an N type charge generation layer 310 and a P type charge generation layer 320. The device 500 may be manufactured by sequentially depositing the described layers.

An OLED may be encapsulated by a barrier layer. FIG. 3 schematically shows the organic light emitting device 600 without limitation. FIG. 3 differs from FIG. 2 in that the organic light emitting device include a barrier layer 102, which is above the cathode 290, to protect it from harmful species from the environment such as moisture and oxygen. Any material that may provide the barrier function may be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the disclosure may be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs may exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy may activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states may potentially reach 75%. The total singlet fraction may be 100%, far exceeding 25% of the spin statistics limit for electrically generated excitons.

E-type delayed fluorescence characteristics may be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain may be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring may be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2'-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group may also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art may readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms may be partially or fully replaced by deuterium. Other atoms such as carbon and nitrogen, may also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions.

In the present disclosure, unless otherwise defined, when any term of the group consisting of substituted alkyl, substituted cycloalkyl, substituted heteroalkyl, substituted aralkyl, substituted alkoxy, substituted aryloxy, substituted alkenyl, substituted alkynyl, substituted aryl, substituted heteroaryl, substituted alkylsilyl, substituted arylsilyl, substituted amine, substituted acyl, substituted carbonyl, substituted carboxylic acid group, substituted ester group, substituted sulfinyl, substituted sulfonyl and substituted phosphoroso is used, it means that any group of alkyl, cycloalkyl, heteroalkyl, aralkyl, alkoxy, aryloxy, alkenyl, alkynyl, aryl, heteroaryl, alkylsilyl, arylsilyl, amine, acyl, carbonyl, carboxylic acid group, ester group, sulfinyl, sulfonyl and phosphoroso may be substituted with one or more groups selected from the group consisting of deuterium, a halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted aralkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an alkynyl group, an acyl group, a carbonyl group, a carboxylic acid group, an ester group, an ether group, a cyano group, an isocyano group, a thiol group, a sulfonyl group, a sulfinyl group and a phosphoroso group, and combinations thereof.

In the compounds mentioned in the present disclosure, adjacent substituents in the compounds may not connect to form a ring unless otherwise explicitly defined, for example, adjacent substituents may be optionally joined to form a ring. In the compounds mentioned in the present disclosure, adjacent substituents may be optionally joined to form a ring, including both the case where adjacent substituents may be joined to form a ring, and the case where adjacent substituents are not joined to form a ring. When adjacent substituents may be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents may be optionally joined to form a ring is also intended to mean that two substituents bonded to the same carbon atom are joined to each other via a chemical bond to form a ring, which may be exemplified by the following formula:

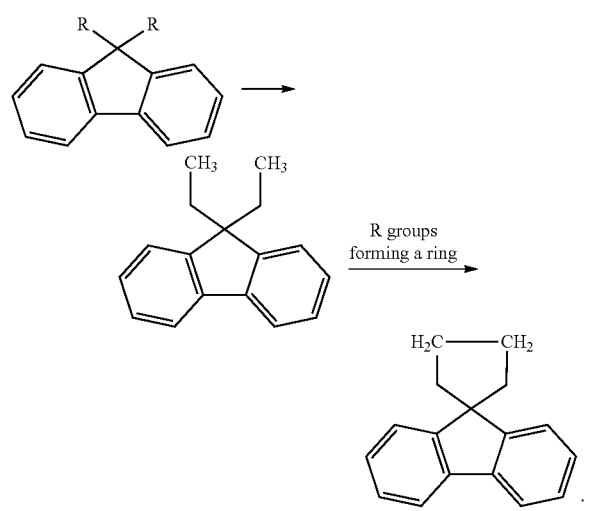

The expression that adjacent substituents may be optionally joined to form a ring is also intended to mean that two substituents bonded to carbon atoms which are directly bonded to each other are joined to each other via a chemical bond to form a ring, which may be exemplified by the following formula:

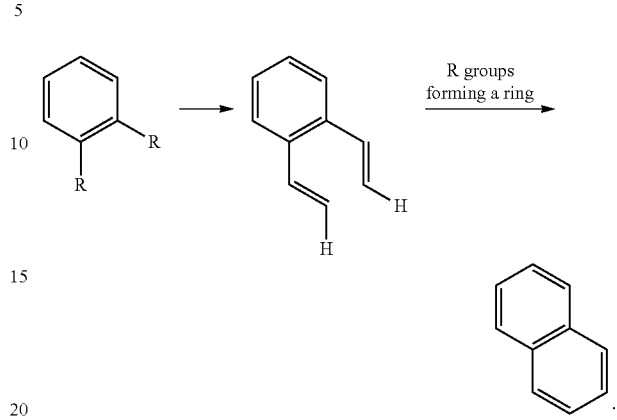

Furthermore, the expression that adjacent substituents may be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

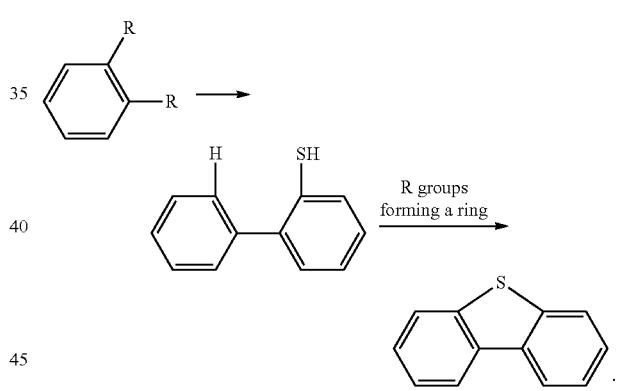

According to an embodiment of the present disclosure, a compound having Formula 1 is disclosed:

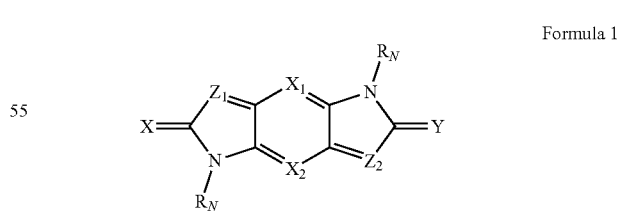

Formula 1 wherein;
$X_1$ and $X_2$ are each independently selected from the group consisting of CR and N;
X and Y are each independently selected from the group consisting of O, S, Se, NR' and CR"R'";
$Z_1$ and $Z_2$ are each independently selected from the group consisting of CR and N; when $Z_1$ and $Z_2$ are both CR, at least one of X and Y is selected from the group consisting of S, Se, NR', and CR"R'";

$R_N$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

R, R', R" and R''' are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof; wherein at least one of R, R', R" and R''' is a group having at least one electron-withdrawing group;

Any adjacent R, R', R" and R''' substituents may be optionally joined to form a ring.

In the present embodiment, the expression that any adjacent R, R', R" and R''' substituents may be optionally joined to form a ring is intended to mean that any two adjacent substituents of R, R', R" and R''', for example, between two R, between R and R', between R and R", between R' and R", between R and R''', and between R" and R''', any one or more of them may be optionally joined to form a ring. Obviously, any adjacent R, R', R" and R''' substituents may not be joined to form a ring.

According to an embodiment of the present disclosure, wherein X and Y are each independently selected from S, Se, NR' or CR"R'".

According to an embodiment of the present disclosure, $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof.

According to an embodiment of the present disclosure, $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, a substituted or unsubstituted heteroaryl group having 3 to 30 carbon atoms, and combinations thereof.

According to an embodiment of the present disclosure, wherein $Z_1$ and $Z_2$ are N.

According to an embodiment of the present disclosure, wherein $X_1$ and $X_2$ are CR, wherein R is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof.

According to an embodiment of the present disclosure, wherein $X_1$ and $X_2$ are CR, wherein R is, at each occurrence identically or differently, selected from the group consisting of hydrogen, deuterium, halogen, nitro, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryl group having 6 to 30 carbon atoms, a substituted or unsubstituted heteroaryl group having 3 to 30 carbon atoms, and combinations thereof.

According to an embodiment of the present disclosure, wherein $X_1$ and $X_2$ are same.

According to an embodiment of the present disclosure, wherein $X_1$ and $X_2$ are CR, wherein R is, at each occurrence identically or differently, a group having at least one electron-withdrawing group.

According to an embodiment of the present disclosure, each of X and Y is independently selected from CR"R''' ' or NR'; wherein R', R" and R'" are, at each occurrence identically or differently, groups each having at least one electron-withdrawing group.

According to an embodiment of the present disclosure, X and Y are CR"R'".

According to an embodiment of the present disclosure, wherein $X_1$ and $X_2$ are CR; wherein R is, at each occurrence identically or differently, a substituted or unsubstituted aryl group having 6 to 30 carbon atoms, a substituted or unsubstituted heteroaryl group having 3 to 30 carbon atoms, preferably the aryl group and/or the heteroaryl group are substituted with at least one electron-withdrawing group.

According to an embodiment of the present disclosure, wherein $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, a substituted or unsubstituted heteroaryl group having 3 to 30 carbon atoms, and combinations thereof;

Wherein $Z_1$ and $Z_2$ are N;
Wherein $X_1$ and $X_2$ are CR, wherein R is, at each occurrence identically or differently, a group having at least one electron-withdrawing group;
Wherein X and Y are CR"R'", wherein R" and R'" are, at each occurrence identically or differently, groups each having at least one electron-withdrawing group.

According to an embodiment of the present disclosure, wherein $R_N$ is, at each occurrence identically or differently, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, or a substituted or unsubstituted heteroaryl group having 3 to 30 carbon atoms;

$Z_1$ and $Z_2$ are N;
$X_1$ and $X_2$ are CR, wherein R is, at each occurrence identically or differently, a group having at least one electron-withdrawing group;
X and Y are, at each occurrence identically or differently, selected from the group consisting of S and Se.

According to an embodiment of the present disclosure, wherein $X_1$ and $X_2$ are N.

According to an embodiment of the present disclosure, the Hammett's constant of the electron-withdrawing group is ≥0.05, preferably ≥0.3, more preferably ≥0.5.

The electron-withdrawing group of the present disclosure has a Hammett's substituent constant value of ≥0.05, preferably ≥0.3, more preferably ≥0.5, and thus has a strong electron withdrawing ability, which may significantly reduce the LUMO energy level of the compound and improve charge mobility.

It should be noted that the Hammett's substituent constant value includes Hammett's substituent para-position constant and/or meta-position constant. As long as one of the para-constant and the meta-constant is equal to or greater than 0.05, the group is preferred for the present disclosure.

According to an embodiment of the present disclosure, the electron-withdrawing group is selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxy group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms, and an arylsilyl group having 6 to 20 carbon atoms, which is substituted with one or more of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and combinations thereof.

According to an embodiment of the present disclosure, the electron-withdrawing group is selected from the group consisting of F, $CF_3$, $OCF_3$, $SF_5$, $SO_2CF_3$, cyano, isocyano, SCN, OCN, pyrimidinyl, triazinyl, and combinations thereof.

According to an embodiment of the present disclosure, each of X and Y is independently selected from the group consisting of:

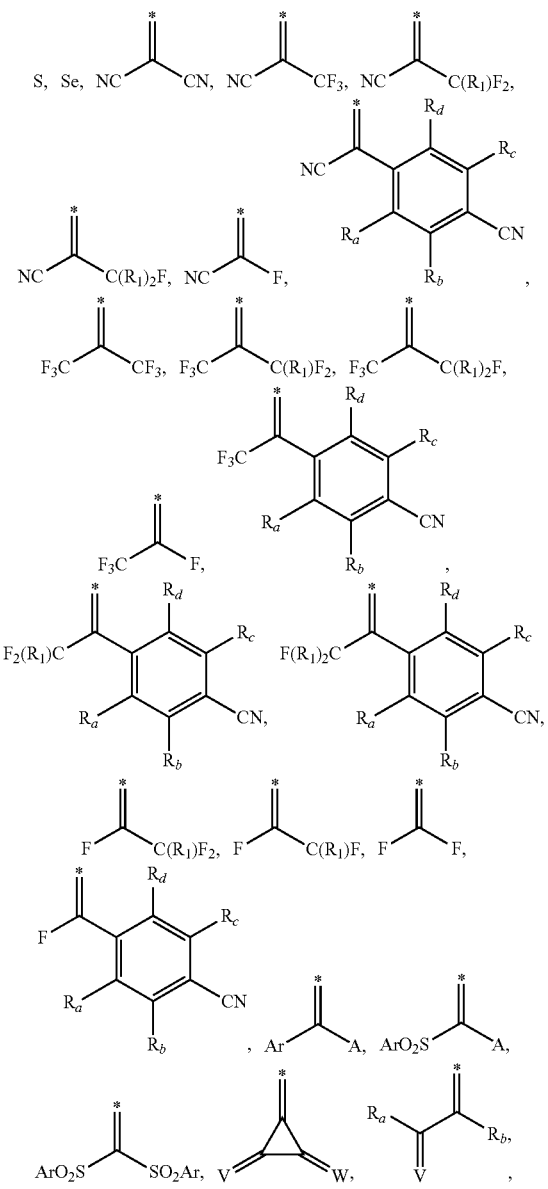

-continued

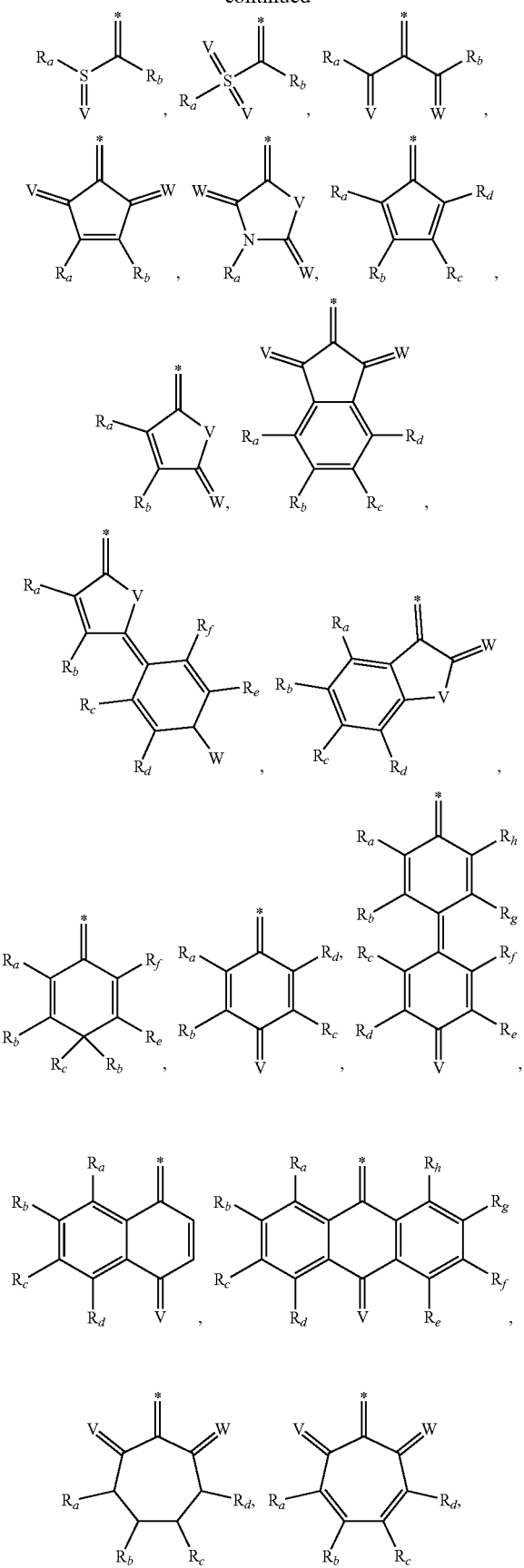

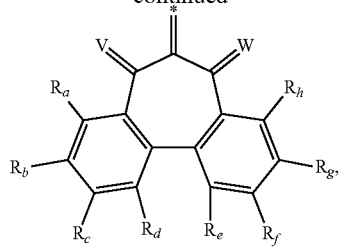

wherein $R_1$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

preferably, $R_1$ is, at each occurrence identically or differently, selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof, wherein V and W are, at each occurrence identically or differently, selected from the group consisting of $CR_vR_w$, $NR_v$, O, S and Se;

wherein Ar is, at each occurrence identically or differently, selected from a substituted or unsubstituted aryl group having 6 to 30 carbon atoms, or a substituted or unsubstituted heteroaryl group having 3 to 30 carbon atoms;

wherein A, $R_a$, $R_b$, $R_c$, $R_d$, $R_e$, $R_f$, $R_g$, $R_h$, $R_v$, and $R_w$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof, wherein A is a group having at least one electron-withdrawing group, and for any one of the structures, when one or more of $R_a$, $R_b$, $R_c$, $R_d$, $R_e$, $R_f$, $R_g$, $R_h$, $R_v$ and $R_w$ is(are) present, at least one of them is a group having at least one electron-withdrawing group; preferably, the group having at least one electron-withdrawing group is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

In the present embodiment, "*" indicates the position at which the X and Y groups are attached to the dehydrobenzodiimidazole ring or the dehydrobenzodipyrrole ring in Formula 1.

According to an embodiment of the present disclosure, each of X and Y is independently selected from the group consisting of:

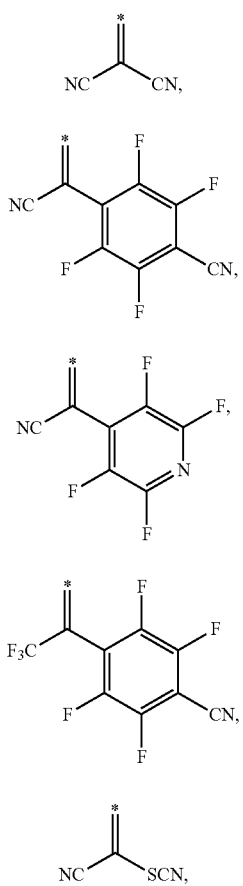

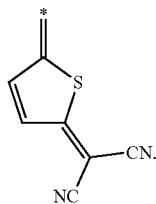

In the present embodiment, "*" indicates the position at which the X and Y groups are attached to the dehydrobenzodiimidazole ring or the dehydrobenzodipyrrole ring in Formula 1.

According to an embodiment of the present disclosure, wherein $X_1$ and $X_2$ are, at each occurrence identically or differently, selected from CR, wherein R groups are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, an unsubstituted alkyl group having 1 to 20 carbon atoms, an unsubstituted cycloalkyl group having 3 to 20 ring carbon atoms, an unsubstituted alkoxy group having 1 to 20 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms, and a heteroaryl group having 3 to 30 carbon atoms which is substituted with one or more groups selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, and combinations thereof.

According to an embodiment of the present disclosure, wherein R groups are, at each occurrence identically or differently, selected from the group consisting of hydrogen, deuterium, methyl, isopropyl, $NO_2$, $SO_2CH_3$, $SCF_3$, $C_2F_5$, $OC_2F_5$, $OCH_3$, p-methylphenyl, diphenylmethylsilyl, phenyl, methoxyphenyl, 2,6-diisopropylphenyl, biphenyl, polyfluorophenyl, difluoropyridyl, nitrophenyl, dimethylthiazolyl, CN, vinyl substituted with one or more of CN and $CF_3$, ethynyl substituted with one of CN and $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and $CF_3$, tetrafluoropyridyl, pyrimidinyl, triazinyl, pyridyl, diphenylboranyl, oxaboraanthryl, and combinations thereof.

According to an embodiment of the present disclosure, wherein X and Y are

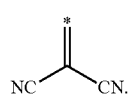

According to an embodiment of the present disclosure, wherein R groups are, at each occurrence identically or differently, selected from the group consisting of:
B1
B2
B3
B4
B5
B6
B7
B8
B9
B10
B11
B12
B13
-continued
B14
B15
B16
B17
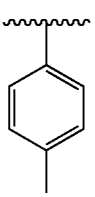
B18
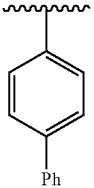
B19
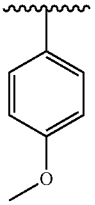
B20
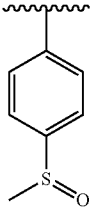
B21
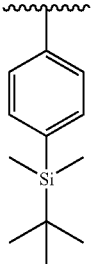

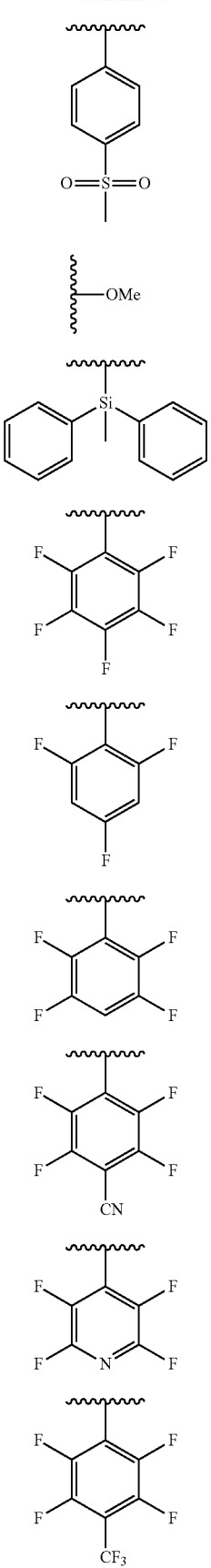

-continued
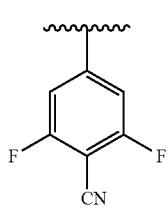 B39
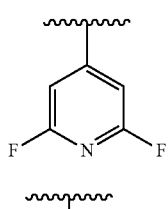 B40
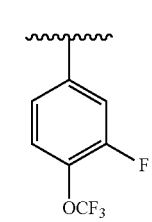 B41
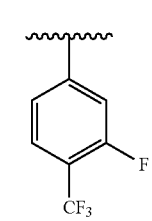 B42
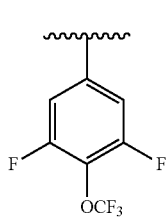 B43
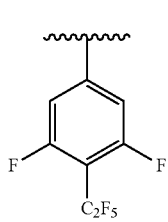 B44
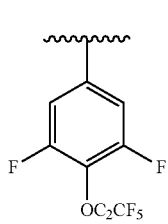 B45
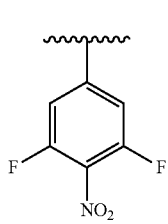 B46
-continued
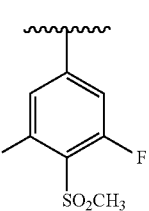 B47
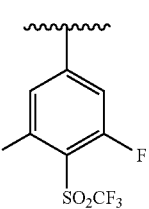 B48
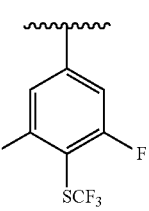 B49
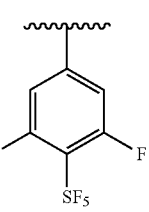 B50
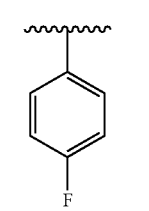 B51
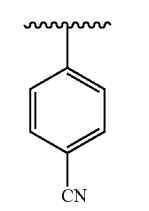 B52
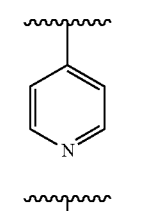 B53
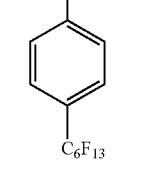 B54

-continued

B55: 4-(trifluoromethyl)phenyl

B56: 4-(trifluoromethoxy)phenyl

B57: 4-(pentafluoroethyl)phenyl

B58: 4-(pentafluoroethoxy)phenyl

B59: 4-nitrophenyl

B60: 4-(methylsulfonyl)phenyl

B61: 4-(trifluoromethylsulfonyl)phenyl

B62: 4-(trifluoromethylthio)phenyl

-continued

B63: 4-(pentafluorosulfanyl)phenyl

B64: 2,6-diisopropyl-4-(trifluoromethyl)phenyl

B65: pyrimidin-2-yl

B66: 2,4-dimethylthiazol-5-yl

B67: 4,6-bis(trifluoromethyl)-1,3,5-triazin-2-yl

B68: 3,5-bis(trifluoromethyl)phenyl

B69: 2,5-bis(trifluoromethyl)phenyl

B70: 2,4-bis(trifluoromethyl)phenyl

B71: 2,4,6-tris(trifluoromethyl)phenyl

| | |
|---|---|
| 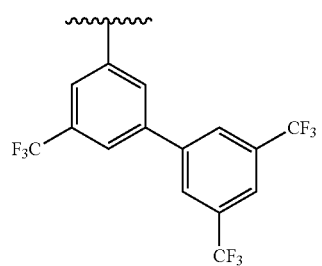 B72 | 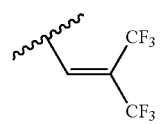 B79 |
| 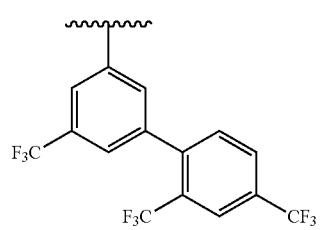 B73 | 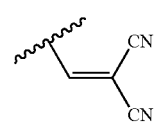 B80 |
| 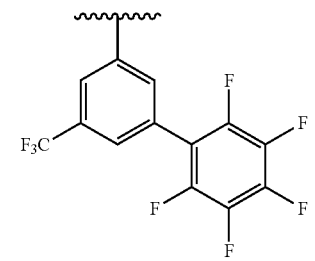 B74 | 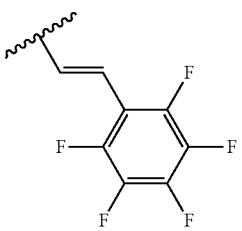 B81 |
| 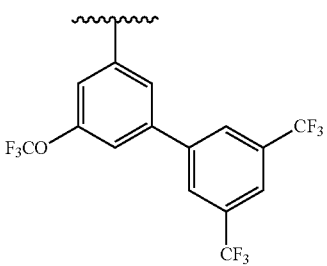 B75 | 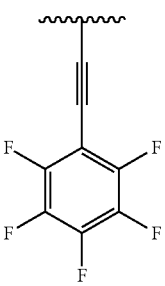 B82 |
| 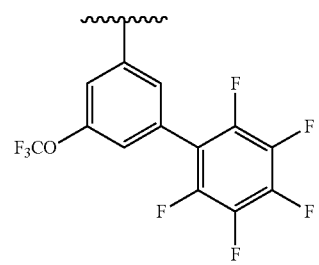 B76 | 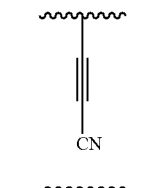 B83 |
| 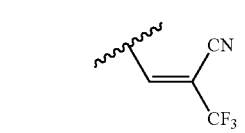 B77 | 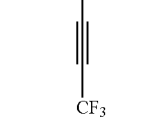 B84 |
| 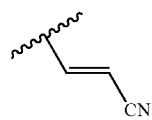 B78 | 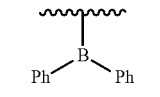 B85 |
| | 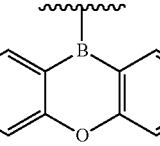 B86 |
| | 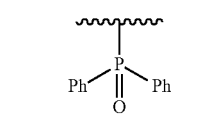 B87 |
| | 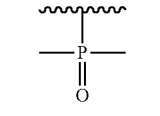 B88 |

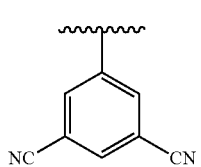 B89
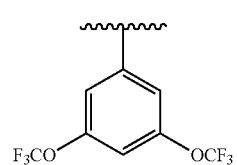 B90
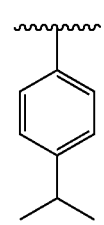 B91
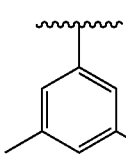 B92
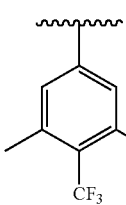 B93
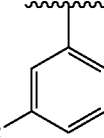 B94
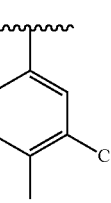 B95
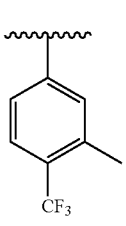 B96
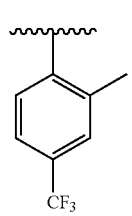 B97
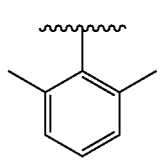 B98
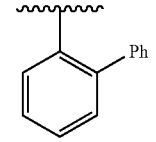 B99
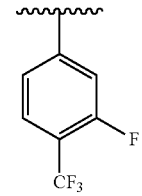 B100
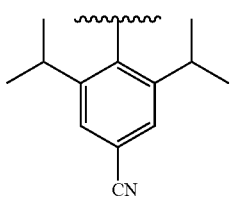 B101
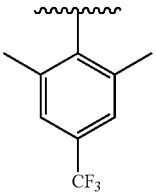 B102
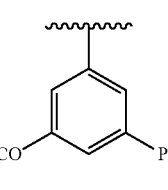 B103
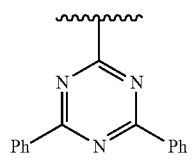 B104

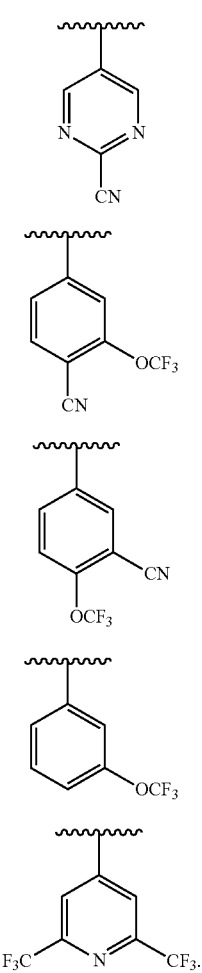

B105

B106

B107

B108

B109

In the present embodiment, " ⁓ " indicates the position at which the R group is attached to dehydrobenzodiimidazole ring or the dehydrobenzodipyrrole ring in Formula 1.

According to an embodiment of the present disclosure, wherein each of $X_1$ and $X_2$ is independently selected from CR and the two R groups are the same.

According to an embodiment of the present disclosure, wherein in the compound, when $X_1$ and $X_2$ are CR, and each R of $X_1$ and $X_2$ is identical;

wherein $Z_1$, $Z_2$, X, Y, each R of $X_1$ and $X_2$, and $R_N$ are correspondingly selected from the atoms or groups as shown in the following table, and the Compound 1 to Compound 990 and Compound 1003 to Compound 1016 are:

| No. | $Z_1 = Z_2$ | X = Y | R | $R_N$ |
|---|---|---|---|---|
| Compound 1 | N | A1 | B1 | B14 |
| Compound 2 | N | A1 | B2 | B14 |
| Compound 3 | N | A1 | B3 | B14 |
| Compound 4 | N | A1 | B4 | B14 |
| Compound 5 | N | A1 | B5 | B14 |
| Compound 6 | N | A1 | B6 | B14 |
| Compound 7 | N | A1 | B7 | B14 |
| Compound 8 | N | A1 | B8 | B14 |
| Compound 9 | N | A1 | B9 | B14 |
| Compound 10 | N | A1 | B10 | B14 |
| Compound 11 | N | A1 | B11 | B14 |
| Compound 12 | N | A1 | B12 | B14 |
| Compound 13 | N | A1 | B13 | B14 |
| Compound 14 | N | A1 | B14 | B14 |
| Compound 15 | N | A1 | B15 | B14 |
| Compound 16 | N | A1 | B16 | B14 |
| Compound 17 | N | A1 | B17 | B14 |
| Compound 18 | N | A1 | B18 | B14 |
| Compound 19 | N | A1 | B19 | B14 |
| Compound 20 | N | A1 | B20 | B14 |
| Compound 21 | N | A1 | B21 | B14 |
| Compound 22 | N | A1 | B22 | B14 |
| Compound 23 | N | A1 | B23 | B14 |
| Compound 24 | N | A1 | B24 | B14 |
| Compound 25 | N | A1 | B25 | B14 |
| Compound 26 | N | A1 | B26 | B14 |
| Compound 27 | N | A1 | B27 | B14 |
| Compound 28 | N | A1 | B28 | B14 |
| Compound 29 | N | A1 | B29 | B14 |
| Compound 30 | N | A1 | B30 | B14 |
| Compound 31 | N | A1 | B31 | B14 |
| Compound 32 | N | A1 | B32 | B14 |
| Compound 33 | N | A1 | B33 | B14 |
| Compound 34 | N | A1 | B34 | B14 |
| Compound 35 | N | A1 | B35 | B14 |
| Compound 36 | N | A1 | B36 | B14 |
| Compound 37 | N | A1 | B37 | B14 |
| Compound 38 | N | A1 | B38 | B14 |
| Compound 39 | N | A1 | B39 | B14 |
| Compound 40 | N | A1 | B40 | B14 |
| Compound 41 | N | A1 | B41 | B14 |
| Compound 42 | N | A1 | B42 | B14 |
| Compound 43 | N | A1 | B43 | B14 |
| Compound 44 | N | A1 | B44 | B14 |
| Compound 45 | N | A1 | B45 | B14 |
| Compound 46 | N | A1 | B46 | B14 |
| Compound 47 | N | A1 | B47 | B14 |
| Compound 48 | N | A1 | B48 | B14 |
| Compound 49 | N | A1 | B49 | B14 |
| Compound 50 | N | A1 | B50 | B14 |
| Compound 51 | N | A1 | B51 | B14 |
| Compound 52 | N | A1 | B52 | B14 |
| Compound 53 | N | A1 | B53 | B14 |
| Compound 54 | N | A1 | B54 | B14 |
| Compound 55 | N | A1 | B55 | B14 |
| Compound 56 | N | A1 | B56 | B14 |
| Compound 57 | N | A1 | B57 | B14 |
| Compound 58 | N | A1 | B58 | B14 |
| Compound 59 | N | A1 | B59 | B14 |
| Compound 60 | N | A1 | B60 | B14 |
| Compound 61 | N | A1 | B61 | B14 |
| Compound 62 | N | A1 | B62 | B14 |
| Compound 63 | N | A1 | B63 | B14 |
| Compound 64 | N | A1 | B64 | B14 |
| Compound 65 | N | A1 | B65 | B14 |
| Compound 66 | N | A1 | B66 | B14 |
| Compound 67 | N | A1 | B67 | B14 |
| Compound 68 | N | A1 | B68 | B14 |
| Compound 69 | N | A1 | B69 | B14 |
| Compound 70 | N | A1 | B70 | B14 |
| Compound 71 | N | A1 | B71 | B14 |
| Compound 72 | N | A1 | B72 | B14 |
| Compound 73 | N | A1 | B73 | B14 |
| Compound 74 | N | A1 | B74 | B14 |
| Compound 75 | N | A1 | B75 | B14 |
| Compound 76 | N | A1 | B76 | B14 |
| Compound 77 | N | A1 | B77 | B14 |
| Compound 78 | N | A1 | B78 | B14 |
| Compound 79 | N | A1 | B79 | B14 |
| Compound 80 | N | A1 | B80 | B14 |
| Compound 81 | N | A1 | B81 | B14 |
| Compound 82 | N | A1 | B82 | B14 |
| Compound 83 | N | A1 | B83 | B14 |
| Compound 84 | N | A1 | B84 | B14 |
| Compound 85 | N | A1 | B85 | B14 |
| Compound 86 | N | A1 | B86 | B14 |
| Compound 87 | N | A1 | B87 | B14 |
| Compound 88 | N | A1 | B88 | B14 |
| Compound 89 | N | A2 | B1 | B14 |

| No. | $Z_1 = Z_2$ | X = Y | R | $R_N$ |
|---|---|---|---|---|
| Compound 90 | N | A2 | B6 | B14 |
| Compound 91 | N | A2 | B12 | B14 |
| Compound 92 | N | A2 | B14 | B14 |
| Compound 93 | N | A2 | B20 | B14 |
| Compound 94 | N | A2 | B28 | B14 |
| Compound 95 | N | A2 | B30 | B14 |
| Compound 96 | N | A2 | B35 | B14 |
| Compound 97 | N | A2 | B38 | B14 |
| Compound 98 | N | A2 | B39 | B14 |
| Compound 99 | N | A2 | B41 | B14 |
| Compound 100 | N | A2 | B42 | B14 |
| Compound 101 | N | A2 | B49 | B14 |
| Compound 102 | N | A2 | B54 | B14 |
| Compound 103 | N | A2 | B56 | B14 |
| Compound 104 | N | A2 | B64 | B14 |
| Compound 105 | N | A2 | B68 | B14 |
| Compound 106 | N | A2 | B69 | B14 |
| Compound 107 | N | A2 | B70 | B14 |
| Compound 108 | N | A2 | B72 | B14 |
| Compound 109 | N | A2 | B75 | B14 |
| Compound 110 | N | A2 | B78 | B14 |
| Compound 111 | N | A2 | B79 | B14 |
| Compound 112 | N | A2 | B80 | B14 |
| Compound 113 | N | A2 | B82 | B14 |
| Compound 114 | N | A2 | B83 | B14 |
| Compound 115 | N | A2 | B85 | B14 |
| Compound 116 | N | A2 | B88 | B14 |
| Compound 117 | N | A3 | B1 | B14 |
| Compound 118 | N | A3 | B6 | B14 |
| Compound 119 | N | A3 | B12 | B14 |
| Compound 120 | N | A3 | B14 | B14 |
| Compound 121 | N | A3 | B20 | B14 |
| Compound 122 | N | A3 | B28 | B14 |
| Compound 123 | N | A3 | B30 | B14 |
| Compound 124 | N | A3 | B35 | B14 |
| Compound 125 | N | A3 | B38 | B14 |
| Compound 126 | N | A3 | B39 | B14 |
| Compound 127 | N | A3 | B41 | B14 |
| Compound 128 | N | A3 | B42 | B14 |
| Compound 129 | N | A3 | B49 | B14 |
| Compound 130 | N | A3 | B54 | B14 |
| Compound 131 | N | A3 | B56 | B14 |
| Compound 132 | N | A3 | B64 | B14 |
| Compound 133 | N | A3 | B68 | B14 |
| Compound 134 | N | A3 | B69 | B14 |
| Compound 135 | N | A3 | B70 | B14 |
| Compound 136 | N | A3 | B72 | B14 |
| Compound 137 | N | A3 | B75 | B14 |
| Compound 138 | N | A3 | B78 | B14 |
| Compound 139 | N | A3 | B79 | B14 |
| Compound 140 | N | A3 | B80 | B14 |
| Compound 141 | N | A3 | B82 | B14 |
| Compound 142 | N | A3 | B83 | B14 |
| Compound 143 | N | A3 | B85 | B14 |
| Compound 144 | N | A3 | B88 | B14 |
| Compound 145 | N | A4 | B1 | B14 |
| Compound 146 | N | A4 | B6 | B14 |
| Compound 147 | N | A4 | B12 | B14 |
| Compound 148 | N | A4 | B14 | B14 |
| Compound 149 | N | A4 | B20 | B14 |
| Compound 150 | N | A4 | B28 | B14 |
| Compound 151 | N | A4 | B30 | B14 |
| Compound 152 | N | A4 | B35 | B14 |
| Compound 153 | N | A4 | B38 | B14 |
| Compound 154 | N | A4 | B39 | B14 |
| Compound 155 | N | A4 | B41 | B14 |
| Compound 156 | N | A4 | B42 | B14 |
| Compound 157 | N | A4 | B49 | B14 |
| Compound 158 | N | A4 | B54 | B14 |
| Compound 159 | N | A4 | B56 | B14 |
| Compound 160 | N | A4 | B64 | B14 |
| Compound 161 | N | A4 | B68 | B14 |
| Compound 162 | N | A4 | B69 | B14 |
| Compound 163 | N | A4 | B70 | B14 |
| Compound 164 | N | A4 | B72 | B14 |
| Compound 165 | N | A4 | B75 | B14 |
| Compound 166 | N | A4 | B78 | B14 |
| Compound 167 | N | A4 | B79 | B14 |
| Compound 168 | N | A4 | B80 | B14 |
| Compound 169 | N | A4 | B82 | B14 |
| Compound 170 | N | A4 | B83 | B14 |
| Compound 171 | N | A4 | B85 | B14 |
| Compound 172 | N | A4 | B88 | B14 |
| Compound 173 | N | A5 | B1 | B14 |
| Compound 174 | N | A5 | B6 | B14 |
| Compound 175 | N | A5 | B12 | B14 |
| Compound 176 | N | A5 | B14 | B14 |
| Compound 177 | N | A5 | B20 | B14 |
| Compound 178 | N | A5 | B28 | B14 |
| Compound 179 | N | A5 | B30 | B14 |
| Compound 180 | N | A5 | B35 | B14 |
| Compound 181 | N | A5 | B38 | B14 |
| Compound 182 | N | A5 | B39 | B14 |
| Compound 183 | N | A5 | B41 | B14 |
| Compound 184 | N | A5 | B42 | B14 |
| Compound 185 | N | A5 | B49 | B14 |
| Compound 186 | N | A5 | B54 | B14 |
| Compound 187 | N | A5 | B56 | B14 |
| Compound 188 | N | A5 | B64 | B14 |
| Compound 189 | N | A5 | B68 | B14 |
| Compound 190 | N | A5 | B69 | B14 |
| Compound 191 | N | A5 | B70 | B14 |
| Compound 192 | N | A5 | B72 | B14 |
| Compound 193 | N | A5 | B75 | B14 |
| Compound 194 | N | A5 | B78 | B14 |
| Compound 195 | N | A5 | B79 | B14 |
| Compound 196 | N | A5 | B80 | B14 |
| Compound 197 | N | A5 | B82 | B14 |
| Compound 198 | N | A5 | B83 | B14 |
| Compound 199 | N | A5 | B85 | B14 |
| Compound 200 | N | A5 | B88 | B14 |
| Compound 201 | N | A6 | B1 | B14 |
| Compound 202 | N | A6 | B6 | B14 |
| Compound 203 | N | A6 | B12 | B14 |
| Compound 204 | N | A6 | B14 | B14 |
| Compound 205 | N | A6 | B20 | B14 |
| Compound 206 | N | A6 | B28 | B14 |
| Compound 207 | N | A6 | B30 | B14 |
| Compound 208 | N | A6 | B35 | B14 |
| Compound 209 | N | A6 | B38 | B14 |
| Compound 210 | N | A6 | B39 | B14 |
| Compound 211 | N | A6 | B41 | B14 |
| Compound 212 | N | A6 | B42 | B14 |
| Compound 213 | N | A6 | B49 | B14 |
| Compound 214 | N | A6 | B54 | B14 |
| Compound 215 | N | A6 | B56 | B14 |
| Compound 216 | N | A6 | B64 | B14 |
| Compound 217 | N | A6 | B68 | B14 |
| Compound 218 | N | A6 | B69 | B14 |
| Compound 219 | N | A6 | B70 | B14 |
| Compound 220 | N | A6 | B72 | B14 |
| Compound 221 | N | A6 | B75 | B14 |
| Compound 222 | N | A6 | B78 | B14 |
| Compound 223 | N | A6 | B79 | B14 |
| Compound 224 | N | A6 | B80 | B14 |
| Compound 225 | N | A6 | B82 | B14 |
| Compound 226 | N | A6 | B83 | B14 |
| Compound 227 | N | A6 | B85 | B14 |
| Compound 228 | N | A6 | B88 | B14 |
| Compound 229 | N | A7 | B1 | B14 |
| Compound 230 | N | A7 | B6 | B14 |
| Compound 231 | N | A7 | B12 | B14 |
| Compound 232 | N | A7 | B14 | B14 |
| Compound 233 | N | A7 | B20 | B14 |
| Compound 234 | N | A7 | B28 | B14 |
| Compound 235 | N | A7 | B30 | B14 |
| Compound 236 | N | A7 | B35 | B14 |
| Compound 237 | N | A7 | B38 | B14 |
| Compound 238 | N | A7 | B39 | B14 |
| Compound 239 | N | A7 | B41 | B14 |
| Compound 240 | N | A7 | B42 | B14 |
| Compound 241 | N | A7 | B49 | B14 |
| Compound 242 | N | A7 | B54 | B14 |
| Compound 243 | N | A7 | B56 | B14 |

| No. | $Z_1 = Z_2$ | X = Y | R | $R_N$ |
|---|---|---|---|---|
| Compound 244 | N | A7 | B64 | B14 |
| Compound 245 | N | A7 | B68 | B14 |
| Compound 246 | N | A7 | B69 | B14 |
| Compound 247 | N | A7 | B70 | B14 |
| Compound 248 | N | A7 | B72 | B14 |
| Compound 249 | N | A7 | B75 | B14 |
| Compound 250 | N | A7 | B78 | B14 |
| Compound 251 | N | A7 | B79 | B14 |
| Compound 252 | N | A7 | B80 | B14 |
| Compound 253 | N | A7 | B82 | B14 |
| Compound 254 | N | A7 | B83 | B14 |
| Compound 255 | N | A7 | B85 | B14 |
| Compound 256 | N | A7 | B88 | B14 |
| Compound 257 | N | S | B1 | B14 |
| Compound 258 | N | S | B6 | B14 |
| Compound 259 | N | S | B12 | B14 |
| Compound 260 | N | S | B2 | B14 |
| Compound 261 | N | S | B20 | B14 |
| Compound 262 | N | S | B28 | B14 |
| Compound 263 | N | S | B30 | B14 |
| Compound 264 | N | S | B35 | B14 |
| Compound 265 | N | S | B38 | B14 |
| Compound 266 | N | S | B39 | B14 |
| Compound 267 | N | S | B41 | B14 |
| Compound 268 | N | S | B42 | B14 |
| Compound 269 | N | S | B49 | B14 |
| Compound 270 | N | S | B54 | B14 |
| Compound 271 | N | S | B56 | B14 |
| Compound 272 | N | S | B64 | B14 |
| Compound 273 | N | S | B68 | B14 |
| Compound 274 | N | S | B69 | B14 |
| Compound 275 | N | S | B70 | B14 |
| Compound 276 | N | S | B72 | B14 |
| Compound 277 | N | S | B75 | B14 |
| Compound 278 | N | S | B78 | B14 |
| Compound 279 | N | S | B79 | B14 |
| Compound 280 | N | S | B80 | B14 |
| Compound 281 | N | S | B82 | B14 |
| Compound 282 | N | S | B83 | B14 |
| Compound 283 | N | S | B85 | B14 |
| Compound 284 | N | S | B88 | B14 |
| Compound 285 | N | Se | B1 | B14 |
| Compound 286 | N | Se | B6 | B14 |
| Compound 287 | N | Se | B12 | B14 |
| Compound 288 | N | Se | B2 | B14 |
| Compound 289 | N | Se | B20 | B14 |
| Compound 290 | N | Se | B28 | B14 |
| Compound 291 | N | Se | B30 | B14 |
| Compound 292 | N | Se | B35 | B14 |
| Compound 293 | N | Se | B38 | B14 |
| Compound 294 | N | Se | B39 | B14 |
| Compound 295 | N | Se | B41 | B14 |
| Compound 296 | N | Se | B42 | B14 |
| Compound 297 | N | Se | B49 | B14 |
| Compound 298 | N | Se | B54 | B14 |
| Compound 299 | N | Se | B56 | B14 |
| Compound 300 | N | Se | B64 | B14 |
| Compound 301 | N | Se | B68 | B14 |
| Compound 302 | N | Se | B69 | B14 |
| Compound 303 | N | Se | B70 | B14 |
| Compound 304 | N | Se | B72 | B14 |
| Compound 305 | N | Se | B75 | B14 |
| Compound 306 | N | Se | B78 | B14 |
| Compound 307 | N | Se | B79 | B14 |
| Compound 308 | N | Se | B80 | B14 |
| Compound 309 | N | Se | B82 | B14 |
| Compound 310 | N | Se | B83 | B14 |
| Compound 311 | N | Se | B85 | B14 |
| Compound 312 | N | Se | B88 | B14 |
| Compound 313 | N | A1 | B1 | B68 |
| Compound 314 | N | A1 | B6 | B68 |
| Compound 315 | N | A1 | B5 | B68 |
| Compound 316 | N | A1 | B10 | B68 |
| Compound 317 | N | A1 | B9 | B68 |
| Compound 318 | N | A1 | B14 | B68 |
| Compound 319 | N | A1 | B13 | B68 |
| Compound 320 | N | A1 | B18 | B68 |
| Compound 321 | N | A1 | B17 | B68 |
| Compound 322 | N | A1 | B22 | B68 |
| Compound 323 | N | A1 | B21 | B68 |
| Compound 324 | N | A1 | B26 | B68 |
| Compound 325 | N | A1 | B25 | B68 |
| Compound 326 | N | A1 | B30 | B68 |
| Compound 327 | N | A1 | B29 | B68 |
| Compound 328 | N | A1 | B34 | B68 |
| Compound 329 | N | A1 | B33 | B68 |
| Compound 330 | N | A1 | B38 | B68 |
| Compound 331 | N | A1 | B37 | B68 |
| Compound 332 | N | A1 | B42 | B68 |
| Compound 333 | N | A1 | B41 | B68 |
| Compound 334 | N | A1 | B49 | B68 |
| Compound 335 | N | A1 | B45 | B68 |
| Compound 336 | N | A1 | B56 | B68 |
| Compound 337 | N | A1 | B49 | B68 |
| Compound 338 | N | A1 | B63 | B68 |
| Compound 339 | N | A1 | B55 | B68 |
| Compound 340 | N | A1 | B70 | B68 |
| Compound 341 | N | A1 | B61 | B68 |
| Compound 342 | N | A1 | B72 | B68 |
| Compound 343 | N | A1 | B67 | B68 |
| Compound 344 | N | A1 | B82 | B68 |
| Compound 345 | N | A1 | B73 | B68 |
| Compound 346 | N | A1 | B84 | B68 |
| Compound 347 | N | A1 | B79 | B68 |
| Compound 348 | N | A1 | B88 | B68 |
| Compound 349 | N | A1 | B70 | B89 |
| Compound 350 | N | A1 | B70 | B2 |
| Compound 351 | N | A1 | B70 | B3 |
| Compound 352 | N | A1 | B70 | B4 |
| Compound 353 | N | A1 | B70 | B5 |
| Compound 354 | N | A1 | B70 | B89 |
| Compound 355 | N | A1 | B70 | B90 |
| Compound 356 | N | A1 | B70 | B91 |
| Compound 357 | N | A1 | B70 | B92 |
| Compound 358 | N | A1 | B70 | B93 |
| Compound 359 | N | A1 | B70 | B94 |
| Compound 360 | N | A1 | B70 | B12 |
| Compound 361 | N | A1 | B70 | B95 |
| Compound 362 | N | A1 | B70 | B100 |
| Compound 363 | N | A1 | B70 | B15 |
| Compound 364 | N | A1 | B70 | B16 |
| Compound 365 | N | A1 | B70 | B17 |
| Compound 366 | N | A1 | B70 | B18 |
| Compound 367 | N | A1 | B70 | B19 |
| Compound 368 | N | A1 | B70 | B20 |
| Compound 369 | N | A1 | B70 | B21 |
| Compound 370 | N | A1 | B70 | B22 |
| Compound 371 | N | A1 | B70 | B23 |
| Compound 372 | N | A1 | B70 | B24 |
| Compound 373 | N | A1 | B70 | B25 |
| Compound 374 | N | A1 | B70 | B26 |
| Compound 375 | N | A1 | B70 | B27 |
| Compound 376 | N | A1 | B70 | B28 |
| Compound 377 | N | A1 | B70 | B29 |
| Compound 378 | N | A1 | B70 | B30 |
| Compound 379 | N | A1 | B70 | B31 |
| Compound 380 | N | A1 | B70 | B32 |
| Compound 381 | N | A1 | B70 | B33 |
| Compound 382 | N | A1 | B70 | B34 |
| Compound 383 | N | A1 | B70 | B35 |
| Compound 384 | N | A1 | B70 | B36 |
| Compound 385 | N | A1 | B70 | B37 |
| Compound 386 | N | A1 | B70 | B38 |
| Compound 387 | N | A1 | B70 | B39 |
| Compound 388 | N | A1 | B70 | B40 |
| Compound 389 | N | A1 | B70 | B41 |
| Compound 390 | N | A1 | B70 | B42 |
| Compound 391 | N | A1 | B70 | B43 |
| Compound 392 | N | A1 | B70 | B44 |
| Compound 393 | N | A1 | B70 | B45 |
| Compound 394 | N | A1 | B70 | B46 |
| Compound 395 | N | A1 | B70 | B47 |
| Compound 396 | N | A1 | B70 | B48 |
| Compound 397 | N | A1 | B70 | B49 |

| No. | $Z_1 = Z_2$ | X = Y | R | $R_N$ |
|---|---|---|---|---|
| Compound 398 | N | A1 | B70 | B50 |
| Compound 399 | N | A1 | B70 | B51 |
| Compound 400 | N | A1 | B70 | B52 |
| Compound 401 | N | A1 | B70 | B53 |
| Compound 402 | N | A1 | B70 | B54 |
| Compound 403 | N | A1 | B70 | B55 |
| Compound 404 | N | A1 | B70 | B56 |
| Compound 405 | N | A1 | B70 | B57 |
| Compound 406 | N | A1 | B70 | B58 |
| Compound 407 | N | A1 | B70 | B59 |
| Compound 408 | N | A1 | B70 | B60 |
| Compound 409 | N | A1 | B70 | B61 |
| Compound 410 | N | A1 | B70 | B62 |
| Compound 411 | N | A1 | B70 | B63 |
| Compound 412 | N | A1 | B70 | B64 |
| Compound 413 | N | A1 | B70 | B65 |
| Compound 414 | N | A1 | B70 | B66 |
| Compound 415 | N | A1 | B70 | B67 |
| Compound 416 | N | A1 | B70 | B68 |
| Compound 417 | N | A1 | B70 | B69 |
| Compound 418 | N | A1 | B70 | B70 |
| Compound 419 | N | A1 | B70 | B71 |
| Compound 420 | N | A1 | B70 | B72 |
| Compound 421 | N | A1 | B70 | B73 |
| Compound 422 | N | A1 | B70 | B74 |
| Compound 423 | N | A1 | B70 | B75 |
| Compound 424 | N | A1 | B70 | B76 |
| Compound 425 | N | A1 | B70 | B77 |
| Compound 426 | N | A1 | B70 | B78 |
| Compound 427 | N | A1 | B70 | B79 |
| Compound 428 | N | A1 | B70 | B80 |
| Compound 429 | N | A1 | B70 | B81 |
| Compound 430 | N | A1 | B70 | B82 |
| Compound 431 | N | A1 | B70 | B83 |
| Compound 432 | N | A1 | B70 | B84 |
| Compound 433 | N | A1 | B70 | B96 |
| Compound 434 | N | A1 | B70 | B97 |
| Compound 435 | N | A1 | B70 | B98 |
| Compound 436 | N | A1 | B70 | B99 |
| Compound 437 | N | A1 | B68 | B89 |
| Compound 438 | N | A1 | B68 | B15 |
| Compound 439 | N | A1 | B68 | B18 |
| Compound 440 | N | A1 | B68 | B20 |
| Compound 441 | N | A1 | B68 | B22 |
| Compound 442 | N | A1 | B68 | B25 |
| Compound 443 | N | A1 | B68 | B26 |
| Compound 444 | N | A1 | B68 | B30 |
| Compound 445 | N | A1 | B68 | B30 |
| Compound 446 | N | A1 | B68 | B38 |
| Compound 447 | N | A1 | B68 | B36 |
| Compound 448 | N | A1 | B68 | B46 |
| Compound 449 | N | A1 | B68 | B42 |
| Compound 450 | N | A1 | B68 | B55 |
| Compound 451 | N | A1 | B68 | B48 |
| Compound 452 | N | A1 | B68 | B62 |
| Compound 453 | N | A1 | B68 | B54 |
| Compound 454 | N | A1 | B68 | B69 |
| Compound 455 | N | A1 | B68 | B60 |
| Compound 456 | N | A1 | B68 | B73 |
| Compound 457 | N | A1 | B68 | B66 |
| Compound 458 | N | A1 | B68 | B77 |
| Compound 459 | N | A1 | B68 | B72 |
| Compound 460 | N | A1 | B68 | B81 |
| Compound 461 | N | A1 | B68 | B78 |
| Compound 462 | N | A1 | B68 | B90 |
| Compound 463 | N | A1 | B68 | B84 |
| Compound 464 | N | A1 | B68 | B91 |
| Compound 465 | CH | A1 | B1 | B14 |
| Compound 466 | CH | A1 | B2 | B14 |
| Compound 467 | CH | A1 | B3 | B14 |
| Compound 468 | CH | A1 | B4 | B14 |
| Compound 469 | CH | A1 | B5 | B14 |
| Compound 470 | CH | A1 | B6 | B14 |
| Compound 471 | CH | A1 | B7 | B14 |
| Compound 472 | CH | A1 | B8 | B14 |
| Compound 473 | CH | A1 | B9 | B14 |
| Compound 474 | CH | A1 | B10 | B14 |
| Compound 475 | CH | A1 | B11 | B14 |
| Compound 476 | CH | A1 | B12 | B14 |
| Compound 477 | CH | A1 | B13 | B14 |
| Compound 478 | CH | A1 | B14 | B14 |
| Compound 479 | CH | A1 | B15 | B14 |
| Compound 480 | CH | A1 | B16 | B14 |
| Compound 481 | CH | A1 | B17 | B14 |
| Compound 482 | CH | A1 | B18 | B14 |
| Compound 483 | CH | A1 | B19 | B14 |
| Compound 484 | CH | A1 | B20 | B14 |
| Compound 485 | CH | A1 | B21 | B14 |
| Compound 486 | CH | A1 | B22 | B14 |
| Compound 487 | CH | A1 | B23 | B14 |
| Compound 488 | CH | A1 | B24 | B14 |
| Compound 489 | CH | A1 | B25 | B14 |
| Compound 490 | CH | A1 | B26 | B14 |
| Compound 491 | CH | A1 | B27 | B14 |
| Compound 492 | CH | A1 | B28 | B14 |
| Compound 493 | CH | A1 | B29 | B14 |
| Compound 494 | CH | A1 | B30 | B14 |
| Compound 495 | CH | A1 | B31 | B14 |
| Compound 496 | CH | A1 | B32 | B14 |
| Compound 497 | CH | A1 | B33 | B14 |
| Compound 498 | CH | A1 | B34 | B14 |
| Compound 499 | CH | A1 | B35 | B14 |
| Compound 500 | CH | A1 | B36 | B14 |
| Compound 501 | CH | A1 | B37 | B14 |
| Compound 502 | CH | A1 | B38 | B14 |
| Compound 503 | CH | A1 | B39 | B14 |
| Compound 504 | CH | A1 | B40 | B14 |
| Compound 505 | CH | A1 | B41 | B14 |
| Compound 506 | CH | A1 | B42 | B14 |
| Compound 507 | CH | A1 | B43 | B14 |
| Compound 508 | CH | A1 | B44 | B14 |
| Compound 509 | CH | A1 | B45 | B14 |
| Compound 510 | CH | A1 | B46 | B14 |
| Compound 511 | CH | A1 | B47 | B14 |
| Compound 512 | CH | A1 | B48 | B14 |
| Compound 513 | CH | A1 | B49 | B14 |
| Compound 514 | CH | A1 | B50 | B14 |
| Compound 515 | CH | A1 | B51 | B14 |
| Compound 516 | CH | A1 | B52 | B14 |
| Compound 517 | CH | A1 | B53 | B14 |
| Compound 518 | CH | A1 | B54 | B14 |
| Compound 519 | CH | A1 | B55 | B14 |
| Compound 520 | CH | A1 | B56 | B14 |
| Compound 521 | CH | A1 | B57 | B14 |
| Compound 522 | CH | A1 | B58 | B14 |
| Compound 523 | CH | A1 | B59 | B14 |
| Compound 524 | CH | A1 | B60 | B14 |
| Compound 525 | CH | A1 | B61 | B14 |
| Compound 526 | CH | A1 | B62 | B14 |
| Compound 527 | CH | A1 | B63 | B14 |
| Compound 528 | CH | A1 | B64 | B14 |
| Compound 529 | CH | A1 | B65 | B14 |
| Compound 530 | CH | A1 | B66 | B14 |
| Compound 531 | CH | A1 | B67 | B14 |
| Compound 532 | CH | A1 | B68 | B14 |
| Compound 533 | CH | A1 | B69 | B14 |
| Compound 534 | CH | A1 | B70 | B14 |
| Compound 535 | CH | A1 | B71 | B14 |
| Compound 536 | CH | A1 | B72 | B14 |
| Compound 537 | CH | A1 | B73 | B14 |
| Compound 538 | CH | A1 | B74 | B14 |
| Compound 539 | CH | A1 | B75 | B14 |
| Compound 540 | CH | A1 | B76 | B14 |
| Compound 541 | CH | A1 | B77 | B14 |
| Compound 542 | CH | A1 | B78 | B14 |
| Compound 543 | CH | A1 | B79 | B14 |
| Compound 544 | CH | A1 | B80 | B14 |
| Compound 545 | CH | A1 | B81 | B14 |
| Compound 546 | CH | A1 | B82 | B14 |
| Compound 547 | CH | A1 | B83 | B14 |
| Compound 548 | CH | A1 | B84 | B14 |
| Compound 549 | CH | A1 | B85 | B14 |
| Compound 550 | CH | A1 | B86 | B14 |
| Compound 551 | CH | A1 | B87 | B14 |

| No. | $Z_1 = Z_2$ | X = Y | R | $R_N$ |
|---|---|---|---|---|
| Compound 552 | CH | A1 | B88 | B14 |
| Compound 553 | CH | A2 | B1 | B14 |
| Compound 554 | CH | A2 | B6 | B14 |
| Compound 555 | CH | A2 | B12 | B14 |
| Compound 556 | CH | A2 | B14 | B14 |
| Compound 557 | CH | A2 | B20 | B14 |
| Compound 558 | CH | A2 | B28 | B14 |
| Compound 559 | CH | A2 | B30 | B14 |
| Compound 560 | CH | A2 | B35 | B14 |
| Compound 561 | CH | A2 | B38 | B14 |
| Compound 562 | CH | A2 | B39 | B14 |
| Compound 563 | CH | A2 | B41 | B14 |
| Compound 564 | CH | A2 | B42 | B14 |
| Compound 565 | CH | A2 | B49 | B14 |
| Compound 566 | CH | A2 | B54 | B14 |
| Compound 567 | CH | A2 | B56 | B14 |
| Compound 568 | CH | A2 | B64 | B14 |
| Compound 569 | CH | A2 | B68 | B14 |
| Compound 570 | CH | A2 | B69 | B14 |
| Compound 571 | CH | A2 | B70 | B14 |
| Compound 572 | CH | A2 | B72 | B14 |
| Compound 573 | CH | A2 | B75 | B14 |
| Compound 574 | CH | A2 | B78 | B14 |
| Compound 575 | CH | A2 | B79 | B14 |
| Compound 576 | CH | A2 | B80 | B14 |
| Compound 577 | CH | A2 | B82 | B14 |
| Compound 578 | CH | A2 | B83 | B14 |
| Compound 579 | CH | A2 | B85 | B14 |
| Compound 580 | CH | A2 | B88 | B14 |
| Compound 581 | CH | A3 | B1 | B14 |
| Compound 582 | CH | A3 | B6 | B14 |
| Compound 583 | CH | A3 | B12 | B14 |
| Compound 584 | CH | A3 | B14 | B14 |
| Compound 585 | CH | A3 | B20 | B14 |
| Compound 586 | CH | A3 | B28 | B14 |
| Compound 587 | CH | A3 | B30 | B14 |
| Compound 588 | CH | A3 | B35 | B14 |
| Compound 589 | CH | A3 | B38 | B14 |
| Compound 590 | CH | A3 | B39 | B14 |
| Compound 591 | CH | A3 | B41 | B14 |
| Compound 592 | CH | A3 | B42 | B14 |
| Compound 593 | CH | A3 | B49 | B14 |
| Compound 594 | CH | A3 | B54 | B14 |
| Compound 595 | CH | A3 | B56 | B14 |
| Compound 596 | CH | A3 | B64 | B14 |
| Compound 597 | CH | A3 | B68 | B14 |
| Compound 598 | CH | A3 | B69 | B14 |
| Compound 599 | CH | A3 | B70 | B14 |
| Compound 600 | CH | A3 | B72 | B14 |
| Compound 601 | CH | A3 | B75 | B14 |
| Compound 602 | CH | A3 | B78 | B14 |
| Compound 603 | CH | A3 | B79 | B14 |
| Compound 604 | CH | A3 | B80 | B14 |
| Compound 605 | CH | A3 | B82 | B14 |
| Compound 606 | CH | A3 | B83 | B14 |
| Compound 607 | CH | A3 | B85 | B14 |
| Compound 608 | CH | A3 | B88 | B14 |
| Compound 609 | CH | A4 | B1 | B14 |
| Compound 610 | CH | A4 | B6 | B14 |
| Compound 611 | CH | A4 | B12 | B14 |
| Compound 612 | CH | A4 | B14 | B14 |
| Compound 613 | CH | A4 | B20 | B14 |
| Compound 614 | CH | A4 | B28 | B14 |
| Compound 615 | CH | A4 | B30 | B14 |
| Compound 616 | CH | A4 | B35 | B14 |
| Compound 617 | CH | A4 | B38 | B14 |
| Compound 618 | CH | A4 | B39 | B14 |
| Compound 619 | CH | A4 | B41 | B14 |
| Compound 620 | CH | A4 | B42 | B14 |
| Compound 621 | CH | A4 | B49 | B14 |
| Compound 622 | CH | A4 | B54 | B14 |
| Compound 623 | CH | A4 | B56 | B14 |
| Compound 624 | CH | A4 | B64 | B14 |
| Compound 625 | CH | A4 | B68 | B14 |
| Compound 626 | CH | A4 | B69 | B14 |
| Compound 627 | CH | A4 | B70 | B14 |
| Compound 628 | CH | A4 | B72 | B14 |
| Compound 629 | CH | A4 | B75 | B14 |
| Compound 630 | CH | A4 | B78 | B14 |
| Compound 631 | CH | A4 | B79 | B14 |
| Compound 632 | CH | A4 | B80 | B14 |
| Compound 633 | CH | A4 | B82 | B14 |
| Compound 634 | CH | A4 | B83 | B14 |
| Compound 635 | CH | A4 | B85 | B14 |
| Compound 636 | CH | A4 | B88 | B14 |
| Compound 637 | CH | A5 | B1 | B14 |
| Compound 638 | CH | A5 | B6 | B14 |
| Compound 639 | CH | A5 | B12 | B14 |
| Compound 640 | CH | A5 | B14 | B14 |
| Compound 641 | CH | A5 | B20 | B14 |
| Compound 642 | CH | A5 | B28 | B14 |
| Compound 643 | CH | A5 | B30 | B14 |
| Compound 644 | CH | A5 | B35 | B14 |
| Compound 645 | CH | A5 | B38 | B14 |
| Compound 646 | CH | A5 | B39 | B14 |
| Compound 647 | CH | A5 | B41 | B14 |
| Compound 648 | CH | A5 | B42 | B14 |
| Compound 649 | CH | A5 | B49 | B14 |
| Compound 650 | CH | A5 | B54 | B14 |
| Compound 651 | CH | A5 | B56 | B14 |
| Compound 652 | CH | A5 | B64 | B14 |
| Compound 653 | CH | A5 | B68 | B14 |
| Compound 654 | CH | A5 | B69 | B14 |
| Compound 655 | CH | A5 | B70 | B14 |
| Compound 656 | CH | A5 | B72 | B14 |
| Compound 657 | CH | A5 | B75 | B14 |
| Compound 658 | CH | A5 | B78 | B14 |
| Compound 659 | CH | A5 | B79 | B14 |
| Compound 660 | CH | A5 | B80 | B14 |
| Compound 661 | CH | A5 | B82 | B14 |
| Compound 662 | CH | A5 | B83 | B14 |
| Compound 663 | CH | A5 | B85 | B14 |
| Compound 664 | CH | A5 | B88 | B14 |
| Compound 665 | CH | A6 | B1 | B14 |
| Compound 666 | CH | A6 | B6 | B14 |
| Compound 667 | CH | A6 | B12 | B14 |
| Compound 668 | CH | A6 | B14 | B14 |
| Compound 669 | CH | A6 | B20 | B14 |
| Compound 670 | CH | A6 | B28 | B14 |
| Compound 671 | CH | A6 | B30 | B14 |
| Compound 672 | CH | A6 | B35 | B14 |
| Compound 673 | CH | A6 | B38 | B14 |
| Compound 674 | CH | A6 | B39 | B14 |
| Compound 675 | CH | A6 | B41 | B14 |
| Compound 676 | CH | A6 | B42 | B14 |
| Compound 677 | CH | A6 | B49 | B14 |
| Compound 678 | CH | A6 | B54 | B14 |
| Compound 679 | CH | A6 | B56 | B14 |
| Compound 680 | CH | A6 | B64 | B14 |
| Compound 681 | CH | A6 | B68 | B14 |
| Compound 682 | CH | A6 | B69 | B14 |
| Compound 683 | CH | A6 | B70 | B14 |
| Compound 684 | CH | A6 | B72 | B14 |
| Compound 685 | CH | A6 | B75 | B14 |
| Compound 686 | CH | A6 | B78 | B14 |
| Compound 687 | CH | A6 | B79 | B14 |
| Compound 688 | CH | A6 | B80 | B14 |
| Compound 689 | CH | A6 | B82 | B14 |
| Compound 690 | CH | A6 | B83 | B14 |
| Compound 691 | CH | A6 | B85 | B14 |
| Compound 692 | CH | A6 | B88 | B14 |
| Compound 693 | CH | A7 | B1 | B14 |
| Compound 694 | CH | A7 | B6 | B14 |
| Compound 695 | CH | A7 | B12 | B14 |
| Compound 696 | CH | A7 | B14 | B14 |
| Compound 697 | CH | A7 | B20 | B14 |
| Compound 698 | CH | A7 | B28 | B14 |
| Compound 699 | CH | A7 | B30 | B14 |
| Compound 700 | CH | A7 | B35 | B14 |
| Compound 701 | CH | A7 | B38 | B14 |
| Compound 702 | CH | A7 | B39 | B14 |
| Compound 703 | CH | A7 | B41 | B14 |
| Compound 704 | CH | A7 | B42 | B14 |
| Compound 705 | CH | A7 | B49 | B14 |

| No. | $Z_1 = Z_2$ | X = Y | R | $R_N$ |
|---|---|---|---|---|
| Compound 706 | CH | A7 | B54 | B14 |
| Compound 707 | CH | A7 | B56 | B14 |
| Compound 708 | CH | A7 | B64 | B14 |
| Compound 709 | CH | A7 | B68 | B14 |
| Compound 710 | CH | A7 | B69 | B14 |
| Compound 711 | CH | A7 | B70 | B14 |
| Compound 712 | CH | A7 | B72 | B14 |
| Compound 713 | CH | A7 | B75 | B14 |
| Compound 714 | CH | A7 | B78 | B14 |
| Compound 715 | CH | A7 | B79 | B14 |
| Compound 716 | CH | A7 | B80 | B14 |
| Compound 717 | CH | A7 | B82 | B14 |
| Compound 718 | CH | A7 | B83 | B14 |
| Compound 719 | CH | A7 | B85 | B14 |
| Compound 720 | CH | A7 | B88 | B14 |
| Compound 721 | CH | S | B1 | B14 |
| Compound 722 | CH | S | B6 | B14 |
| Compound 723 | CH | S | B12 | B14 |
| Compound 724 | CH | S | B2 | B14 |
| Compound 725 | CH | S | B20 | B14 |
| Compound 726 | CH | S | B28 | B14 |
| Compound 727 | CH | S | B30 | B14 |
| Compound 728 | CH | S | B35 | B14 |
| Compound 729 | CH | S | B38 | B14 |
| Compound 730 | CH | S | B39 | B14 |
| Compound 731 | CH | S | B41 | B14 |
| Compound 732 | CH | S | B42 | B14 |
| Compound 733 | CH | S | B49 | B14 |
| Compound 734 | CH | S | B54 | B14 |
| Compound 735 | CH | S | B56 | B14 |
| Compound 736 | CH | S | B64 | B14 |
| Compound 737 | CH | S | B68 | B14 |
| Compound 738 | CH | S | B69 | B14 |
| Compound 739 | CH | S | B70 | B14 |
| Compound 740 | CH | S | B72 | B14 |
| Compound 741 | CH | S | B75 | B14 |
| Compound 742 | CH | S | B78 | B14 |
| Compound 743 | CH | S | B79 | B14 |
| Compound 744 | CH | S | B80 | B14 |
| Compound 745 | CH | S | B82 | B14 |
| Compound 746 | CH | S | B83 | B14 |
| Compound 747 | CH | S | B85 | B14 |
| Compound 748 | CH | S | B88 | B14 |
| Compound 749 | CH | Se | B1 | B14 |
| Compound 750 | CH | Se | B6 | B14 |
| Compound 751 | CH | Se | B12 | B14 |
| Compound 752 | CH | Se | B2 | B14 |
| Compound 753 | CH | Se | B20 | B14 |
| Compound 754 | CH | Se | B28 | B14 |
| Compound 755 | CH | Se | B30 | B14 |
| Compound 756 | CH | Se | B35 | B14 |
| Compound 757 | CH | Se | B38 | B14 |
| Compound 758 | CH | Se | B39 | B14 |
| Compound 759 | CH | Se | B41 | B14 |
| Compound 760 | CH | Se | B42 | B14 |
| Compound 761 | CH | Se | B49 | B14 |
| Compound 762 | CH | Se | B54 | B14 |
| Compound 763 | CH | Se | B56 | B14 |
| Compound 764 | CH | Se | B64 | B14 |
| Compound 765 | CH | Se | B68 | B14 |
| Compound 766 | CH | Se | B69 | B14 |
| Compound 767 | CH | Se | B70 | B14 |
| Compound 768 | CH | Se | B72 | B14 |
| Compound 769 | CH | Se | B75 | B14 |
| Compound 770 | CH | Se | B78 | B14 |
| Compound 771 | CH | Se | B79 | B14 |
| Compound 772 | CH | Se | B80 | B14 |
| Compound 773 | CH | Se | B82 | B14 |
| Compound 774 | CH | Se | B83 | B14 |
| Compound 775 | CH | Se | B85 | B14 |
| Compound 776 | CH | Se | B88 | B14 |
| Compound 777 | CH | A1 | B1 | B16 |
| Compound 778 | CH | A1 | B6 | B16 |
| Compound 779 | CH | A1 | B5 | B16 |
| Compound 780 | CH | A1 | B10 | B16 |
| Compound 781 | CH | A1 | B9 | B16 |
| Compound 782 | CH | A1 | B14 | B16 |
| Compound 783 | CH | A1 | B13 | B16 |
| Compound 784 | CH | A1 | B18 | B16 |
| Compound 785 | CH | A1 | B17 | B16 |
| Compound 786 | CH | A1 | B22 | B16 |
| Compound 787 | CH | A1 | B21 | B16 |
| Compound 788 | CH | A1 | B26 | B16 |
| Compound 789 | CH | A1 | B25 | B16 |
| Compound 790 | CH | A1 | B30 | B16 |
| Compound 791 | CH | A1 | B29 | B16 |
| Compound 792 | CH | A1 | B34 | B16 |
| Compound 793 | CH | A1 | B33 | B16 |
| Compound 794 | CH | A1 | B38 | B16 |
| Compound 795 | CH | A1 | B37 | B16 |
| Compound 796 | CH | A1 | B42 | B16 |
| Compound 797 | CH | A1 | B41 | B16 |
| Compound 798 | CH | A1 | B49 | B16 |
| Compound 799 | CH | A1 | B45 | B16 |
| Compound 800 | CH | A1 | B56 | B16 |
| Compound 801 | CH | A1 | B49 | B16 |
| Compound 802 | CH | A1 | B63 | B16 |
| Compound 803 | CH | A1 | B55 | B164 |
| Compound 804 | CH | A1 | B70 | B16 |
| Compound 805 | CH | A1 | B61 | B16 |
| Compound 806 | CH | A1 | B72 | B16 |
| Compound 807 | CH | A1 | B67 | B16 |
| Compound 808 | CH | A1 | B82 | B16 |
| Compound 809 | CH | A1 | B73 | B16 |
| Compound 810 | CH | A1 | B84 | B16 |
| Compound 811 | CH | A1 | B79 | B16 |
| Compound 812 | CH | A1 | B88 | B16 |
| Compound 813 | CH | A1 | B70 | B89 |
| Compound 814 | CH | A1 | B70 | B2 |
| Compound 815 | CH | A1 | B70 | B3 |
| Compound 816 | CH | A1 | B70 | B4 |
| Compound 817 | CH | A1 | B70 | B5 |
| Compound 818 | CH | A1 | B70 | B90 |
| Compound 819 | CH | A1 | B70 | B91 |
| Compound 820 | CH | A1 | B70 | B92 |
| Compound 821 | CH | A1 | B70 | B93 |
| Compound 822 | CH | A1 | B70 | B94 |
| Compound 823 | CH | A1 | B70 | B95 |
| Compound 824 | CH | A1 | B70 | B12 |
| Compound 825 | CH | A1 | B70 | B96 |
| Compound 826 | CH | A1 | B70 | B97 |
| Compound 827 | CH | A1 | B70 | B15 |
| Compound 828 | CH | A1 | B70 | B16 |
| Compound 829 | CH | A1 | B70 | B17 |
| Compound 830 | CH | A1 | B70 | B18 |
| Compound 831 | CH | A1 | B70 | B19 |
| Compound 832 | CH | A1 | B70 | B20 |
| Compound 833 | CH | A1 | B70 | B21 |
| Compound 834 | CH | A1 | B70 | B22 |
| Compound 835 | CH | A1 | B70 | B23 |
| Compound 836 | CH | A1 | B70 | B24 |
| Compound 837 | CH | A1 | B70 | B25 |
| Compound 838 | CH | A1 | B70 | B26 |
| Compound 839 | CH | A1 | B70 | B27 |
| Compound 840 | CH | A1 | B70 | B28 |
| Compound 841 | CH | A1 | B70 | B29 |
| Compound 842 | CH | A1 | B70 | B30 |
| Compound 843 | CH | A1 | B70 | B31 |
| Compound 844 | CH | A1 | B70 | B32 |
| Compound 845 | CH | A1 | B70 | B33 |
| Compound 846 | CH | A1 | B70 | B34 |
| Compound 847 | CH | A1 | B70 | B35 |
| Compound 848 | CH | A1 | B70 | B36 |
| Compound 849 | CH | A1 | B70 | B37 |
| Compound 850 | CH | A1 | B70 | B38 |
| Compound 851 | CH | A1 | B70 | B39 |
| Compound 852 | CH | A1 | B70 | B40 |
| Compound 853 | CH | A1 | B70 | B41 |
| Compound 854 | CH | A1 | B70 | B42 |
| Compound 855 | CH | A1 | B70 | B43 |
| Compound 856 | CH | A1 | B70 | B44 |
| Compound 857 | CH | A1 | B70 | B45 |
| Compound 858 | CH | A1 | B70 | B46 |
| Compound 859 | CH | A1 | B70 | B47 |

| No. | $Z_1 = Z_2$ | X = Y | R | $R_N$ |
|---|---|---|---|---|
| Compound 860 | CH | A1 | B70 | B48 |
| Compound 861 | CH | A1 | B70 | B49 |
| Compound 862 | CH | A1 | B70 | B50 |
| Compound 863 | CH | A1 | B70 | B51 |
| Compound 864 | CH | A1 | B70 | B52 |
| Compound 865 | CH | A1 | B70 | B53 |
| Compound 866 | CH | A1 | B70 | B54 |
| Compound 867 | CH | A1 | B70 | B55 |
| Compound 868 | CH | A1 | B70 | B56 |
| Compound 869 | CH | A1 | B70 | B57 |
| Compound 870 | CH | A1 | B70 | B58 |
| Compound 871 | CH | A1 | B70 | B59 |
| Compound 872 | CH | A1 | B70 | B60 |
| Compound 873 | CH | A1 | B70 | B61 |
| Compound 874 | CH | A1 | B70 | B62 |
| Compound 875 | CH | A1 | B70 | B63 |
| Compound 876 | CH | A1 | B70 | B64 |
| Compound 877 | CH | A1 | B70 | B65 |
| Compound 878 | CH | A1 | B70 | B66 |
| Compound 879 | CH | A1 | B70 | B67 |
| Compound 880 | CH | A1 | B70 | B68 |
| Compound 881 | CH | A1 | B70 | B69 |
| Compound 882 | CH | A1 | B70 | B70 |
| Compound 883 | CH | A1 | B70 | B71 |
| Compound 884 | CH | A1 | B70 | B72 |
| Compound 885 | CH | A1 | B70 | B73 |
| Compound 886 | CH | A1 | B70 | B74 |
| Compound 887 | CH | A1 | B70 | B75 |
| Compound 888 | CH | A1 | B70 | B76 |
| Compound 889 | CH | A1 | B70 | B77 |
| Compound 890 | CH | A1 | B70 | B78 |
| Compound 891 | CH | A1 | B70 | B79 |
| Compound 892 | CH | A1 | B70 | B80 |
| Compound 893 | CH | A1 | B70 | B81 |
| Compound 894 | CH | A1 | B70 | B82 |
| Compound 895 | CH | A1 | B70 | B83 |
| Compound 896 | CH | A1 | B70 | B84 |
| Compound 897 | CH | A1 | B70 | B98 |
| Compound 898 | CH | A1 | B70 | B99 |
| Compound 899 | CH | A1 | B70 | B100 |
| Compound 900 | CH | A1 | B70 | B101 |
| Compound 901 | CH | A1 | B68 | B89 |
| Compound 902 | CH | A1 | B68 | B15 |
| Compound 903 | CH | A1 | B68 | B18 |
| Compound 904 | CH | A1 | B68 | B20 |
| Compound 905 | CH | A1 | B68 | B22 |
| Compound 906 | CH | A1 | B68 | B25 |
| Compound 907 | CH | A1 | B68 | B26 |
| Compound 908 | CH | A1 | B68 | B30 |
| Compound 909 | CH | A1 | B68 | B30 |
| Compound 910 | CH | A1 | B68 | B38 |
| Compound 911 | CH | A1 | B68 | B36 |
| Compound 912 | CH | A1 | B68 | B46 |
| Compound 913 | CH | A1 | B68 | B42 |
| Compound 914 | CH | A1 | B68 | B55 |
| Compound 915 | CH | A1 | B68 | B48 |
| Compound 916 | CH | A1 | B68 | B62 |
| Compound 917 | CH | A1 | B68 | B54 |
| Compound 918 | CH | A1 | B68 | B69 |
| Compound 919 | CH | A1 | B68 | B60 |
| Compound 920 | CH | A1 | B68 | B73 |
| Compound 921 | CH | A1 | B68 | B66 |
| Compound 922 | CH | A1 | B68 | B77 |
| Compound 923 | CH | A1 | B68 | B72 |
| Compound 924 | CH | A1 | B68 | B81 |
| Compound 925 | CH | A1 | B68 | B78 |
| Compound 926 | CH | A1 | B68 | B99 |
| Compound 927 | CH | A1 | B68 | B84 |
| Compound 928 | CH | A1 | B68 | B100 |
| Compound 929 | N | A1 | B1 | B16 |
| Compound 930 | N | A1 | B2 | B16 |
| Compound 931 | N | A1 | B3 | B16 |
| Compound 932 | N | A1 | B4 | B16 |
| Compound 933 | N | A1 | B5 | B16 |
| Compound 934 | N | A1 | B6 | B16 |
| Compound 935 | N | A1 | B7 | B16 |
| Compound 936 | N | A1 | B8 | B16 |
| Compound 937 | N | A1 | B9 | B16 |
| Compound 938 | N | A1 | B10 | B16 |
| Compound 939 | N | A1 | B11 | B16 |
| Compound 940 | N | A1 | B12 | B16 |
| Compound 941 | N | A1 | B22 | B16 |
| Compound 942 | N | A1 | B25 | B16 |
| Compound 943 | N | A1 | B26 | B16 |
| Compound 944 | N | A1 | B27 | B16 |
| Compound 945 | N | A1 | B28 | B16 |
| Compound 946 | N | A1 | B29 | B16 |
| Compound 947 | N | A1 | B30 | B16 |
| Compound 948 | N | A1 | B31 | B16 |
| Compound 949 | N | A1 | B38 | B16 |
| Compound 950 | N | A1 | B39 | B16 |
| Compound 951 | N | A1 | B41 | B16 |
| Compound 952 | N | A1 | B42 | B16 |
| Compound 953 | N | A1 | B43 | B16 |
| Compound 954 | N | A1 | B52 | B16 |
| Compound 955 | N | A1 | B67 | B16 |
| Compound 956 | N | A1 | B68 | B16 |
| Compound 957 | N | A1 | B69 | B16 |
| Compound 958 | N | A1 | B72 | B16 |
| Compound 959 | N | A1 | B74 | B16 |
| Compound 960 | N | A1 | B81 | B16 |
| Compound 961 | N | A1 | B82 | B16 |
| Compound 962 | N | A1 | B83 | B16 |
| Compound 963 | N | A1 | B84 | B16 |
| Compound 964 | N | A1 | B85 | B16 |
| Compound 965 | N | A1 | B89 | B14 |
| Compound 966 | N | A1 | B90 | B14 |
| Compound 967 | N | A1 | B91 | B14 |
| Compound 968 | N | A1 | B92 | B14 |
| Compound 969 | N | A1 | B93 | B14 |
| Compound 970 | N | A1 | B94 | B14 |
| Compound 971 | N | A1 | B95 | B14 |
| Compound 972 | N | A1 | B96 | B14 |
| Compound 973 | N | A1 | B97 | B14 |
| Compound 974 | N | A1 | B98 | B14 |
| Compound 975 | N | A1 | B99 | B14 |
| Compound 976 | N | A1 | B100 | B14 |
| Compound 977 | N | A1 | B101 | B14 |
| Compound 978 | N | A1 | B102 | B14 |
| Compound 979 | N | A1 | B103 | B14 |
| Compound 980 | N | A1 | B104 | B14 |
| Compound 981 | N | A1 | B105 | B14 |
| Compound 982 | N | A1 | B106 | B14 |
| Compound 983 | N | A1 | B107 | B14 |
| Compound 984 | N | A1 | B108 | B14 |
| Compound 985 | CH | A1 | B89 | B14 |
| Compound 986 | CH | A1 | B90 | B14 |
| Compound 987 | CH | A1 | B91 | B14 |
| Compound 988 | N | A1 | B56 | B16 |
| Compound 989 | N | A1 | B68 | B16 |
| Compound 990 | N | A1 | B70 | B16 |
| Compound 1003 | N | A1 | B13 | B16 |
| Compound 1004 | N | A1 | B13 | B17 |
| Compound 1005 | N | A1 | B13 | B18 |
| Compound 1006 | N | A1 | B13 | B19 |
| Compound 1007 | N | A1 | B13 | B25 |
| Compound 1008 | N | A1 | B13 | B29 |
| Compound 1009 | N | A1 | B13 | B30 |
| Compound 1010 | N | A1 | B13 | B38 |
| Compound 1011 | N | A1 | B13 | B39 |
| Compound 1012 | N | A1 | B13 | B55 |
| Compound 1013 | N | A1 | B13 | B68 |
| Compound 1014 | N | A1 | B13 | B92 |
| Compound 1015 | N | A1 | B13 | B96 |
| Compound 1016 | N | A1 | B13 | B103 | wherein, when $X_1$ and $X_2$ are N, wherein $Z_1$, $Z_2$, X, Y, and $R_N$ are correspondingly selected from the atoms or groups as shown in the following table, and the Compound 991 to Compound 1002 are:

| No. | $Z_1 = Z_2$ | X = Y | $R_N$ | No. | $Z_1 = Z_2$ | X = Y | $R_N$ |
|---|---|---|---|---|---|---|---|
| Compound 991 | N | A1 | B25 | Compound 992 | N | A1 | B26 |
| Compound 993 | N | A1 | B28 | Compound 994 | N | A1 | B30 |
| Compound 995 | N | A1 | B31 | Compound 996 | N | A1 | B39 |
| Compound 997 | N | A1 | B41 | Compound 998 | N | A1 | B42 |
| Compound 999 | N | A1 | B43 | Compound 1000 | N | A1 | B52 |
| Compound 1001 | N | A1 | B68 | Compound 1002 | N | A1 | B72 |

In the present embodiment, the compound has the structure of Formula 1, when $X_1$ and $X_2$ are CR, each R of $X_1$ and $X_2$ is identical, and that is, to Compound 1 to Compound 990 and Compound 1003 to Compound 1016, the choice of R listed in the table represents the choice of R of $X_1$ and $X_2$ at the same time. For example, to Compound 1, $Z_1$ and $Z_2$ are both N, X and Y are both structure A1, R of $X_1$ and $X_2$ are both B1, that is, the positions of $X_1$ and $X_2$ in the structure of Formula 1 are both C—B1, $R_N$ are both B14, and then the structure of Compound 1 is

as the same, for another example, to Compound 468, $Z_1$ and $Z_2$ are both CH, X and Y are both structure A1, R of $X_1$ and $X_2$ are both B4, that is, the positions of $X_1$ and $X_2$ in the structure of Formula 1 are both C—B4, $R_N$ are both B14, and then the structure of Compound 468 is

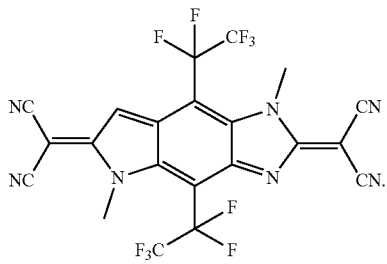 [SMILES: Cn1c(=C(C#N)C#N)cc2c(C(F)(F)C(F)(F)F)c3c(nc(=C(C#N)C#N)n3C)c(C(F)(F)C(F)(F)F)c21]

In the present embodiment, when $X_1$ and $X_2$ is N, that is, the positions in Compound 991 to Compound 1002 corresponding to $X_1$ and $X_2$ in the structure of Formula 1 are both N, and there is no R substituents in Compound 991 to Compound 1002.

According to an embodiment of the present disclosure, an electroluminescent device is also disclosed, which comprises:
 an anode,
 a cathode, and
 an organic layer disposed between the anode and the cathode, wherein the organic layer comprises a compound having Formula 1:

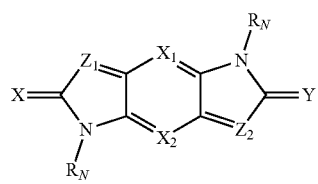

wherein
$X_1$ and $X_2$ are each independently selected from the group consisting of CR and N;
X and Y are each independently selected from the group consisting of O, S, Se, NR' and CR"R'";
$Z_1$ and $Z_2$ are each independently selected from the group consisting of CR and N; when $Z_1$ and $Z_2$ are both CR, at least one of X and Y is selected from the group consisting of S, Se, NR', and CR"R'";
$R_N$, is at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
R, R', R", and R'" are, in each instance the same or different, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof; wherein at least one of R, R', R" and R'" is a group having at least one electron-withdrawing group;

Any adjacent R, R', R" and R'" substituents may be optionally joined to form a ring.

In the present embodiment, the expression that any adjacent R, R', R" and R'" substituents may be optionally joined to form a ring is intended to mean that any two adjacent substituents of R, R', R" and R'", for example, between two R, between R and R', between R and R", between R' and R", between R and R'", and between R" and R'", any one or more of them may be optionally joined to form a ring. Obviously, any adjacent R, R', R" and R'" substituents may not be joined to form a ring.

According to an embodiment of the present disclosure, in the device, the organic layer is a hole injection layer or a hole transporting layer, and the hole injection layer or the hole transporting layer are formed from a compound of Formula 1 alone.

According to an embodiment of the present disclosure, in the device, the organic layer is a hole injection layer or a hole transporting layer, and the hole injection layer or the hole transporting layer further comprise at least one hole transporting material; and wherein the molar doping ratio of the compound of Formula 1 to the hole transporting material is from 10000:1 to 1:10000.

According to an embodiment of the present disclosure, the organic layer is a hole injection layer or a hole transporting layer, and the hole injection layer or the hole transporting layer further comprise at least one hole transporting material, wherein the molar doping ratio of the compound of Formula 1 to the hole transporting material is from 10:1 to 1:100.

According to an embodiment of the present disclosure, the hole injection layer or the hole transporting layer further comprise at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

According to an embodiment of the present disclosure, the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer;

wherein the organic layer comprising a compound having Formula 1 is the p-type charge generation layer; preferably, the p-type charge generation layer further comprises at least one hole transporting material, wherein the molar doping ratio of the compound of Formula 1 to the hole transporting material is from 10000:1 to 1:10000.

According to an embodiment of the present disclosure, in the p-type charge generation layer, the molar doping ratio of the compound of Formula 1 to the hole transporting material is from 10:1 to 1:100.

According to an embodiment of the present disclosure, wherein the p-type charge generation layer is formed by doping the compound of Formula 1 with at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

According to an embodiment of the present disclosure, the charge generation layer further includes a buffer layer disposed between the p-type charge generation layer and the n-type charge generation layer, wherein the buffer layer comprises a compound of Formula 1.

According to an embodiment of the present disclosure, the fabrication method of the electroluminescent device shown in any of the foregoing embodiments is vacuum deposition method.

According to another embodiment of the present disclosure, a compound formulation is also disclosed, which comprises a compound represented by Formula 1. The specific structure of the compound is shown in any of the foregoing embodiments.

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, materials disclosed herein may be used in combination with a wide variety of emitters, hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, the materials can be synthesized according to known literature synthesis methods, for example, US20190181349A1 or by methods well known to the persons skilled in the art. Synthetic products can be structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) As the persons skilled in the art are aware of the aforementioned equipment's use, test methods and other related contents, the inherent data of the sample can be obtained with certainty and without influence, so the above related contents are not further described in this patent.

In one embodiment, the LUMO values of selected disclosure compounds are obtained by DFT calculation [GAUSS-09, B3LYP/6-311G(d)] and shown in the following table. The result shows that the materials have deep LUMO levels, suitable for applications as hole injection materials and/or p-dopants with hole transporting materials such as but not limited to arylamine type hole transporting materials.

| Compound No. | Structure of the compounds | LUMO (eV) |
|---|---|---|
| 1 | | −5.19 |
| 4 | | −5.34 |
| 6 | | −5.55 |
| 52 | | −5.18 |
| 55 | | −5.04 |
| 56 | | −4.93 |

-continued

| Compound No. | Structure of the compounds | LUMO (eV) |
|---|---|---|
| 68 | | −5.21 |
| 468 | | −4.82 |
| 470 | | −5.03 |
| 965 | | −5.43 |
| 966 | | −5.1 |
| 985 | | −4.88 |
| 1001 | | −5.46 |
| 1003 | | −4.74 |

In order to further prove the deep LUMO property of the compounds disclosed in the present disclosure, Compound 1003 was synthesized and its LUMO energy level was measured.

Material Synthesis Example

The method for preparing a compound in the present disclosure is not limited herein. Typically, the following compounds are taken as examples without limitations, and synthesis routes and preparation methods thereof are described below.

Synthesis Example 1: Synthesis of Compound 1003

Step 1: Synthesis of Intermediate 1-a

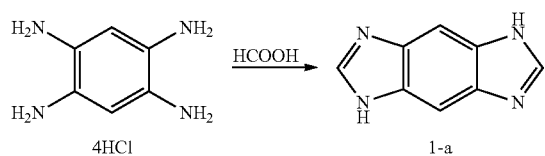 [SMILES: Nc1cc(N)c(N)cc1N ; "HCOOH" ; c1nc2cc3[nH]cnc3cc2[nH]1]

22 g of 1,2,4,5-benzenetetraamine tetrahydrochloride was dissolved in 500 mL of formic acid, the mixture was heated to reflux and reacted for 24 h. After the completion of the reaction, the solvent was removed via rotatory evaporation directly to afford a black solid. The solid was dissolved in 300 mL of water, filtered. The filtrate was neutralized with 10% aqueous solution of NaOH, and the pH was adjusted to about 7-8. There are a large amount of brown solid precipitated, filtered and dried to afford the intermediate 1-a (10.0 g, yield of 82%). $^1$HNMR (400 MHz, $d_6$-DMSO) δ=12.25 (s, 2H), 8.21 (s, 2H), 7.72 (s, 2H).

Step 2: Synthesis of Intermediate 1-b

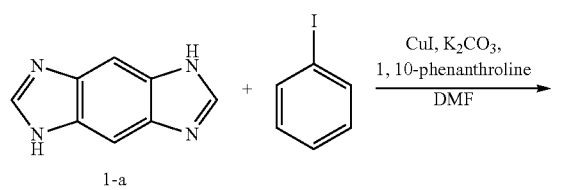

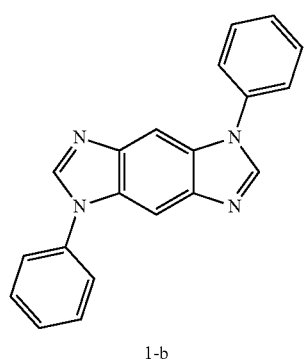

To a reaction flask, the intermediate 1-a (10.0 g, 63.3 mmol), CuI (1.55 g, 8.1 mmol), 1,10-phenanthroline (2.44 g, 13.5 mmol) and $K_2CO_3$ (35.6 g, 258 mmol) were added. DMF (320 mL) was added under the protection of nitrogen gas. The mixture was heated to 130° C. to react for 48 h. The reaction was monitored with LC-MS, and the solvent was removed via rotatory evaporation directly after the completion of the reaction. The residue was purified via silica gel column chromatography (DCM/$CH_3OH$=20/1, v/v) to afford the intermediate 1-b (3.8 g, yield of 19%) as a white solid. $^1$HNMR (400 MHz, $CDCl_3$) δ=8.20 (s, 2H), 8.00 (s, 2H), 7.62 (m, 8H), 7.49 (m, 2H).

Step 3: Synthesis of Intermediate 1-c

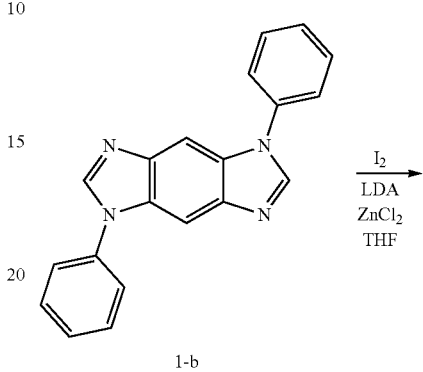

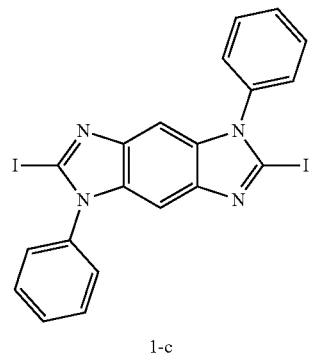

Under the nitrogen atmosphere, the intermediate 1-b (2.1 g, 6.8 mmol) was added to THF (150 mL), and was cooled to −72° C. (ethanol/dry ice cooling bath). To the mixture, the solution of LDA (20 mL, 2.0 M) was slowly added dropwisely. Then the mixture was slowly warmed to about −30° C. and reacted for 3 h. A solution of $ZnCl_2$ (20 mL, 2.0 M) was added dropwisely at −30° C. Then the reaction solution was slowly warmed to 0° C. and reacted for 15 min. $I_2$ (10.1 g) was added to the reaction solution, and reacted for 2 h at 0° C. After the completion, the reaction was quenched with saturated solution of $NH_4Cl$, washed with a saturated solution of sodium thiosulfate, extracted with DCM, dried and rotatory evaporated to remove the solvent. The residue was purified via silica column chromatography (DCM/THF=4/1, v/v) to afford the intermediate 1-c (3.8 g, yield of 19%) as a white solid. $^1$HNMR (400 MHz, $d_6$-DMSO) δ=7.69 (m, 6H), 7.56 (m, 4H), 7.28 (s, 2H).

Step 4: Synthesis of Intermediate 1-d

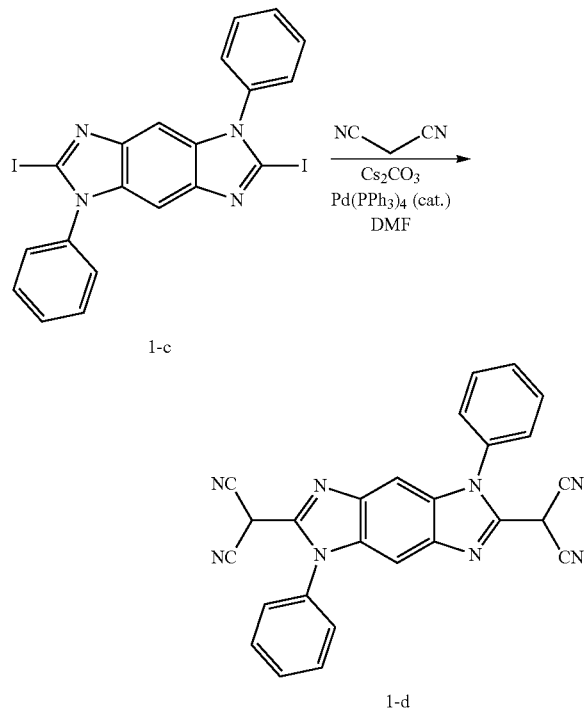

Under the nitrogen atmosphere, malononitrile (0.198 g, 3.0 mmol) was added to anhydrous DMF (15 mL). $Cs_2CO_3$ (0.980 g, 3.0 mmol) was added at 0° C., stirred for 20 min, then the intermediate 1-c (0.310 g, 1.0 mmol) and $Pd(PPh_3)_4$ (0.085 g, 0.07 mmol) were added, warmed to 90° C. and reacted for 24 h. After the total consumption of intermediate 1-c, the reaction mixture was poured into ice water. The pH was adjusted to <1 with 2 N dilute hydrochloric acid, a large amount of yellow solid precipitated, which were filtered, washed with small amount of water and petroleum ether. The solid product was dissolved with acetone, evaporated on a rotatory evaporator to remove the solvent, washed with dichloromethane for three times to afford intermediate 1-d (0.153 g, yield of 63%) as a light yellow solid.

Step 5: Synthesis of Compound 1003

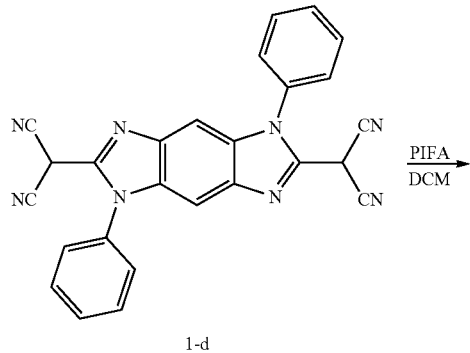

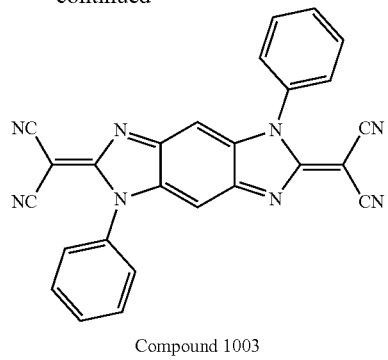

Compound 1003

Under the nitrogen atmosphere, intermediate 1-d (0.153 g) was added to DCM (100 mL), cooled to 0° C., PIFA ([Bis(trifluoroacetoxy)iodo]benzene, 0.308 g) was added portionwise, and then the mixture was stirred for 2 days at room temperature. The solution was purple black. Most of DCM was removed via rotatory evaporation, and a black solid was obtained after filtering. The solid was washed with mixed solvents of DCM/PE (1/1, v/v) twice, dried to give a black solid Compound 1003 (0.105 g, yield of 69%). The product is confirmed as the target product, with a molecular weight of 436.

The electrochemical property of the compounds of the present disclosure was tested via cyclic volammetry. The test uses the electrochemical workstation model CorrTest CS120 produced by WUHAN CORRTEST Instrument Co., Ltd., and used three electrode working system: platinum disk electrode as working electrode, $Ag/AgNO_3$ electrode as reference electrode, platinum wire electrode as auxiliary electrode. Using anhydrous DCM or anhydrous DMF as the solvent and 0.1 mol/L tetrabutylammonium hexafluorophosphate as the supporting electrolyte, the target compound was prepared into a 10-3 mol/L solution, and nitrogen gas was bubbled into the solution for 10 min deoxygenation before the test. Instrument parameter settings: the scan rate is 100 mV/s, the potential interval is 0.5 mV, and the test scope is from 1 V to −0.5 V.

The LUMO energy level of the Compound 1003 tested via the CV method in anhydrous DMF is −4.78 eV. And the LUMO energy level of the commercial hole injection layer material HATCN tested via the same CV method in anhydrous DMF is −4.20 eV. The structure of HATCN is shown as below:

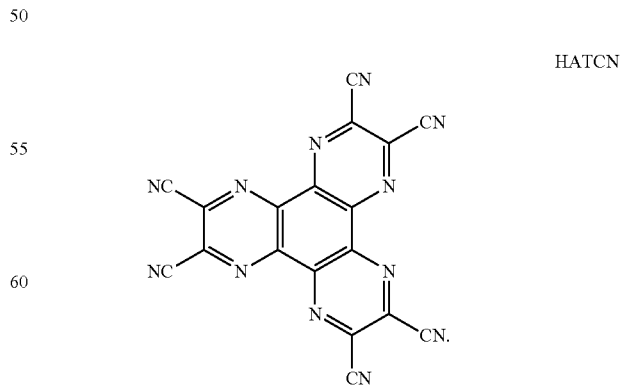

HATCN

Compared with the commercial hole injection layer material HATCN (LUMO=−4.20 eV), the Compound 1003 has deeper LUMO energy level, which shows that the Compound 1003 has better potential and excellent application prospect as the hole injection layer material in electroluminescent devices.

Compared with the LUMO energy level (−4.74 eV) calculated with DFT method, the difference between the calculation result and the tested result via CV of the Compound 1003 is very small. That means the LUMO energy level obtained via DFT method is very close to the real data and has high credibility. The DFT results of the compounds having the structure of Formula 1 show the desired deep LUMO performance of these compounds, and prove that these compounds are suitable for the application as charge transporting materials, charge injection materials or the like in electroluminescent devices.

It is understood that the various embodiments described herein are by way of example only, and are not intended to limit the scope of the disclosure. The present disclosure as claimed may therefore include variations from the particular examples and preferred embodiments described herein, as will be apparent to one of skill in the art. Many of the materials and structures described herein may be substituted with other materials and structures without deviating from the spirit of the disclosure. It is understood that various theories as to why the disclosure works are not intended to be limiting.

What is claimed is:

1. A compound having Formula 1:

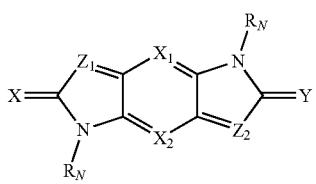

Formula 1 wherein $X_1$ and $X_2$ are each independently selected from the group consisting of CR and N;

X and Y are each independently selected from the group consisting of O, S, Se, NR' and CR"R'";

$Z_1$ and $Z_2$ are each independently selected from the group consisting of CR and N; and when $Z_1$ and $Z_2$ are both CR, at least one of X and Y is S, Se, NR', or CR"R'";

$R_N$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

R, R', R" and R'" are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

at least one of R, R', R" and R'" is a group having at least one electron-withdrawing group;

any adjacent R, R', R" and R'" substituents may be optionally joined to form a ring.

2. The compound of claim 1, wherein X and Y are each independently selected from the group consisting of S, Se, NR' and CR"R".

3. The compound of claim 2, wherein Ry is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof; preferably, wherein Ry is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, a substituted or unsubstituted heteroaryl group having 3 to 30 carbon atoms, and combinations thereof.

4. The compound of claim 1, wherein $Z_1$ and $Z_2$ are N.

5. The compound of claim 1, wherein $X_1$ and $X_2$ are CR; wherein R is, at each occurrence identically or differently, a group having at least one electron-withdrawing group.

6. The compound of claim 1, wherein X and Y are each independently selected from CR"R'" or NR'; wherein R', R" and R'" are, at each occurrence identically or differently, groups each having at least one electron-withdrawing group.

7. The compound of claim 6, wherein X and Y are CR"R'".

8. The compound of claim 1, wherein $X_1$ and $X_2$ are CR; wherein R is, at each occurrence identically or differently, a substituted or unsubstituted aryl group having 6 to 30 carbon atoms, a substituted or unsubstituted heteroaryl group having 3 to 30 carbon atoms, preferably, the aryl group and/or heteroaryl group is (are) substituted with at least one electron-withdrawing group.

9. The compound of claim 1, wherein $R_N$ is, at each occurrence identically or differently, selected from the group consisting of a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 carbon atoms, a substituted or unsubstituted heteroaryl group having 3 to 30 carbon atoms, and combinations thereof;
wherein Z and $Z_2$ are N;
wherein $X_1$ and $X_2$ are CR, wherein R is, at each occurrence identically or differently, a group having at least one electron-withdrawing group;
wherein X and Y are CR"R'", wherein R" and R'" are, at each occurrence identically or differently, groups each having at least one electron-withdrawing group.

10. The compound of claim 1, wherein the Hammett's constant of the electron-withdrawing group is ≥0.05, preferably ≥0.3, more preferably ≥0.5.

11. The compound of claim 1, wherein the electron-withdrawing group is selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxyl group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms and an arylsilyl group having 6 to 20 carbon atoms which is substituted with one or more of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and combinations thereof;
preferably, the electron-withdrawing group is selected from the group consisting of F, $CF_3$, $OCF_3$, $SF_5$, $SO_2CF_3$, cyano, isocyano, SCN, OCN, pyrimidinyl, triazinyl, and combinations thereof.

12. The compound of claim 1, wherein X and Y are each independently selected from the group consisting of:

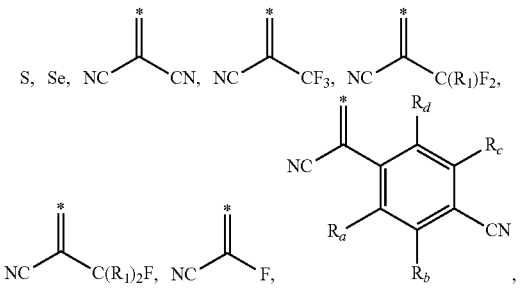

-continued

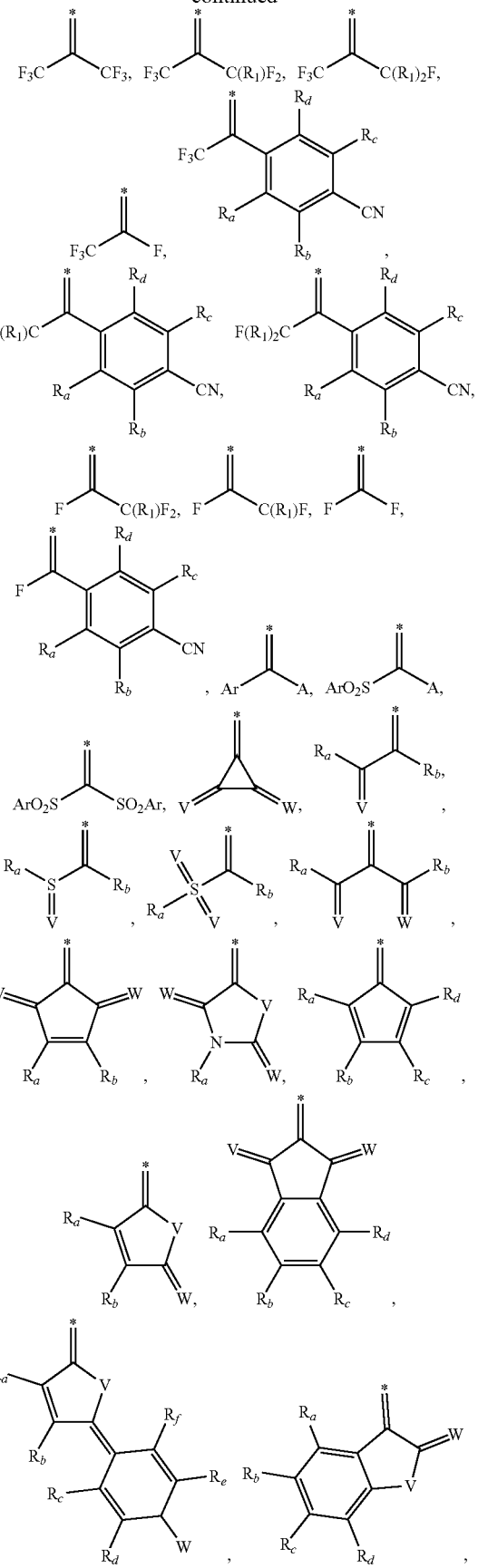

-continued

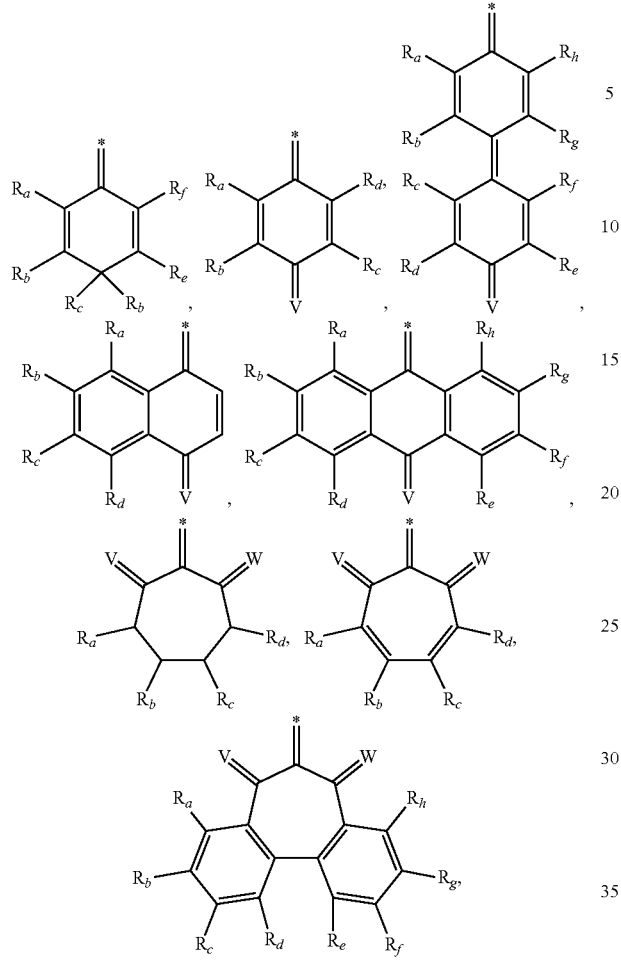

wherein $R_1$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

preferably, $R_1$ is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof;

wherein V and W are, at each occurrence identically or differently, selected from the group consisting of $CR_vR_w$, $NR_v$, O, S and Se;

wherein Ar is, at each occurrence identically or differently, selected from a substituted or unsubstituted aryl group having 6 to 30 carbon atoms, or a substituted or unsubstituted heteroaryl group having 3 to 30 carbon atoms;

wherein A, $R_a$, $R_b$, $R_c$, $R_d$, $R_e$, $R_f$, $R_g$, $R_h$, $R_v$ and $R_w$ are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein A is a group having at least one electron-withdrawing group, and for any one of the structures, when one or more of $R_a$, $R_b$, $R_c$, $R_d$, $R_e$, $R_f$, $R_g$, $R_h$, $R_v$ and $R_w$ is (are) present, at least one of $R_a$, $R_b$, $R_c$, $R_d$, $R_e$, $R_f$, $R_g$, $R_h$, $R_v$ and $R_w$ is a group having at least one electron-withdrawing group; preferably, the group having at least one electron-withdrawing group is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

13. The compound of claim 1, wherein X and Y are, at each occurrence identically or differently, selected from the group consisting of:

S, Se,

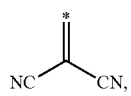

A1

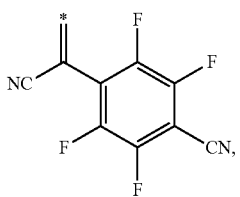

A2

-continued

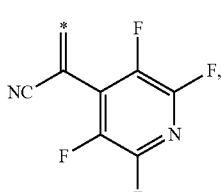

A3

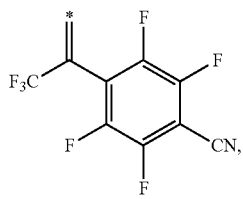

A4

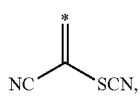

A5

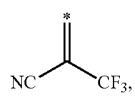

A6

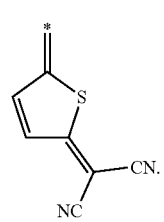

A7

14. The compound of claim 1, wherein each of R groups is, at each occurrence identically or differently, selected from the group consisting of hydrogen, deuterium, halogen, nitroso, nitro, acyl, carbonyl, a carboxylic acid group, an ester group, cyano, isocyano, SCN, OCN, SF$_5$, boranyl, sulfinyl, sulfonyl, phosphoroso, an unsubstituted alkyl group having 1 to 20 carbon atoms, an unsubstituted cycloalkyl group having 3 to 20 ring carbon atoms, an unsubstituted alkoxyl group having 1 to 20 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms and a heteroaryl group having 3 to 30 carbon atoms which is substituted with one or more groups selected from the group consisting of halogen, nitroso, nitro, acyl, carbonyl, a carboxylic acid group, an ester group, cyano, isocyano, SCN, OCN, SF$_5$, boranyl, sulfinyl, sulfonyl, phosphoroso, and combinations thereof;
preferably, each of R groups is, at each occurrence identically or differently, selected from the group consisting of hydrogen, deuterium, methyl, isopropyl, NO$_2$, SO$_2$CH$_3$, SCF$_3$, C$_2$F$_5$, OC$_2$F$_5$, OCH$_3$, diphenylmethylsilyl, phenyl, methoxyphenyl, p-methylphenyl, 2,6-diisopropylphenyl, biphenyl, polyfluorophenyl, difluoropyridyl, nitrophenyl, dimethylthiazolyl, CN, vinyl substituted with one or more of CN and CF$_3$, ethynyl substituted with one of CN and CF$_3$, dimethylphosphoroso, diphenylphosphoroso, F, CF$_3$, OCF$_3$, SF$_5$, SO$_2$CF$_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and CF$_3$, tetrafluoropyridyl, pyrimidinyl, triazinyl, pyridyl, diphenylboranyl, oxaboraanthryl, and combinations thereof.

15. The compound of claim 14, wherein X and Y are

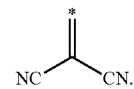

A1

16. The compound of claim 13, wherein R group is, at each occurrence identically or differently, selected from the group consisting of:

B1

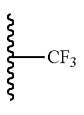

B2

B3

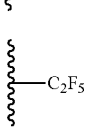

B4

B5

B6

B7

B8

B9

B10

B11 
B12 
B13 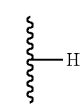
B14 
B15 
B16 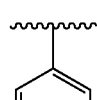
B17 
B18 
B19 
B20 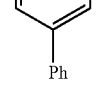
B21 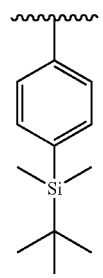
B22 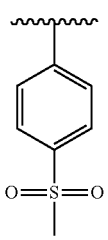
B23 
B24 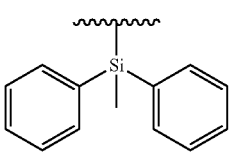
B25 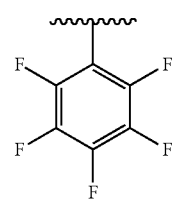
B26 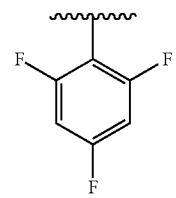
B27 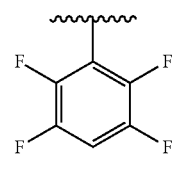
B28 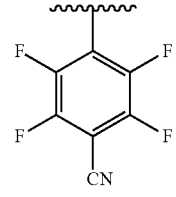

-continued
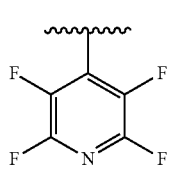 B29
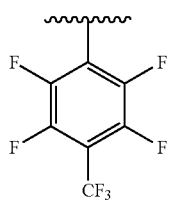 B30
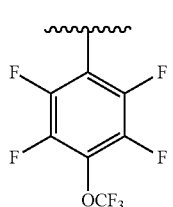 B31
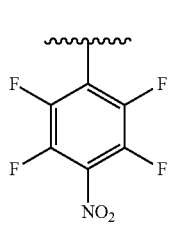 B32
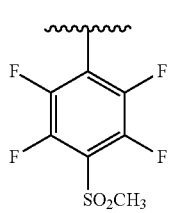 B33
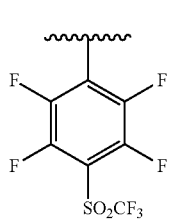 B34
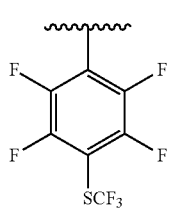 B35
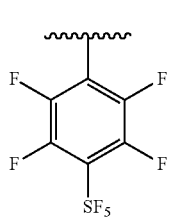 B36
-continued
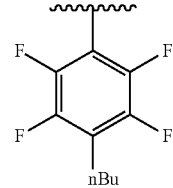 B37
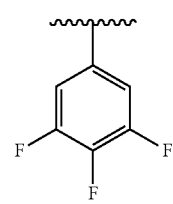 B38
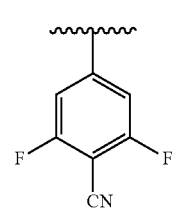 B39
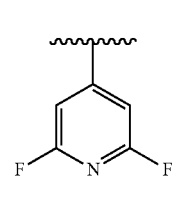 B40
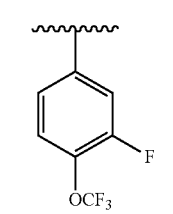 B41
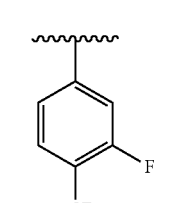 B42
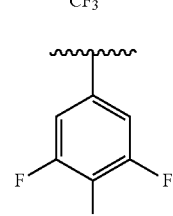 B43
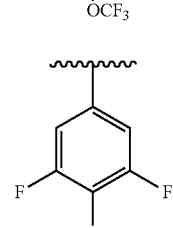 B44

-continued
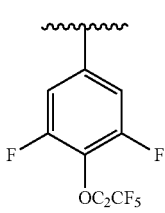
B45
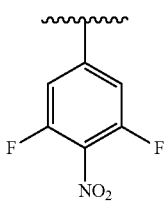
B46
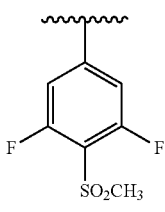
B47
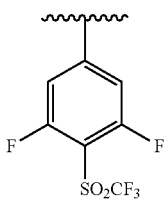
B48
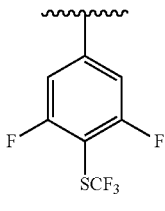
B49
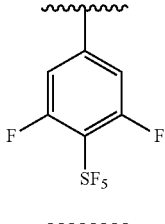
B50
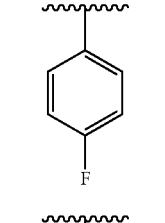
B51
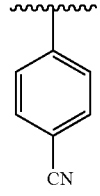
B52
-continued
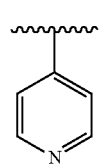
B53
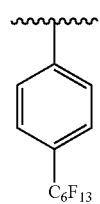
B54
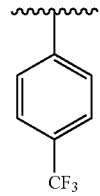
B55
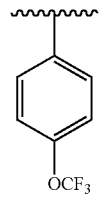
B56
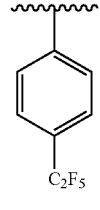
B57
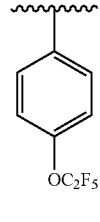
B58
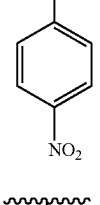
B59
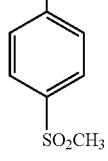
B60

B61 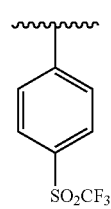
B62 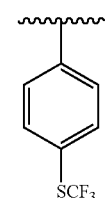
B63 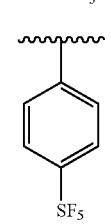
B64 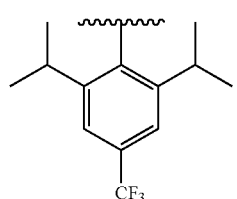
B65 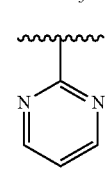
B66 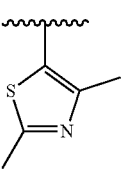
B67 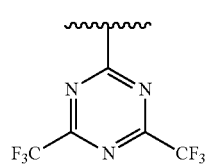
B68 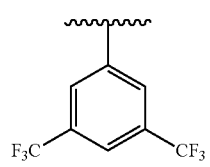
B69 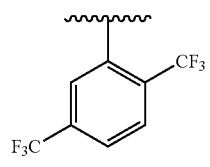
B70 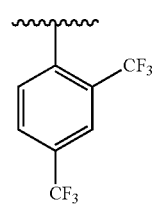
B71 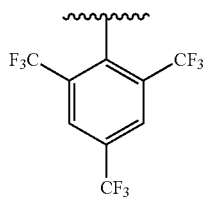
B72 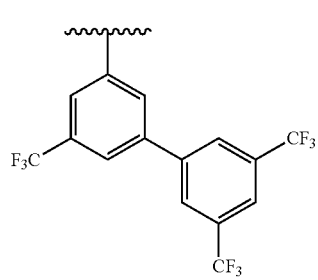
B73 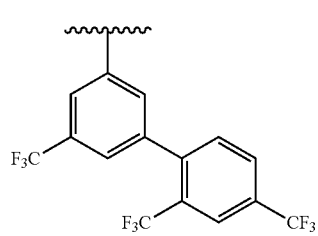
B74 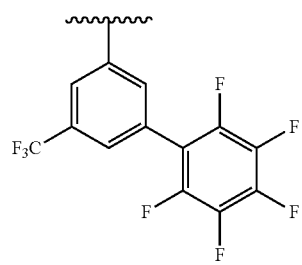
B75 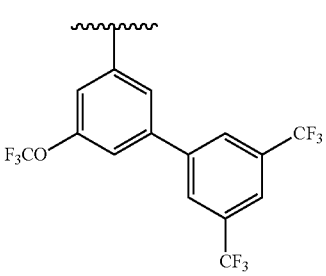

| | |
|---|---|
| B76 | B85 |
| B77 | B86 |
| B78 | B87 |
| B79 | B88 |
| B80 | B89 |
| B81 | B90 |
| B82 | B91 |
| B83 | B92 |
| B84 | B93 |
| | B94 |

-continued
B95 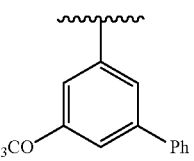
B96 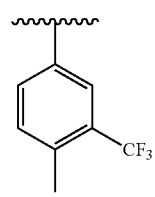
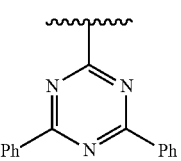 B103
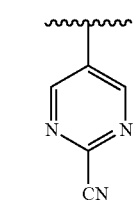 B104
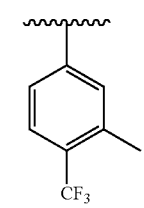 B97
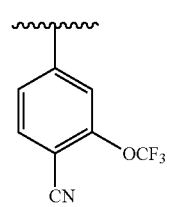 B105
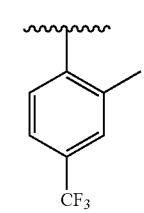 B98
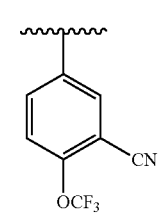 B106
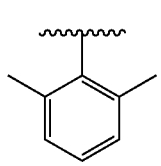 B99
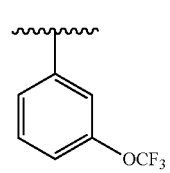 B107
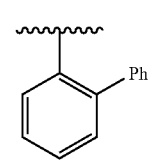 B100
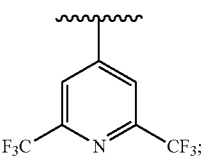 B108
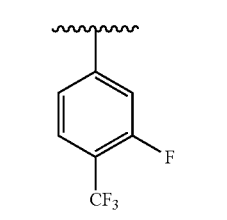 B101
B109
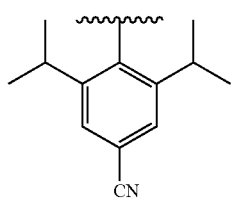
B102
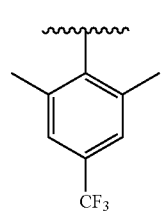
preferably, the two R groups are the same.
17. The compound of claim 16, wherein,
when $X_1$ and $X_2$ are CR, and each R of $X_1$ and $X_2$ is identical, wherein $Z_1$, $Z_2$, X, Y, each R of $X_1$ and $X_2$, and Ry are correspondingly selected from the atoms or groups as shown in the following table, and the Compound 1 to Compound 990 and Compound 1003 to Compound 1016 are:

| No. | $Z_1 = Z_2$ | $X = Y$ | R | $R_N$ | No. | $Z_1 = Z_2$ | $X = Y$ | R | $R_N$ |
|---|---|---|---|---|---|---|---|---|---|
| Compound 1 | N | A1 | B1 | B14 | Compound 2 | N | A1 | B2 | B14 |
| Compound 3 | N | A1 | B3 | B14 | Compound 4 | N | A1 | B4 | B14 |
| Compound 5 | N | A1 | B5 | B14 | Compound 6 | N | A1 | B6 | B14 |
| Compound 7 | N | A1 | B7 | B14 | Compound 8 | N | A1 | B8 | B14 |
| Compound 9 | N | A1 | B9 | B14 | Compound 10 | N | A1 | B10 | B14 |
| Compound 11 | N | A1 | B11 | B14 | Compound 12 | N | A1 | B12 | B14 |
| Compound 13 | N | A1 | B13 | B14 | Compound 14 | N | A1 | B14 | B14 |
| Compound 15 | N | A1 | B15 | B14 | Compound 16 | N | A1 | B16 | B14 |
| Compound 17 | N | A1 | B17 | B14 | Compound 18 | N | A1 | B18 | B14 |
| Compound 19 | N | A1 | B19 | B14 | Compound 20 | N | A1 | B20 | B14 |
| Compound 21 | N | A1 | B21 | B14 | Compound 22 | N | A1 | B22 | B14 |
| Compound 23 | N | A1 | B23 | B14 | Compound 24 | N | A1 | B24 | B14 |
| Compound 25 | N | A1 | B25 | B14 | Compound 26 | N | A1 | B26 | B14 |
| Compound 27 | N | A1 | B27 | B14 | Compound 28 | N | A1 | B28 | B14 |
| Compound 29 | N | A1 | B29 | B14 | Compound 30 | N | A1 | B30 | B14 |
| Compound 31 | N | A1 | B31 | B14 | Compound 32 | N | A1 | B32 | B14 |
| Compound 33 | N | A1 | B33 | B14 | Compound 34 | N | A1 | B34 | B14 |
| Compound 35 | N | A1 | B35 | B14 | Compound 36 | N | A1 | B36 | B14 |
| Compound 37 | N | A1 | B37 | B14 | Compound 38 | N | A1 | B38 | B14 |
| Compound 39 | N | A1 | B39 | B14 | Compound 40 | N | A1 | B40 | B14 |
| Compound 41 | N | A1 | B41 | B14 | Compound 42 | N | A1 | B42 | B14 |
| Compound 43 | N | A1 | B43 | B14 | Compound 44 | N | A1 | B44 | B14 |
| Compound 45 | N | A1 | B45 | B14 | Compound 46 | N | A1 | B46 | B14 |
| Compound 47 | N | A1 | B47 | B14 | Compound 48 | N | A1 | B48 | B14 |
| Compound 49 | N | A1 | B49 | B14 | Compound 50 | N | A1 | B50 | B14 |
| Compound 51 | N | A1 | B51 | B14 | Compound 52 | N | A1 | B52 | B14 |
| Compound 53 | N | A1 | B53 | B14 | Compound 54 | N | A1 | B54 | B14 |
| Compound 55 | N | A1 | B55 | B14 | Compound 56 | N | A1 | B56 | B14 |
| Compound 57 | N | A1 | B57 | B14 | Compound 58 | N | A1 | B58 | B14 |
| Compound 59 | N | A1 | B59 | B14 | Compound 60 | N | A1 | B60 | B14 |
| Compound 61 | N | A1 | B61 | B14 | Compound 62 | N | A1 | B62 | B14 |
| Compound 63 | N | A1 | B63 | B14 | Compound 64 | N | A1 | B64 | B14 |
| Compound 65 | N | A1 | B65 | B14 | Compound 66 | N | A1 | B66 | B14 |
| Compound 67 | N | A1 | B67 | B14 | Compound 68 | N | A1 | B68 | B14 |
| Compound 69 | N | A1 | B69 | B14 | Compound 70 | N | A1 | B70 | B14 |
| Compound 71 | N | A1 | B71 | B14 | Compound 72 | N | A1 | B72 | B14 |
| Compound 73 | N | A1 | B73 | B14 | Compound 74 | N | A1 | B74 | B14 |
| Compound 75 | N | A1 | B75 | B14 | Compound 76 | N | A1 | B76 | B14 |
| Compound 77 | N | A1 | B77 | B14 | Compound 78 | N | A1 | B78 | B14 |
| Compound 79 | N | A1 | B79 | B14 | Compound 80 | N | A1 | B80 | B14 |
| Compound 81 | N | A1 | B81 | B14 | Compound 82 | N | A1 | B82 | B14 |
| Compound 83 | N | A1 | B83 | B14 | Compound 84 | N | A1 | B84 | B14 |
| Compound 85 | N | A1 | B85 | B14 | Compound 86 | N | A1 | B86 | B14 |
| Compound 87 | N | A1 | B87 | B14 | Compound 88 | N | A1 | B88 | B14 |
| Compound 89 | N | A2 | B1 | B14 | Compound 90 | N | A2 | B6 | B14 |
| Compound 91 | N | A2 | B12 | B14 | Compound 92 | N | A2 | B14 | B14 |
| Compound 93 | N | A2 | B20 | B14 | Compound 94 | N | A2 | B28 | B14 |
| Compound 95 | N | A2 | B30 | B14 | Compound 96 | N | A2 | B35 | B14 |
| Compound 97 | N | A2 | B38 | B14 | Compound 98 | N | A2 | B39 | B14 |
| Compound 99 | N | A2 | B41 | B14 | Compound 100 | N | A2 | B42 | B14 |
| Compound 101 | N | A2 | B49 | B14 | Compound 102 | N | A2 | B54 | B14 |
| Compound 103 | N | A2 | B56 | B14 | Compound 104 | N | A2 | B64 | B14 |
| Compound 105 | N | A2 | B68 | B14 | Compound 106 | N | A2 | B69 | B14 |
| Compound 107 | N | A2 | B70 | B14 | Compound 108 | N | A2 | B72 | B14 |
| Compound 109 | N | A2 | B75 | B14 | Compound 110 | N | A2 | B78 | B14 |
| Compound 111 | N | A2 | B79 | B14 | Compound 112 | N | A2 | B80 | B14 |
| Compound 113 | N | A2 | B82 | B14 | Compound 114 | N | A2 | B83 | B14 |
| Compound 115 | N | A2 | B85 | B14 | Compound 116 | N | A2 | B88 | B14 |
| Compound 117 | N | A3 | B1 | B14 | Compound 118 | N | A3 | B6 | B14 |
| Compound 119 | N | A3 | B12 | B14 | Compound 120 | N | A3 | B14 | B14 |
| Compound 121 | N | A3 | B20 | B14 | Compound 122 | N | A3 | B28 | B14 |
| Compound 123 | N | A3 | B30 | B14 | Compound 124 | N | A3 | B35 | B14 |
| Compound 125 | N | A3 | B38 | B14 | Compound 126 | N | A3 | B39 | B14 |
| Compound 127 | N | A3 | B41 | B14 | Compound 128 | N | A3 | B42 | B14 |
| Compound 129 | N | A3 | B49 | B14 | Compound 130 | N | A3 | B54 | B14 |
| Compound 131 | N | A3 | B56 | B14 | Compound 132 | N | A3 | B64 | B14 |
| Compound 133 | N | A3 | B68 | B14 | Compound 134 | N | A3 | B69 | B14 |
| Compound 135 | N | A3 | B70 | B14 | Compound 136 | N | A3 | B72 | B14 |
| Compound 137 | N | A3 | B75 | B14 | Compound 138 | N | A3 | B78 | B14 |
| Compound 139 | N | A3 | B79 | B14 | Compound 140 | N | A3 | B80 | B14 |
| Compound 141 | N | A3 | B82 | B14 | Compound 142 | N | A3 | B83 | B14 |
| Compound 143 | N | A3 | B85 | B14 | Compound 144 | N | A3 | B88 | B14 |
| Compound 145 | N | A4 | B1 | B14 | Compound 146 | N | A4 | B6 | B14 |
| Compound 147 | N | A4 | B12 | B14 | Compound 148 | N | A4 | B14 | B14 |
| Compound 149 | N | A4 | B20 | B14 | Compound 150 | N | A4 | B28 | B14 |
| Compound 151 | N | A4 | B30 | B14 | Compound 152 | N | A4 | B35 | B14 |
| Compound 153 | N | A4 | B38 | B14 | Compound 154 | N | A4 | B39 | B14 |
| Compound 155 | N | A4 | B41 | B14 | Compound 156 | N | A4 | B42 | B14 |
| Compound 157 | N | A4 | B49 | B14 | Compound 158 | N | A4 | B54 | B14 |

-continued

| No. | $Z_1 = Z_2$ | $X = Y$ | R | $R_N$ | No. | $Z_1 = Z_2$ | $X = Y$ | R | $R_N$ |
|---|---|---|---|---|---|---|---|---|---|
| Compound 159 | N | A4 | B56 | B14 | Compound 160 | N | A4 | B64 | B14 |
| Compound 161 | N | A4 | B68 | B14 | Compound 162 | N | A4 | B69 | B14 |
| Compound 163 | N | A4 | B70 | B14 | Compound 164 | N | A4 | B72 | B14 |
| Compound 165 | N | A4 | B75 | B14 | Compound 166 | N | A4 | B78 | B14 |
| Compound 167 | N | A4 | B79 | B14 | Compound 168 | N | A4 | B80 | B14 |
| Compound 169 | N | A4 | B82 | B14 | Compound 170 | N | A4 | B83 | B14 |
| Compound 171 | N | A4 | B85 | B14 | Compound 172 | N | A4 | B88 | B14 |
| Compound 173 | N | A5 | B1 | B14 | Compound 174 | N | A5 | B6 | B14 |
| Compound 175 | N | A5 | B12 | B14 | Compound 176 | N | A5 | B14 | B14 |
| Compound 177 | N | A5 | B20 | B14 | Compound 178 | N | A5 | B28 | B14 |
| Compound 179 | N | A5 | B30 | B14 | Compound 180 | N | A5 | B35 | B14 |
| Compound 181 | N | A5 | B38 | B14 | Compound 182 | N | A5 | B39 | B14 |
| Compound 183 | N | A5 | B41 | B14 | Compound 184 | N | A5 | B42 | B14 |
| Compound 185 | N | A5 | B49 | B14 | Compound 186 | N | A5 | B54 | B14 |
| Compound 187 | N | A5 | B56 | B14 | Compound 188 | N | A5 | B64 | B14 |
| Compound 189 | N | A5 | B68 | B14 | Compound 190 | N | A5 | B69 | B14 |
| Compound 191 | N | A5 | B70 | B14 | Compound 192 | N | A5 | B72 | B14 |
| Compound 193 | N | A5 | B75 | B14 | Compound 194 | N | A5 | B78 | B14 |
| Compound 195 | N | A5 | B79 | B14 | Compound 196 | N | A5 | B80 | B14 |
| Compound 197 | N | A5 | B82 | B14 | Compound 198 | N | A5 | B83 | B14 |
| Compound 199 | N | A5 | B85 | B14 | Compound 200 | N | A5 | B88 | B14 |
| Compound 201 | N | A6 | B1 | B14 | Compound 202 | N | A6 | B6 | B14 |
| Compound 203 | N | A6 | B12 | B14 | Compound 204 | N | A6 | B14 | B14 |
| Compound 205 | N | A6 | B20 | B14 | Compound 206 | N | A6 | B28 | B14 |
| Compound 207 | N | A6 | B30 | B14 | Compound 208 | N | A6 | B35 | B14 |
| Compound 209 | N | A6 | B38 | B14 | Compound 210 | N | A6 | B39 | B14 |
| Compound 211 | N | A6 | B41 | B14 | Compound 212 | N | A6 | B42 | B14 |
| Compound 213 | N | A6 | B49 | B14 | Compound 214 | N | A6 | B54 | B14 |
| Compound 215 | N | A6 | B56 | B14 | Compound 216 | N | A6 | B64 | B14 |
| Compound 217 | N | A6 | B68 | B14 | Compound 218 | N | A6 | B69 | B14 |
| Compound 219 | N | A6 | B70 | B14 | Compound 220 | N | A6 | B72 | B14 |
| Compound 221 | N | A6 | B75 | B14 | Compound 222 | N | A6 | B78 | B14 |
| Compound 223 | N | A6 | B79 | B14 | Compound 224 | N | A6 | B80 | B14 |
| Compound 225 | N | A6 | B82 | B14 | Compound 226 | N | A6 | B83 | B14 |
| Compound 227 | N | A6 | B85 | B14 | Compound 228 | N | A6 | B88 | B14 |
| Compound 229 | N | A7 | B1 | B14 | Compound 230 | N | A7 | B6 | B14 |
| Compound 231 | N | A7 | B12 | B14 | Compound 232 | N | A7 | B14 | B14 |
| Compound 233 | N | A7 | B20 | B14 | Compound 234 | N | A7 | B28 | B14 |
| Compound 235 | N | A7 | B30 | B14 | Compound 236 | N | A7 | B35 | B14 |
| Compound 237 | N | A7 | B38 | B14 | Compound 238 | N | A7 | B39 | B14 |
| Compound 239 | N | A7 | B41 | B14 | Compound 240 | N | A7 | B42 | B14 |
| Compound 241 | N | A7 | B49 | B14 | Compound 242 | N | A7 | B54 | B14 |
| Compound 243 | N | A7 | B56 | B14 | Compound 244 | N | A7 | B64 | B14 |
| Compound 245 | N | A7 | B68 | B14 | Compound 246 | N | A7 | B69 | B14 |
| Compound 247 | N | A7 | B70 | B14 | Compound 248 | N | A7 | B72 | B14 |
| Compound 249 | N | A7 | B75 | B14 | Compound 250 | N | A7 | B78 | B14 |
| Compound 251 | N | A7 | B79 | B14 | Compound 252 | N | A7 | B80 | B14 |
| Compound 253 | N | A7 | B82 | B14 | Compound 254 | N | A7 | B83 | B14 |
| Compound 255 | N | A7 | B85 | B14 | Compound 256 | N | A7 | B88 | B14 |
| Compound 257 | N | S | B1 | B14 | Compound 258 | N | S | B6 | B14 |
| Compound 259 | N | S | B12 | B14 | Compound 260 | N | S | B2 | B14 |
| Compound 261 | N | S | B20 | B14 | Compound 262 | N | S | B28 | B14 |
| Compound 263 | N | S | B30 | B14 | Compound 264 | N | S | B35 | B14 |
| Compound 265 | N | S | B38 | B14 | Compound 266 | N | S | B39 | B14 |
| Compound 267 | N | S | B41 | B14 | Compound 268 | N | S | B42 | B14 |
| Compound 269 | N | S | B49 | B14 | Compound 270 | N | S | B54 | B14 |
| Compound 271 | N | S | B56 | B14 | Compound 272 | N | S | B64 | B14 |
| Compound 273 | N | S | B68 | B14 | Compound 274 | N | S | B69 | B14 |
| Compound 275 | N | S | B70 | B14 | Compound 276 | N | S | B72 | B14 |
| Compound 277 | N | S | B75 | B14 | Compound 278 | N | S | B78 | B14 |
| Compound 279 | N | S | B79 | B14 | Compound 280 | N | S | B80 | B14 |
| Compound 281 | N | S | B82 | B14 | Compound 282 | N | S | B83 | B14 |
| Compound 283 | N | S | B85 | B14 | Compound 284 | N | S | B88 | B14 |
| Compound 285 | N | Se | B1 | B14 | Compound 286 | N | Se | B6 | B14 |
| Compound 287 | N | Se | B12 | B14 | Compound 288 | N | Se | B2 | B14 |
| Compound 289 | N | Se | B20 | B14 | Compound 290 | N | Se | B28 | B14 |
| Compound 291 | N | Se | B30 | B14 | Compound 292 | N | Se | B35 | B14 |
| Compound 293 | N | Se | B38 | B14 | Compound 294 | N | Se | B39 | B14 |
| Compound 295 | N | Se | B41 | B14 | Compound 296 | N | Se | B42 | B14 |
| Compound 297 | N | Se | B49 | B14 | Compound 298 | N | Se | B54 | B14 |
| Compound 299 | N | Se | B56 | B14 | Compound 300 | N | Se | B64 | B14 |
| Compound 301 | N | Se | B68 | B14 | Compound 302 | N | Se | B69 | B14 |
| Compound 303 | N | Se | B70 | B14 | Compound 304 | N | Se | B72 | B14 |
| Compound 305 | N | Se | B75 | B14 | Compound 306 | N | Se | B78 | B14 |
| Compound 307 | N | Se | B79 | B14 | Compound 308 | N | Se | B80 | B14 |
| Compound 309 | N | Se | B82 | B14 | Compound 310 | N | Se | B83 | B14 |
| Compound 311 | N | Se | B85 | B14 | Compound 312 | N | Se | B88 | B14 |

-continued

| No. | $Z_1 = Z_2$ | X = Y | R | $R_N$ | No. | $Z_1 = Z_2$ | X = Y | R | $R_N$ |
|---|---|---|---|---|---|---|---|---|---|
| Compound 313 | N | A1 | B1 | B68 | Compound 314 | N | A1 | B6 | B68 |
| Compound 315 | N | A1 | B5 | B68 | Compound 316 | N | A1 | B10 | B68 |
| Compound 317 | N | A1 | B9 | B68 | Compound 318 | N | A1 | B14 | B68 |
| Compound 319 | N | A1 | B13 | B68 | Compound 320 | N | A1 | B18 | B68 |
| Compound 321 | N | A1 | B17 | B68 | Compound 322 | N | A1 | B22 | B68 |
| Compound 323 | N | A1 | B21 | B68 | Compound 324 | N | A1 | B26 | B68 |
| Compound 325 | N | A1 | B25 | B68 | Compound 326 | N | A1 | B30 | B68 |
| Compound 327 | N | A1 | B29 | B68 | Compound 328 | N | A1 | B34 | B68 |
| Compound 329 | N | A1 | B33 | B68 | Compound 330 | N | A1 | B38 | B68 |
| Compound 331 | N | A1 | B37 | B68 | Compound 332 | N | A1 | B42 | B68 |
| Compound 333 | N | A1 | B41 | B68 | Compound 334 | N | A1 | B49 | B68 |
| Compound 335 | N | A1 | B45 | B68 | Compound 336 | N | A1 | B56 | B68 |
| Compound 337 | N | A1 | B49 | B68 | Compound 338 | N | A1 | B63 | B68 |
| Compound 339 | N | A1 | B55 | B68 | Compound 340 | N | A1 | B70 | B68 |
| Compound 341 | N | A1 | B61 | B68 | Compound 342 | N | A1 | B72 | B68 |
| Compound 343 | N | A1 | B67 | B68 | Compound 344 | N | A1 | B82 | B68 |
| Compound 345 | N | A1 | B73 | B68 | Compound 346 | N | A1 | B84 | B68 |
| Compound 347 | N | A1 | B79 | B68 | Compound 348 | N | A1 | B88 | B68 |
| Compound 349 | N | A1 | B70 | B89 | Compound 350 | N | A1 | B70 | B2 |
| Compound 351 | N | A1 | B70 | B3 | Compound 352 | N | A1 | B70 | B4 |
| Compound 353 | N | A1 | B70 | B5 | Compound 354 | N | A1 | B70 | B89 |
| Compound 355 | N | A1 | B70 | B90 | Compound 356 | N | A1 | B70 | B91 |
| Compound 357 | N | A1 | B70 | B92 | Compound 358 | N | A1 | B70 | B93 |
| Compound 359 | N | A1 | B70 | B94 | Compound 360 | N | A1 | B70 | B12 |
| Compound 361 | N | A1 | B70 | B95 | Compound 362 | N | A1 | B70 | B100 |
| Compound 363 | N | A1 | B70 | B15 | Compound 364 | N | A1 | B70 | B16 |
| Compound 365 | N | A1 | B70 | B17 | Compound 366 | N | A1 | B70 | B18 |
| Compound 367 | N | A1 | B70 | B19 | Compound 368 | N | A1 | B70 | B20 |
| Compound 369 | N | A1 | B70 | B21 | Compound 370 | N | A1 | B70 | B22 |
| Compound 371 | N | A1 | B70 | B23 | Compound 372 | N | A1 | B70 | B24 |
| Compound 373 | N | A1 | B70 | B25 | Compound 374 | N | A1 | B70 | B26 |
| Compound 375 | N | A1 | B70 | B27 | Compound 376 | N | A1 | B70 | B28 |
| Compound 377 | N | A1 | B70 | B29 | Compound 378 | N | A1 | B70 | B30 |
| Compound 379 | N | A1 | B70 | B31 | Compound 380 | N | A1 | B70 | B32 |
| Compound 381 | N | A1 | B70 | B33 | Compound 382 | N | A1 | B70 | B34 |
| Compound 383 | N | A1 | B70 | B35 | Compound 384 | N | A1 | B70 | B36 |
| Compound 385 | N | A1 | B70 | B37 | Compound 386 | N | A1 | B70 | B38 |
| Compound 387 | N | A1 | B70 | B39 | Compound 388 | N | A1 | B70 | B40 |
| Compound 389 | N | A1 | B70 | B41 | Compound 390 | N | A1 | B70 | B42 |
| Compound 391 | N | A1 | B70 | B43 | Compound 392 | N | A1 | B70 | B44 |
| Compound 393 | N | A1 | B70 | B45 | Compound 394 | N | A1 | B70 | B46 |
| Compound 395 | N | A1 | B70 | B47 | Compound 396 | N | A1 | B70 | B48 |
| Compound 397 | N | A1 | B70 | B49 | Compound 398 | N | A1 | B70 | B50 |
| Compound 399 | N | A1 | B70 | B51 | Compound 400 | N | A1 | B70 | B52 |
| Compound 401 | N | A1 | B70 | B53 | Compound 402 | N | A1 | B70 | B54 |
| Compound 403 | N | A1 | B70 | B55 | Compound 404 | N | A1 | B70 | B56 |
| Compound 405 | N | A1 | B70 | B57 | Compound 406 | N | A1 | B70 | B58 |
| Compound 407 | N | A1 | B70 | B59 | Compound 408 | N | A1 | B70 | B60 |
| Compound 409 | N | A1 | B70 | B61 | Compound 410 | N | A1 | B70 | B62 |
| Compound 411 | N | A1 | B70 | B63 | Compound 412 | N | A1 | B70 | B64 |
| Compound 413 | N | A1 | B70 | B65 | Compound 414 | N | A1 | B70 | B66 |
| Compound 415 | N | A1 | B70 | B67 | Compound 416 | N | A1 | B70 | B68 |
| Compound 417 | N | A1 | B70 | B69 | Compound 418 | N | A1 | B70 | B70 |
| Compound 419 | N | A1 | B70 | B71 | Compound 420 | N | A1 | B70 | B72 |
| Compound 421 | N | A1 | B70 | B73 | Compound 422 | N | A1 | B70 | B74 |
| Compound 423 | N | A1 | B70 | B75 | Compound 424 | N | A1 | B70 | B76 |
| Compound 425 | N | A1 | B70 | B77 | Compound 426 | N | A1 | B70 | B78 |
| Compound 427 | N | A1 | B70 | B79 | Compound 428 | N | A1 | B70 | B80 |
| Compound 429 | N | A1 | B70 | B81 | Compound 430 | N | A1 | B70 | B82 |
| Compound 431 | N | A1 | B70 | B83 | Compound 432 | N | A1 | B70 | B84 |
| Compound 433 | N | A1 | B70 | B96 | Compound 434 | N | A1 | B70 | B97 |
| Compound 435 | N | A1 | B70 | B98 | Compound 436 | N | A1 | B70 | B99 |
| Compound 437 | N | A1 | B68 | B89 | Compound 438 | N | A1 | B68 | B15 |
| Compound 439 | N | A1 | B68 | B18 | Compound 440 | N | A1 | B68 | B20 |
| Compound 441 | N | A1 | B68 | B22 | Compound 442 | N | A1 | B68 | B25 |
| Compound 443 | N | A1 | B68 | B26 | Compound 444 | N | A1 | B68 | B30 |
| Compound 445 | N | A1 | B68 | B30 | Compound 446 | N | A1 | B68 | B38 |
| Compound 447 | N | A1 | B68 | B36 | Compound 448 | N | A1 | B68 | B46 |
| Compound 449 | N | A1 | B68 | B42 | Compound 450 | N | A1 | B68 | B55 |
| Compound 451 | N | A1 | B68 | B48 | Compound 452 | N | A1 | B68 | B62 |
| Compound 453 | N | A1 | B68 | B54 | Compound 454 | N | A1 | B68 | B69 |
| Compound 455 | N | A1 | B68 | B60 | Compound 456 | N | A1 | B68 | B73 |
| Compound 457 | N | A1 | B68 | B66 | Compound 458 | N | A1 | B68 | B77 |
| Compound 459 | N | A1 | B68 | B72 | Compound 460 | N | A1 | B68 | B81 |
| Compound 461 | N | A1 | B68 | B78 | Compound 462 | N | A1 | B68 | B90 |
| Compound 463 | N | A1 | B68 | B84 | Compound 464 | N | A1 | B68 | B91 |
| Compound 465 | CH | A1 | B1 | B14 | Compound 466 | CH | A1 | B2 | B14 |

-continued

| No. | $Z_1 = Z_2$ | X = Y | R | $R_N$ | No. | $Z_1 = Z_2$ | X = Y | R | $R_N$ |
|---|---|---|---|---|---|---|---|---|---|
| Compound 467 | CH | A1 | B3 | B14 | Compound 468 | CH | A1 | B4 | B14 |
| Compound 469 | CH | A1 | B5 | B14 | Compound 470 | CH | A1 | B6 | B14 |
| Compound 471 | CH | A1 | B7 | B14 | Compound 472 | CH | A1 | B8 | B14 |
| Compound 473 | CH | A1 | B9 | B14 | Compound 474 | CH | A1 | B10 | B14 |
| Compound 475 | CH | A1 | B11 | B14 | Compound 476 | CH | A1 | B12 | B14 |
| Compound 477 | CH | A1 | B13 | B14 | Compound 478 | CH | A1 | B14 | B14 |
| Compound 479 | CH | A1 | B15 | B14 | Compound 480 | CH | A1 | B16 | B14 |
| Compound 481 | CH | A1 | B17 | B14 | Compound 482 | CH | A1 | B18 | B14 |
| Compound 483 | CH | A1 | B19 | B14 | Compound 484 | CH | A1 | B20 | B14 |
| Compound 485 | CH | A1 | B21 | B14 | Compound 486 | CH | A1 | B22 | B14 |
| Compound 487 | CH | A1 | B23 | B14 | Compound 488 | CH | A1 | B24 | B14 |
| Compound 489 | CH | A1 | B25 | B14 | Compound 490 | CH | A1 | B26 | B14 |
| Compound 491 | CH | A1 | B27 | B14 | Compound 492 | CH | A1 | B28 | B14 |
| Compound 493 | CH | A1 | B29 | B14 | Compound 494 | CH | A1 | B30 | B14 |
| Compound 495 | CH | A1 | B31 | B14 | Compound 496 | CH | A1 | B32 | B14 |
| Compound 497 | CH | A1 | B33 | B14 | Compound 498 | CH | A1 | B34 | B14 |
| Compound 499 | CH | A1 | B35 | B14 | Compound 500 | CH | A1 | B36 | B14 |
| Compound 501 | CH | A1 | B37 | B14 | Compound 502 | CH | A1 | B38 | B14 |
| Compound 503 | CH | A1 | B39 | B14 | Compound 504 | CH | A1 | B40 | B14 |
| Compound 505 | CH | A1 | B41 | B14 | Compound 506 | CH | A1 | B42 | B14 |
| Compound 507 | CH | A1 | B43 | B14 | Compound 508 | CH | A1 | B44 | B14 |
| Compound 509 | CH | A1 | B45 | B14 | Compound 510 | CH | A1 | B46 | B14 |
| Compound 511 | CH | A1 | B47 | B14 | Compound 512 | CH | A1 | B48 | B14 |
| Compound 513 | CH | A1 | B49 | B14 | Compound 514 | CH | A1 | B50 | B14 |
| Compound 515 | CH | A1 | B51 | B14 | Compound 516 | CH | A1 | B52 | B14 |
| Compound 517 | CH | A1 | B53 | B14 | Compound 518 | CH | A1 | B54 | B14 |
| Compound 519 | CH | A1 | B55 | B14 | Compound 520 | CH | A1 | B56 | B14 |
| Compound 521 | CH | A1 | B57 | B14 | Compound 522 | CH | A1 | B58 | B14 |
| Compound 523 | CH | A1 | B59 | B14 | Compound 524 | CH | A1 | B60 | B14 |
| Compound 525 | CH | A1 | B61 | B14 | Compound 526 | CH | A1 | B62 | B14 |
| Compound 527 | CH | A1 | B63 | B14 | Compound 528 | CH | A1 | B64 | B14 |
| Compound 529 | CH | A1 | B65 | B14 | Compound 530 | CH | A1 | B66 | B14 |
| Compound 531 | CH | A1 | B67 | B14 | Compound 532 | CH | A1 | B68 | B14 |
| Compound 533 | CH | A1 | B69 | B14 | Compound 534 | CH | A1 | B70 | B14 |
| Compound 535 | CH | A1 | B71 | B14 | Compound 536 | CH | A1 | B72 | B14 |
| Compound 537 | CH | A1 | B73 | B14 | Compound 538 | CH | A1 | B74 | B14 |
| Compound 539 | CH | A1 | B75 | B14 | Compound 540 | CH | A1 | B76 | B14 |
| Compound 541 | CH | A1 | B77 | B14 | Compound 542 | CH | A1 | B78 | B14 |
| Compound 543 | CH | A1 | B79 | B14 | Compound 544 | CH | A1 | B80 | B14 |
| Compound 545 | CH | A1 | B81 | B14 | Compound 546 | CH | A1 | B82 | B14 |
| Compound 547 | CH | A1 | B83 | B14 | Compound 548 | CH | A1 | B84 | B14 |
| Compound 549 | CH | A1 | B85 | B14 | Compound 550 | CH | A1 | B86 | B14 |
| Compound 551 | CH | A1 | B87 | B14 | Compound 552 | CH | A1 | B88 | B14 |
| Compound 553 | CH | A2 | B1 | B14 | Compound 554 | CH | A2 | B6 | B14 |
| Compound 555 | CH | A2 | B12 | B14 | Compound 556 | CH | A2 | B14 | B14 |
| Compound 557 | CH | A2 | B20 | B14 | Compound 558 | CH | A2 | B28 | B14 |
| Compound 559 | CH | A2 | B30 | B14 | Compound 560 | CH | A2 | B35 | B14 |
| Compound 561 | CH | A2 | B38 | B14 | Compound 562 | CH | A2 | B39 | B14 |
| Compound 563 | CH | A2 | B41 | B14 | Compound 564 | CH | A2 | B42 | B14 |
| Compound 565 | CH | A2 | B49 | B14 | Compound 566 | CH | A2 | B54 | B14 |
| Compound 567 | CH | A2 | B56 | B14 | Compound 568 | CH | A2 | B64 | B14 |
| Compound 569 | CH | A2 | B68 | B14 | Compound 570 | CH | A2 | B69 | B14 |
| Compound 571 | CH | A2 | B70 | B14 | Compound 572 | CH | A2 | B72 | B14 |
| Compound 573 | CH | A2 | B75 | B14 | Compound 574 | CH | A2 | B78 | B14 |
| Compound 575 | CH | A2 | B79 | B14 | Compound 576 | CH | A2 | B80 | B14 |
| Compound 577 | CH | A2 | B82 | B14 | Compound 578 | CH | A2 | B83 | B14 |
| Compound 579 | CH | A2 | B85 | B14 | Compound 580 | CH | A2 | B88 | B14 |
| Compound 581 | CH | A3 | B1 | B14 | Compound 582 | CH | A3 | B6 | B14 |
| Compound 583 | CH | A3 | B12 | B14 | Compound 584 | CH | A3 | B14 | B14 |
| Compound 585 | CH | A3 | B20 | B14 | Compound 586 | CH | A3 | B28 | B14 |
| Compound 587 | CH | A3 | B30 | B14 | Compound 588 | CH | A3 | B35 | B14 |
| Compound 589 | CH | A3 | B38 | B14 | Compound 590 | CH | A3 | B39 | B14 |
| Compound 591 | CH | A3 | B41 | B14 | Compound 592 | CH | A3 | B42 | B14 |
| Compound 593 | CH | A3 | B49 | B14 | Compound 594 | CH | A3 | B54 | B14 |
| Compound 595 | CH | A3 | B56 | B14 | Compound 596 | CH | A3 | B64 | B14 |
| Compound 597 | CH | A3 | B68 | B14 | Compound 598 | CH | A3 | B69 | B14 |
| Compound 599 | CH | A3 | B70 | B14 | Compound 600 | CH | A3 | B72 | B14 |
| Compound 601 | CH | A3 | B75 | B14 | Compound 602 | CH | A3 | B78 | B14 |
| Compound 603 | CH | A3 | B79 | B14 | Compound 604 | CH | A3 | B80 | B14 |
| Compound 605 | CH | A3 | B82 | B14 | Compound 606 | CH | A3 | B83 | B14 |
| Compound 607 | CH | A3 | B85 | B14 | Compound 608 | CH | A3 | B88 | B14 |
| Compound 609 | CH | A4 | B1 | B14 | Compound 610 | CH | A4 | B6 | B14 |
| Compound 611 | CH | A4 | B12 | B14 | Compound 612 | CH | A4 | B14 | B14 |
| Compound 613 | CH | A4 | B20 | B14 | Compound 614 | CH | A4 | B28 | B14 |
| Compound 615 | CH | A4 | B30 | B14 | Compound 616 | CH | A4 | B35 | B14 |
| Compound 617 | CH | A4 | B38 | B14 | Compound 618 | CH | A4 | B39 | B14 |
| Compound 619 | CH | A4 | B41 | B14 | Compound 620 | CH | A4 | B42 | B14 |

-continued

| No. | $Z_1 = Z_2$ | X = Y | R | $R_N$ | No. | $Z_1 = Z_2$ | X = Y | R | $R_N$ |
| --- | --- | --- | --- | --- | --- | --- | --- | --- | --- |
| Compound 621 | CH | A4 | B49 | B14 | Compound 622 | CH | A4 | B54 | B14 |
| Compound 623 | CH | A4 | B56 | B14 | Compound 624 | CH | A4 | B64 | B14 |
| Compound 625 | CH | A4 | B68 | B14 | Compound 626 | CH | A4 | B69 | B14 |
| Compound 627 | CH | A4 | B70 | B14 | Compound 628 | CH | A4 | B72 | B14 |
| Compound 629 | CH | A4 | B75 | B14 | Compound 630 | CH | A4 | B78 | B14 |
| Compound 631 | CH | A4 | B79 | B14 | Compound 632 | CH | A4 | B80 | B14 |
| Compound 633 | CH | A4 | B82 | B14 | Compound 634 | CH | A4 | B83 | B14 |
| Compound 635 | CH | A4 | B85 | B14 | Compound 636 | CH | A4 | B88 | B14 |
| Compound 637 | CH | A5 | B1 | B14 | Compound 638 | CH | A5 | B6 | B14 |
| Compound 639 | CH | A5 | B12 | B14 | Compound 640 | CH | A5 | B14 | B14 |
| Compound 641 | CH | A5 | B20 | B14 | Compound 642 | CH | A5 | B28 | B14 |
| Compound 643 | CH | A5 | B30 | B14 | Compound 644 | CH | A5 | B35 | B14 |
| Compound 645 | CH | A5 | B38 | B14 | Compound 646 | CH | A5 | B39 | B14 |
| Compound 647 | CH | A5 | B41 | B14 | Compound 648 | CH | A5 | B42 | B14 |
| Compound 649 | CH | A5 | B49 | B14 | Compound 650 | CH | A5 | B54 | B14 |
| Compound 651 | CH | A5 | B56 | B14 | Compound 652 | CH | A5 | B64 | B14 |
| Compound 653 | CH | A5 | B68 | B14 | Compound 654 | CH | A5 | B69 | B14 |
| Compound 655 | CH | A5 | B70 | B14 | Compound 656 | CH | A5 | B72 | B14 |
| Compound 657 | CH | A5 | B75 | B14 | Compound 658 | CH | A5 | B78 | B14 |
| Compound 659 | CH | A5 | B79 | B14 | Compound 660 | CH | A5 | B80 | B14 |
| Compound 661 | CH | A5 | B82 | B14 | Compound 662 | CH | A5 | B83 | B14 |
| Compound 663 | CH | A5 | B85 | B14 | Compound 664 | CH | A5 | B88 | B14 |
| Compound 665 | CH | A6 | B1 | B14 | Compound 666 | CH | A6 | B6 | B14 |
| Compound 667 | CH | A6 | B12 | B14 | Compound 668 | CH | A6 | B14 | B14 |
| Compound 669 | CH | A6 | B20 | B14 | Compound 670 | CH | A6 | B28 | B14 |
| Compound 671 | CH | A6 | B30 | B14 | Compound 672 | CH | A6 | B35 | B14 |
| Compound 673 | CH | A6 | B38 | B14 | Compound 674 | CH | A6 | B39 | B14 |
| Compound 675 | CH | A6 | B41 | B14 | Compound 676 | CH | A6 | B42 | B14 |
| Compound 677 | CH | A6 | B49 | B14 | Compound 678 | CH | A6 | B54 | B14 |
| Compound 679 | CH | A6 | B56 | B14 | Compound 680 | CH | A6 | B64 | B14 |
| Compound 681 | CH | A6 | B68 | B14 | Compound 682 | CH | A6 | B69 | B14 |
| Compound 683 | CH | A6 | B70 | B14 | Compound 684 | CH | A6 | B72 | B14 |
| Compound 685 | CH | A6 | B75 | B14 | Compound 686 | CH | A6 | B78 | B14 |
| Compound 687 | CH | A6 | B79 | B14 | Compound 688 | CH | A6 | B80 | B14 |
| Compound 689 | CH | A6 | B82 | B14 | Compound 690 | CH | A6 | B83 | B14 |
| Compound 691 | CH | A6 | B85 | B14 | Compound 692 | CH | A6 | B88 | B14 |
| Compound 693 | CH | A7 | B1 | B14 | Compound 694 | CH | A7 | B6 | B14 |
| Compound 695 | CH | A7 | B12 | B14 | Compound 696 | CH | A7 | B14 | B14 |
| Compound 697 | CH | A7 | B20 | B14 | Compound 698 | CH | A7 | B28 | B14 |
| Compound 699 | CH | A7 | B30 | B14 | Compound 700 | CH | A7 | B35 | B14 |
| Compound 701 | CH | A7 | B38 | B14 | Compound 702 | CH | A7 | B39 | B14 |
| Compound 703 | CH | A7 | B41 | B14 | Compound 704 | CH | A7 | B42 | B14 |
| Compound 705 | CH | A7 | B49 | B14 | Compound 706 | CH | A7 | B54 | B14 |
| Compound 707 | CH | A7 | B56 | B14 | Compound 708 | CH | A7 | B64 | B14 |
| Compound 709 | CH | A7 | B68 | B14 | Compound 710 | CH | A7 | B69 | B14 |
| Compound 711 | CH | A7 | B70 | B14 | Compound 712 | CH | A7 | B72 | B14 |
| Compound 713 | CH | A7 | B75 | B14 | Compound 714 | CH | A7 | B78 | B14 |
| Compound 715 | CH | A7 | B79 | B14 | Compound 716 | CH | A7 | B80 | B14 |
| Compound 717 | CH | A7 | B82 | B14 | Compound 718 | CH | A7 | B83 | B14 |
| Compound 719 | CH | A7 | B85 | B14 | Compound 720 | CH | A7 | B88 | B14 |
| Compound 721 | CH | S | B1 | B14 | Compound 722 | CH | S | B6 | B14 |
| Compound 723 | CH | S | B12 | B14 | Compound 724 | CH | S | B2 | B14 |
| Compound 725 | CH | S | B20 | B14 | Compound 726 | CH | S | B28 | B14 |
| Compound 727 | CH | S | B30 | B14 | Compound 728 | CH | S | B35 | B14 |
| Compound 729 | CH | S | B38 | B14 | Compound 730 | CH | S | B39 | B14 |
| Compound 731 | CH | S | B41 | B14 | Compound 732 | CH | S | B42 | B14 |
| Compound 733 | CH | S | B49 | B14 | Compound 734 | CH | S | B54 | B14 |
| Compound 735 | CH | S | B56 | B14 | Compound 736 | CH | S | B64 | B14 |
| Compound 737 | CH | S | B68 | B14 | Compound 738 | CH | S | B69 | B14 |
| Compound 739 | CH | S | B70 | B14 | Compound 740 | CH | S | B72 | B14 |
| Compound 741 | CH | S | B75 | B14 | Compound 742 | CH | S | B78 | B14 |
| Compound 743 | CH | S | B79 | B14 | Compound 744 | CH | S | B80 | B14 |
| Compound 745 | CH | S | B82 | B14 | Compound 746 | CH | S | B83 | B14 |
| Compound 747 | CH | S | B85 | B14 | Compound 748 | CH | S | B88 | B14 |
| Compound 749 | CH | Se | B1 | B14 | Compound 750 | CH | Se | B6 | B14 |
| Compound 751 | CH | Se | B12 | B14 | Compound 752 | CH | Se | B2 | B14 |
| Compound 753 | CH | Se | B20 | B14 | Compound 754 | CH | Se | B28 | B14 |
| Compound 755 | CH | Se | B30 | B14 | Compound 756 | CH | Se | B35 | B14 |
| Compound 757 | CH | Se | B38 | B14 | Compound 758 | CH | Se | B39 | B14 |
| Compound 759 | CH | Se | B41 | B14 | Compound 760 | CH | Se | B42 | B14 |
| Compound 761 | CH | Se | B49 | B14 | Compound 762 | CH | Se | B54 | B14 |
| Compound 763 | CH | Se | B56 | B14 | Compound 764 | CH | Se | B64 | B14 |
| Compound 765 | CH | Se | B68 | B14 | Compound 766 | CH | Se | B69 | B14 |
| Compound 767 | CH | Se | B70 | B14 | Compound 768 | CH | Se | B72 | B14 |
| Compound 769 | CH | Se | B75 | B14 | Compound 770 | CH | Se | B78 | B14 |
| Compound 771 | CH | Se | B79 | B14 | Compound 772 | CH | Se | B80 | B14 |
| Compound 773 | CH | Se | B82 | B14 | Compound 774 | CH | Se | B83 | B14 |

-continued

| No. | $Z_1 = Z_2$ | $X = Y$ | R | $R_N$ | No. | $Z_1 = Z_2$ | $X = Y$ | R | $R_N$ |
|---|---|---|---|---|---|---|---|---|---|
| Compound 775 | CH | Se | B85 | B14 | Compound 776 | CH | Se | B88 | B14 |
| Compound 777 | CH | A1 | B1 | B16 | Compound 778 | CH | A1 | B6 | B16 |
| Compound 779 | CH | A1 | B5 | B16 | Compound 780 | CH | A1 | B10 | B16 |
| Compound 781 | CH | A1 | B9 | B16 | Compound 782 | CH | A1 | B14 | B16 |
| Compound 783 | CH | A1 | B13 | B16 | Compound 784 | CH | A1 | B18 | B16 |
| Compound 785 | CH | A1 | B17 | B16 | Compound 786 | CH | A1 | B22 | B16 |
| Compound 787 | CH | A1 | B21 | B16 | Compound 788 | CH | A1 | B26 | B16 |
| Compound 789 | CH | A1 | B25 | B16 | Compound 790 | CH | A1 | B30 | B16 |
| Compound 791 | CH | A1 | B29 | B16 | Compound 792 | CH | A1 | B34 | B16 |
| Compound 793 | CH | A1 | B33 | B16 | Compound 794 | CH | A1 | B38 | B16 |
| Compound 795 | CH | A1 | B37 | B16 | Compound 796 | CH | A1 | B42 | B16 |
| Compound 797 | CH | A1 | B41 | B16 | Compound 798 | CH | A1 | B49 | B16 |
| Compound 799 | CH | A1 | B45 | B16 | Compound 800 | CH | A1 | B56 | B16 |
| Compound 801 | CH | A1 | B49 | B16 | Compound 802 | CH | A1 | B63 | B16 |
| Compound 803 | CH | A1 | B55 | B164 | Compound 804 | CH | A1 | B70 | B16 |
| Compound 805 | CH | A1 | B61 | B16 | Compound 806 | CH | A1 | B72 | B16 |
| Compound 807 | CH | A1 | B67 | B16 | Compound 808 | CH | A1 | B82 | B16 |
| Compound 809 | CH | A1 | B73 | B16 | Compound 810 | CH | A1 | B84 | B16 |
| Compound 811 | CH | A1 | B79 | B16 | Compound 812 | CH | A1 | B88 | B16 |
| Compound 813 | CH | A1 | B70 | B89 | Compound 814 | CH | A1 | B70 | B2 |
| Compound 815 | CH | A1 | B70 | B3 | Compound 816 | CH | A1 | B70 | B4 |
| Compound 817 | CH | A1 | B70 | B5 | Compound 818 | CH | A1 | B70 | B90 |
| Compound 819 | CH | A1 | B70 | B91 | Compound 820 | CH | A1 | B70 | B92 |
| Compound 821 | CH | A1 | B70 | B93 | Compound 822 | CH | A1 | B70 | B94 |
| Compound 823 | CH | A1 | B70 | B95 | Compound 824 | CH | A1 | B70 | B12 |
| Compound 825 | CH | A1 | B70 | B96 | Compound 826 | CH | A1 | B70 | B97 |
| Compound 827 | CH | A1 | B70 | B15 | Compound 828 | CH | A1 | B70 | B16 |
| Compound 829 | CH | A1 | B70 | B17 | Compound 830 | CH | A1 | B70 | B18 |
| Compound 831 | CH | A1 | B70 | B19 | Compound 832 | CH | A1 | B70 | B20 |
| Compound 833 | CH | A1 | B70 | B21 | Compound 834 | CH | A1 | B70 | B22 |
| Compound 835 | CH | A1 | B70 | B23 | Compound 836 | CH | A1 | B70 | B24 |
| Compound 837 | CH | A1 | B70 | B25 | Compound 838 | CH | A1 | B70 | B26 |
| Compound 839 | CH | A1 | B70 | B27 | Compound 840 | CH | A1 | B70 | B28 |
| Compound 841 | CH | A1 | B70 | B29 | Compound 842 | CH | A1 | B70 | B30 |
| Compound 843 | CH | A1 | B70 | B31 | Compound 844 | CH | A1 | B70 | B32 |
| Compound 845 | CH | A1 | B70 | B33 | Compound 846 | CH | A1 | B70 | B34 |
| Compound 847 | CH | A1 | B70 | B35 | Compound 848 | CH | A1 | B70 | B36 |
| Compound 849 | CH | A1 | B70 | B37 | Compound 850 | CH | A1 | B70 | B38 |
| Compound 851 | CH | A1 | B70 | B39 | Compound 852 | CH | A1 | B70 | B40 |
| Compound 853 | CH | A1 | B70 | B41 | Compound 854 | CH | A1 | B70 | B42 |
| Compound 855 | CH | A1 | B70 | B43 | Compound 856 | CH | A1 | B70 | B44 |
| Compound 857 | CH | A1 | B70 | B45 | Compound 858 | CH | A1 | B70 | B46 |
| Compound 859 | CH | A1 | B70 | B47 | Compound 860 | CH | A1 | B70 | B48 |
| Compound 861 | CH | A1 | B70 | B49 | Compound 862 | CH | A1 | B70 | B50 |
| Compound 863 | CH | A1 | B70 | B51 | Compound 864 | CH | A1 | B70 | B52 |
| Compound 865 | CH | A1 | B70 | B53 | Compound 866 | CH | A1 | B70 | B54 |
| Compound 867 | CH | A1 | B70 | B55 | Compound 868 | CH | A1 | B70 | B56 |
| Compound 869 | CH | A1 | B70 | B57 | Compound 870 | CH | A1 | B70 | B58 |
| Compound 871 | CH | A1 | B70 | B59 | Compound 872 | CH | A1 | B70 | B60 |
| Compound 873 | CH | A1 | B70 | B61 | Compound 874 | CH | A1 | B70 | B62 |
| Compound 875 | CH | A1 | B70 | B63 | Compound 876 | CH | A1 | B70 | B64 |
| Compound 877 | CH | A1 | B70 | B65 | Compound 878 | CH | A1 | B70 | B66 |
| Compound 879 | CH | A1 | B70 | B67 | Compound 880 | CH | A1 | B70 | B68 |
| Compound 881 | CH | A1 | B70 | B69 | Compound 882 | CH | A1 | B70 | B70 |
| Compound 883 | CH | A1 | B70 | B71 | Compound 884 | CH | A1 | B70 | B72 |
| Compound 885 | CH | A1 | B70 | B73 | Compound 886 | CH | A1 | B70 | B74 |
| Compound 887 | CH | A1 | B70 | B75 | Compound 888 | CH | A1 | B70 | B76 |
| Compound 889 | CH | A1 | B70 | B77 | Compound 890 | CH | A1 | B70 | B78 |
| Compound 891 | CH | A1 | B70 | B79 | Compound 892 | CH | A1 | B70 | B80 |
| Compound 893 | CH | A1 | B70 | B81 | Compound 894 | CH | A1 | B70 | B82 |
| Compound 895 | CH | A1 | B70 | B83 | Compound 896 | CH | A1 | B70 | B84 |
| Compound 897 | CH | A1 | B70 | B98 | Compound 898 | CH | A1 | B70 | B99 |
| Compound 899 | CH | A1 | B70 | B100 | Compound 900 | CH | A1 | B70 | B101 |
| Compound 901 | CH | A1 | B68 | B89 | Compound 902 | CH | A1 | B68 | B15 |
| Compound 903 | CH | A1 | B68 | B18 | Compound 904 | CH | A1 | B68 | B20 |
| Compound 905 | CH | A1 | B68 | B22 | Compound 906 | CH | A1 | B68 | B25 |
| Compound 907 | CH | A1 | B68 | B26 | Compound 908 | CH | A1 | B68 | B30 |
| Compound 909 | CH | A1 | B68 | B30 | Compound 910 | CH | A1 | B68 | B38 |
| Compound 911 | CH | A1 | B68 | B36 | Compound 912 | CH | A1 | B68 | B46 |
| Compound 913 | CH | A1 | B68 | B42 | Compound 914 | CH | A1 | B68 | B55 |
| Compound 915 | CH | A1 | B68 | B48 | Compound 916 | CH | A1 | B68 | B62 |
| Compound 917 | CH | A1 | B68 | B54 | Compound 918 | CH | A1 | B68 | B69 |
| Compound 919 | CH | A1 | B68 | B60 | Compound 920 | CH | A1 | B68 | B73 |
| Compound 921 | CH | A1 | B68 | B66 | Compound 922 | CH | A1 | B68 | B77 |
| Compound 923 | CH | A1 | B68 | B72 | Compound 924 | CH | A1 | B68 | B81 |
| Compound 925 | CH | A1 | B68 | B78 | Compound 926 | CH | A1 | B68 | B99 |
| Compound 927 | CH | A1 | B68 | B84 | Compound 928 | CH | A1 | B68 | B100 |

-continued

| No. | $Z_1 = Z_2$ | X = Y | R | $R_N$ | No. | $Z_1 = Z_2$ | X = Y | R | $R_N$ |
|---|---|---|---|---|---|---|---|---|---|
| Compound 929 | N | A1 | B1 | B16 | Compound 930 | N | A1 | B2 | B16 |
| Compound 931 | N | A1 | B3 | B16 | Compound 932 | N | A1 | B4 | B16 |
| Compound 933 | N | A1 | B5 | B16 | Compound 934 | N | A1 | B6 | B16 |
| Compound 935 | N | A1 | B7 | B16 | Compound 936 | N | A1 | B8 | B16 |
| Compound 937 | N | A1 | B9 | B16 | Compound 938 | N | A1 | B10 | B16 |
| Compound 939 | N | A1 | B11 | B16 | Compound 940 | N | A1 | B12 | B16 |
| Compound 941 | N | A1 | B22 | B16 | Compound 942 | N | A1 | B25 | B16 |
| Compound 943 | N | A1 | B26 | B16 | Compound 944 | N | A1 | B27 | B16 |
| Compound 945 | N | A1 | B28 | B16 | Compound 946 | N | A1 | B29 | B16 |
| Compound 947 | N | A1 | B30 | B16 | Compound 948 | N | A1 | B31 | B16 |
| Compound 949 | N | A1 | B38 | B16 | Compound 950 | N | A1 | B39 | B16 |
| Compound 951 | N | A1 | B41 | B16 | Compound 952 | N | A1 | B42 | B16 |
| Compound 953 | N | A1 | B43 | B16 | Compound 954 | N | A1 | B52 | B16 |
| Compound 955 | N | A1 | B67 | B16 | Compound 956 | N | A1 | B68 | B16 |
| Compound 957 | N | A1 | B69 | B16 | Compound 958 | N | A1 | B72 | B16 |
| Compound 959 | N | A1 | B74 | B16 | Compound 960 | N | A1 | B81 | B16 |
| Compound 961 | N | A1 | B82 | B16 | Compound 962 | N | A1 | B83 | B16 |
| Compound 963 | N | A1 | B84 | B16 | Compound 964 | N | A1 | B85 | B16 |
| Compound 965 | N | A1 | B89 | B14 | Compound 966 | N | A1 | B90 | B14 |
| Compound 967 | N | A1 | B91 | B14 | Compound 968 | N | A1 | B92 | B14 |
| Compound 969 | N | A1 | B93 | B14 | Compound 970 | N | A1 | B94 | B14 |
| Compound 971 | N | A1 | B95 | B14 | Compound 972 | N | A1 | B96 | B14 |
| Compound 973 | N | A1 | B97 | B14 | Compound 974 | N | A1 | B98 | B14 |
| Compound 975 | N | A1 | B99 | B14 | Compound 976 | N | A1 | B100 | B14 |
| Compound 977 | N | A1 | B101 | B14 | Compound 978 | N | A1 | B102 | B14 |
| Compound 979 | N | A1 | B103 | B14 | Compound 980 | N | A1 | B104 | B14 |
| Compound 981 | N | A1 | B105 | B14 | Compound 982 | N | A1 | B106 | B14 |
| Compound 983 | N | A1 | B107 | B14 | Compound 984 | N | A1 | B108 | B14 |
| Compound 985 | CH | A1 | B89 | B14 | Compound 986 | CH | A1 | B90 | B14 |
| Compound 987 | CH | A1 | B91 | B14 | Compound 988 | N | A1 | B56 | B16 |
| Compound 989 | N | A1 | B68 | B16 | Compound 990 | N | A1 | B70 | B16 |
| Compound 1003 | N | A1 | B13 | B16 | Compound 1004 | N | A1 | B13 | B17 |
| Compound 1005 | N | A1 | B13 | B18 | Compound 1006 | N | A1 | B13 | B19 |
| Compound 1007 | N | A1 | B13 | B25 | Compound 1008 | N | A1 | B13 | B29 |
| Compound 1009 | N | A1 | B13 | B30 | Compound 1010 | N | A1 | B13 | B38 |
| Compound 1011 | N | A1 | B13 | B39 | Compound 1012 | N | A1 | B13 | B55 |
| Compound 1013 | N | A1 | B13 | B68 | Compound 1014 | N | A1 | B13 | B92 |
| Compound 1015 | N | A1 | B13 | B96 | Compound 1016 | N | A1 | B13 | B103; | wherein, when $X_1$ and $X_2$ are N, wherein $Z_1$, $Z_2$, X, Y, and $R_v$ are correspondingly selected from the atoms or groups as shown in the following table, and the Compound 991 to Compound 1002 are:

| No. | $Z_1 = Z_2$ | X = Y | $R_N$ | No. | $Z_1 = Z_2$ | X = Y | $R_N$ |
|---|---|---|---|---|---|---|---|
| Compound 991 | N | A1 | B25 | Compound 992 | N | A1 | B26 |
| Compound 993 | N | A1 | B28 | Compound 994 | N | A1 | B30 |
| Compound 995 | N | A1 | B31 | Compound 996 | N | A1 | B39 |
| Compound 997 | N | A1 | B41 | Compound 998 | N | A1 | B42 |
| Compound 999 | N | A1 | B43 | Compound 1000 | N | A1 | B52 |
| Compound 1001 | N | A1 | B68 | Compound 1002 | N | A1 | B72. |

18. An electroluminescent device comprising:
an anode,
a cathode,
and an organic layer disposed between the anode and the cathode, wherein the organic layer comprises a compound having Formula 1:

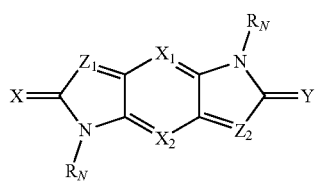

Formula 1 wherein $X_1$ and $X_2$ are, at each occurrence identically or differently, selected from CR or N;
X and Y are, at each occurrence identically or differently, selected from O, S, Se, NR' or CR"R'";
$Z_1$ and $Z_2$ are, at each occurrence identically or differently, selected from CR or N; and when $Z_1$ and $Z_2$ are both CR, at least one of X and Y is S, Se, NR', or CR"R'";
$R_N$ is, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
R, R', R" and R'" are, at each occurrence identically or differently, selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
at least one of R, R', R" and R'" is a group having at least one electron-withdrawing group;
any adjacent R, R', R" and R'" substituents may be optionally joined to form a ring.

19. The electroluminescent device of claim 18, wherein the organic layer is a hole injection layer or a hole transporting layer, and the hole injection layer or the hole transporting layer is formed from the compound having Formula 1 alone.

20. The electroluminescent device of claim 18, wherein the organic layer is a hole injection layer or a hole transporting layer, and the hole injection layer or the hole transporting layer further comprise at least one hole transporting material; wherein the molar doping ratio of the compound having Formula 1 to the hole transporting material is from 10000:1 to 1:10000; preferably, the molar doping ratio of the compound having Formula 1 to the hole transporting material is from 10:1 to 1:100.

21. The electroluminescent device of claim 20, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

22. The electroluminescent device of claim 18, wherein the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer;
wherein the p-type charge generation layer comprises a compound having Formula 1; preferably, the p-type charge generation layer may further comprises at least one hole transporting material, wherein the molar doping ratio of the compound having Formula 1 to the hole transporting material is from 10000:1 to 1:10000; preferably, the molar doping ratio of the compound having Formula 1 to the hole transporting material is from 10:1 to 1:100.

23. The electroluminescent device of claim 22, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex.

24. The electroluminescent device of claim 22, wherein the charge generation layer further includes a buffer layer disposed between the p-type charge generation layer and the n-type charge generation layer, wherein the buffer layer comprises the compound.

25. The electroluminescent device of claim 18, the fabrication method of the electroluminescent device is vacuum deposition method.

26. A compound formulation comprising the compound of claim 1.

* * * * *